United States Patent
Huang et al.

(10) Patent No.: US 10,920,065 B2
(45) Date of Patent: Feb. 16, 2021

(54) LOW MOLECULAR WEIGHT DRY POWDER POLYMER FOR USE AS PAPER-MAKING DRY STRENGTH AGENT

(71) Applicant: Ecolab USA Inc., St. Paul, MN (US)

(72) Inventors: Heqing Huang, Naperville, IL (US);
David Jordan, Evanston, IL (US);
Robert M. Lowe, Chicago, IL (US);
Jeffrey Cramm, Batavia, IL (US);
Weiguo Cheng, Naperville, IL (US);
Mingli Wei, Naperville, IL (US)

(73) Assignee: ECOLAB USA INC., St. Paul, MN (US)

(*) Notice: Subject to any disclaimer, the term of this patent is extended or adjusted under 35 U.S.C. 154(b) by 0 days.

(21) Appl. No.: 15/620,176

(22) Filed: Jun. 12, 2017

(65) Prior Publication Data

US 2017/0355846 A1 Dec. 14, 2017

Related U.S. Application Data

(60) Provisional application No. 62/348,400, filed on Jun. 10, 2016.

(51) Int. Cl.
*C08L 55/00* (2006.01)
*D21H 21/20* (2006.01)
(Continued)

(52) U.S. Cl.
CPC .......... *C08L 55/005* (2013.01); *C07C 219/08* (2013.01); *C07C 305/04* (2013.01);
(Continued)

(58) Field of Classification Search
CPC ... C08L 55/005; C07C 219/08; C07C 305/04; C07C 307/04; C08F 220/56;
(Continued)

(56) References Cited

U.S. PATENT DOCUMENTS

| | | |
|---|---|---|
| 3,872,039 A | 3/1975 | Vaughn et al. |
| 3,875,098 A | 4/1975 | Sedlak |

(Continued)

FOREIGN PATENT DOCUMENTS

| | | |
|---|---|---|
| CN | 101942779 A | 1/2011 |
| CN | 102154943 A | 8/2011 |

(Continued)

OTHER PUBLICATIONS

Mata et al. Aggregation behavior of quaternary salt based cationic surfactants. Thermochimica Acta 428 (2005) 147-155 (Year: 2005).*

(Continued)

*Primary Examiner* — John E Uselding
(74) *Attorney, Agent, or Firm* — Eric D. Babych; Barnes & Thornburg LLP

(57) ABSTRACT

The invention provides an associative polymer, a powder, and a process for making a powder comprising, networking one or more associative polymer(s) and one or more optional surfactant(s) to form a wet gel, and forming a powder from the wet gel, wherein the associative polymer(s) have a weight average molecular weight of from about 10 kDa to about 2,000 kDa.

13 Claims, 2 Drawing Sheets

(51) Int. Cl.

| | | |
|---|---|---|
| D21H 17/37 | (2006.01) | |
| D21H 21/24 | (2006.01) | |
| D21H 21/18 | (2006.01) | |
| C07C 219/08 | (2006.01) | |
| C07C 305/04 | (2006.01) | |
| C07D 307/04 | (2006.01) | |
| C08F 220/56 | (2006.01) | |
| C08G 65/00 | (2006.01) | |
| C08K 5/3435 | (2006.01) | |
| C08F 220/28 | (2006.01) | |

(52) U.S. Cl.
CPC .......... *C07D 307/04* (2013.01); *C08F 220/56* (2013.01); *C08G 65/002* (2013.01); *C08K 5/3435* (2013.01); *D21H 17/37* (2013.01); *D21H 17/375* (2013.01); *D21H 21/18* (2013.01); *D21H 21/20* (2013.01); *D21H 21/24* (2013.01); *C08F 220/285* (2020.02)

(58) Field of Classification Search
CPC .... C07D 307/04; D21H 21/20; D21H 17/375; D21H 21/24; D21H 17/37; D21H 21/18; C08G 65/002; C08K 5/3435
See application file for complete search history.

(56) References Cited

U.S. PATENT DOCUMENTS

| | | |
|---|---|---|
| 4,115,187 A | 9/1978 | Davidson |
| 4,217,425 A | 8/1980 | Ballweber et al. |
| 4,392,917 A | 7/1983 | Lipowski et al. |
| 4,426,485 A | 1/1984 | Hoy et al. |
| 4,427,821 A | 1/1984 | Fong et al. |
| 4,535,098 A | 8/1985 | Evani et al. |
| 4,599,390 A | 7/1986 | Fan et al. |
| 4,713,431 A | 12/1987 | Bhattacharyya et al. |
| 4,744,864 A | 5/1988 | Deets et al. |
| 4,795,531 A | 1/1989 | Sofia et al. |
| 4,835,206 A | 5/1989 | Farrar et al. |
| 4,835,234 A | 5/1989 | Valint et al. |
| 4,874,588 A | 10/1989 | Sortwell et al. |
| 4,921,903 A | 5/1990 | Fong |
| 5,221,435 A | 6/1993 | Smith, Jr. |
| 5,234,604 A | 8/1993 | Liao et al. |
| RE34,383 E | 9/1993 | St. John et al. |
| 5,252,692 A | 10/1993 | Lovy et al. |
| 5,435,922 A | 7/1995 | Ramesh et al. |
| 5,541,252 A | 7/1996 | Schmitt et al. |
| 5,942,573 A | 8/1999 | Doki et al. |
| 5,980,878 A | 11/1999 | Torgerson et al. |
| 6,100,322 A | 8/2000 | Persson et al. |
| 6,228,217 B1 | 5/2001 | Dickerson et al. |
| 6,274,667 B1 | 8/2001 | Shannon et al. |
| 6,365,667 B1 | 4/2002 | Shannon et al. |
| 6,406,593 B1 | 6/2002 | Heard et al. |
| 6,960,617 B2 | 11/2005 | Omidian et al. |
| 7,442,280 B1 | 10/2008 | Klemets et al. |
| 7,700,702 B2 | 4/2010 | Gaillard et al. |
| 7,973,095 B2 | 7/2011 | Herth et al. |
| 8,241,618 B2 | 8/2012 | Brandt et al. |
| 8,425,726 B2 | 4/2013 | Buwono et al. |
| 8,758,562 B2 | 6/2014 | Krapsch et al. |
| RE45,383 E | 2/2015 | St. John et al. |
| 9,279,217 B2 | 3/2016 | Hietaniemi et al. |
| 9,567,708 B2 | 2/2017 | Cheng et al. |
| 9,822,297 B2 | 11/2017 | Brinkman et al. |
| 2003/0022981 A1 | 1/2003 | Baxter et al. |
| 2004/0110861 A1 | 6/2004 | Shorbu et al. |
| 2005/0124704 A1 | 6/2005 | Rasheed et al. |
| 2005/0161183 A1 | 7/2005 | Covarrubias |
| 2005/0230319 A1 | 10/2005 | Mori et al. |
| 2006/0065380 A1 | 3/2006 | Garnier et al. |
| 2006/0142432 A1 | 6/2006 | Harrington et al. |
| 2006/0270801 A1 | 11/2006 | Hagiopol et al. |
| 2006/0276597 A1 | 12/2006 | Quadir et al. |
| 2006/0289136 A1 | 12/2006 | Doherty et al. |
| 2006/0289137 A1 | 12/2006 | Gelman et al. |
| 2008/0004405 A1 | 1/2008 | Mori et al. |
| 2008/0058456 A1 | 3/2008 | Chiou et al. |
| 2008/0216979 A1 | 9/2008 | Schaffer |
| 2009/0074698 A1 | 3/2009 | Biganska |
| 2009/0145566 A1 | 6/2009 | Esser et al. |
| 2009/0165978 A1 | 7/2009 | Hagiopol et al. |
| 2010/0076145 A1 | 3/2010 | Bobsein et al. |
| 2010/0190948 A1 | 7/2010 | Proverb et al. |
| 2010/0286434 A1 | 11/2010 | Bobsein et al. |
| 2010/0331510 A1 | 12/2010 | Reichenbach-Klinke et al. |
| 2011/0056640 A1 | 3/2011 | Cyr et al. |
| 2011/0155339 A1 | 6/2011 | Brungardt et al. |
| 2011/0281980 A1 | 11/2011 | Bobsein et al. |
| 2012/0129734 A1 | 5/2012 | Reichenbach-Klinke et al. |
| 2012/0132382 A1 | 5/2012 | Hund et al. |
| 2014/0360691 A1 | 12/2014 | Hietaniemi et al. |
| 2015/0059998 A1 | 3/2015 | Zhao et al. |
| 2015/0087796 A1 | 3/2015 | Millard et al. |
| 2015/0167245 A1 | 6/2015 | Cheng et al. |
| 2015/0197893 A1 | 7/2015 | Cheng et al. |
| 2015/0367018 A1 | 12/2015 | Oshima et al. |
| 2016/0097160 A1 | 4/2016 | Castro et al. |
| 2016/0097161 A1 | 4/2016 | Benz et al. |
| 2016/0244594 A1 | 8/2016 | Langlotz |
| 2016/0311940 A1 | 10/2016 | Hund et al. |
| 2016/0326698 A1 | 11/2016 | Chen et al. |
| 2017/0029546 A1* | 2/2017 | Langlotz ............... C08F 220/56 |
| 2017/0037298 A1 | 2/2017 | Li et al. |
| 2017/0037299 A1 | 2/2017 | Le et al. |
| 2017/0037574 A1 | 2/2017 | Grimm et al. |
| 2017/0037575 A1 | 2/2017 | Hund et al. |

FOREIGN PATENT DOCUMENTS

| | | |
|---|---|---|
| CN | 102532409 A | 7/2012 |
| CN | 102660150 A | 9/2012 |
| CN | 104844760 A | 8/2015 |
| EP | 0374478 A2 | 6/1990 |
| EP | 0614950 A1 | 9/1994 |
| EP | 2933271 A | 10/2015 |
| FR | 2377447 A2 | 8/1978 |
| GB | 1372787 A | 11/1974 |
| JP | 54-93089 A | 7/1979 |
| JP | 2002-054088 A | 2/2002 |
| WO | WO 98/35095 A1 | 8/1998 |
| WO | WO 00/34582 A1 | 6/2000 |
| WO | 2006071633 A1 | 7/2006 |
| WO | WO 2012/042157 A1 | 4/2012 |
| WO | 2012100156 A1 | 7/2012 |
| WO | WO 2013/153004 A1 | 10/2013 |
| WO | WO 2014/076372 A | 5/2014 |
| WO | 2015110703 A1 | 7/2015 |
| WO | WO 2016/120524 A1 | 8/2016 |
| WO | 2016170230 A1 | 10/2016 |
| WO | 2017106310 A1 | 6/2017 |

OTHER PUBLICATIONS

English Machine translation of WO 2012/042157. (Year: 2012).*
European Patent Office, International Search Report in International Patent Application No. PCT/US2017/036996, 4 pp. (dated Sep. 14, 2017).
European Patent Office, Written Opinion in International Patent Application No. PCT/US2017/036996, 9 pp. (dated Sep. 14, 2017).
Abson et al., "Wet-end behavior or dry strength additives," *Tappi Journal*, vol. 68, No. 1, pp. 76-78 (Jan. 1985).
Lingström et al., "Polyelectrolyte multilayers on wood fibers: Influence of molecular weight on layer properties and mechanical properties of papers from treated fibers," *Journal of Colloid and Interface Science*, vol. 328, pp. 233-242 (2008).
Ma et al., "Study on Synthesis of Cationic Water in Water Polyacrylamide Emulsion Strength Agent," *Advanced Materials Research*, vols. 581-582, pp. 164-167 (Oct. 22, 2012).

(56) References Cited

OTHER PUBLICATIONS

Marimuthu et al., "Anionic Acrylamide Co-Polymer as Dry Strength Additive for Paper," *Ippta J.*, vol. 22, No. 3, pp. 131-135 (Jul.-Sep. 2010).

McLean et al., "Synthesis of Guar Gum-Graft-Poly(Acrylamide-Co-Diallyldimethylammonium Chloride) and its Application in the Pulp and Paper Industry," *BioResources*, vol. 6, No. 4, pp. 4168-4180 (2011).

Nakamura, "PAM-type Ply Bond Strength agent 'Himoloc MJ-450'," *Japan Tappi Journal*, vol. 57, No. 11, pp. 1618-1621 (2003).

Nobukuni et al., "The Latest Technological Trends of PAM Based Dry Strength Resins," *Kami-pa-gi-kyō-shi*, vol. 70, No. 5, pp. 493-497 (Aug. 2016).

Richardson et al., "Optimisation of neutral paper-making wet end chemistry for pitch free newsprint manufacture," Appita Annual General Conference, pp. 219-226 (2003); Conference: Proceedings of the 57th Appita Annual General Conference and Exhibit, May 5, 2003-May 7, 2003.

Suzuki et al., "Novel PAM Based Dry Strength Resins," *Japan Tappi Journal*, vol. 66.5, pp. 477-480 (Jan. 1, 2013).

Vanerek, "Filler Retention in Papermaking by Polymeric and Microparticulate Retention Aid Systems," ProQuest Dissertations and Theses Global, 2005; ISBN-13: 9780494129609; Paper No. NR12960; Publisher: ProQuest LLC (269 pp.).

Zhang et al., "Preparation of Polyacrylamide in Brine with Aqueous Two-phase Copolymerization and Its Application as Paper Strengthen Agent," *China Pulp & Paper*, vol. 27, No. 7, pp. 32-35 (2008).

Zhu et al., "Study on Branched Polyacrylamide Preparation and Application," *Advanced Materials Research*, vol. 174, pp. 490-493 (2011) (English Abstract Only).

Zhu et al., "Preparation of Active Resistant-Electrolytic Amphoteric Polyacrylamide and Its Application as Paper Strength Aid," *Journal of Xi' an University of Technology*, vol. 26, No. 4, pp. 412-416 (2010).

PCT/US2018/044562 International Search Report, dated Jul. 11, 2018.

International Search Report and Written Opinion for PCT/US2018/065358, dated Mar. 21, 2019, 11 pages.

Daoud-Mahammed, S. et al. "Original tamoxifen-loaded gels containing cyclodextrins: in situ self-assembling systems for cancer treatment," Journal Drug Delivery Science Technology, vol. 14(1), pp. 51-55 (2004).

"Fixative Polymers and Hair Styling Compositions Thereof," IP.com Journal, 44 pages (May 20, 2015).

Shen, Yi-ding et al. "Study on aqueous solution properties of hydrophobically associating cationic polyacrylamides and its application," Modern Chemical Industry, vol. 27(4), pp. 38-40 + 42 (Apr. 2007), English abstract only.

Volet, Gisèle et al. "pH Sensitive supramolecular assembling system between a new linear water soluble β-cyclodextrin terpolymer and an amphiphilic poly(ethylene oxide)," European Polymer Joumal, vol. 45(3), pp. 852-862 (2009).

Wang, Ying et al. "Cyclodextrins modify the properties of cationic polyacrylamides," Journal of Colloid and Interface Science, vol. 339(2), pp. 325-329 (2009).

Wenz, Gerhard et al. "Association Thickener by Host-Guest Interaction of β-Cyclodextrin Polymers and Guest Polymers," Associative Polymers in Aqueous Media, Chapter 16. Washington DC: American Chemical Society, vol. 765, pp. 271-283 (Aug. 10, 2000).

Wintgens, Véronique et al. "Aqueous Polysaccharide Associations Mediated by β-Cyclodextrin Polymers," Biomacromolecules, vol. 9(5), pp. 1434-1442 (2008).

Wintgens, Véronique et al. "Water-soluble γ-cyclodextrin polymers with high molecular weight and their complex forming properties," European Polymer Journal, vol. 46(9), pp. 1915-1922, (2010).

Wu, Weibing et al. "Preparation and Application of Hydrophobically Associating Cationic Polyacrylamide," Advanced Materials Research, vols. 284-286, pp. 1808-1814, (2011).

\* cited by examiner

LOW MOLECULAR WEIGHT DRY POWDER POLYMER FOR USE AS PAPER-MAKING DRY STRENGTH AGENT

CROSS-REFERENCE TO RELATED APPLICATIONS

This application claims the benefit of U.S. Provisional Application No. 62/348,400, filed Jun. 10, 2016, the disclosure of which is incorporated by reference herein in its entirety.

BACKGROUND OF THE INVENTION

High molecular weight polymers (e.g., at least 2 million Daltons) are commonly used in papermaking as retention and drainage aids to improve dewatering of the fiber slurry and the retention of fine particles in the sheet. Polymers with relatively low molecular weight (e.g., typically lower than 2 million Daltons) are also typically employed to help improve the strength of the sheet. Generally, in order to improve paper sheet strength, strength aids are required in high dosages (e.g., about 2-4 lbs active/ton of dry pulp). Addition of high dosages (i.e., 2-4 lbs active/ton of dry pulp) of high molecular weight polymers results in high flocculation and a paper sheet product, which lacks uniformity. Thus, high molecular weight polymers are typically not utilized as strength aids.

Both high and low molecular weight polymers can be provided to the papermaker as aqueous polymer solutions. However, solution based polymers have high costs associated with transportation, degradation due to long-term storage instability, as well as costs associated with, and facilities required for application to the paper machine. Powder-based strength aids have the capacity to improve such costs associated with transportation and addition to the paper machine. Some high molecular weight polymers can be formed into dry powder via a process comprising, inter alia, forming a polymer wet gel, cutting the wet gel, granulating the cut wet gel, drying the granules, and grinding the dried granules. However, due to their relative insolubility, they require large makedown units to obtain a solution-based polymer capable of being added to the paper machine. Thus, there remains a need for a low molecular weight strength aid powder for use in the papermaking process, which can be added to the paper machine as a powder, or as a solid slurry. However, low molecular weight (e.g., 2 million Daltons or less) polymers cannot be processed in the same fashion as high molecular weight polymers. Generally, the polymer wet gel of low molecular weight polymers is too soft to cut and process. Therefore, conventional strength aids are typically low molecular weight solution polymers.

One technique used to obtain a processable polymer wet gel out of low molecular weight polymers is to include permanent chemical cross-linking in the polymer backbone. Unfortunately, the permanently cross-linked low molecular weight polymers transform into high molecular weight polymers due to the crosslinking. In addition, the dry powder produced by this technique is typically insoluble in water, thereby rendering the powder useless in the papermaking process.

BRIEF SUMMARY OF THE INVENTION

A process for making a powder comprising one or more associatively networked polymer(s) of low molecular weight is provided. The process comprises networking one or more associative polymer(s) and one or more optional surfactants to form a wet gel, and forming a powder from the wet gel, wherein the associative polymer(s) have a weight average molecular weight of from about 10 kDa to about 2,000 kDa.

Additionally, a powder is provided. The powder comprises one or more associative polymer(s) comprising one or more associative monomer unit(s) and one or more additional monomer unit(s) selected from at least one of a cationic monomer unit, an anionic monomer unit, a nonionic monomer unit, a zwitterionic monomer unit, or a combination thereof, and optionally one or more surfactant(s), wherein the associative polymer(s) have a weight average molecular weight of from about 10 kDa to about 2,000 kDa.

Additionally, an associative polymer is provided. The associative polymer comprises one or more associative monomer unit(s), one or more additional monomer unit(s), one or more monomer unit(s) derived from a monomer of Formula I, and optionally one or more piperidine-2,6-dione unit(s), wherein the one or more piperidine-2,6-dione(s) are formed upon cyclization of an acrylamide nitrogen of the monomer unit derived from a monomer of Formula I on a carbonyl of the additional monomer unit, wherein the associative polymer has a weight average molecular weight of from about 10 kDa to about 2,000 kDa.

The processes of the present disclosure provide an approach to forming a polymer wet gel, comprising low molecular weight polymers, capable of being machine processed into powder. Generally, the resulting powder is water dispersible in which the degree of solubility is dependent on the level of dilution and/or the presence of a surfactant. Typically, the powder is dispersible in water, and thus, can be incorporated into the papermaking process. In particular, the processes and compositions described herein utilize a networking technique that improves the strength of the polymer wet gel and dissipates upon dilution with water. In addition, the powder comprising low molecular weight associative polymer(s) provided by the processes provided herein, when utilized in a papermaking process, generates paper having strength properties similar to that of paper obtained using conventional solution strength aids.

DETAILED DESCRIPTION OF THE INVENTION

Figure 1:
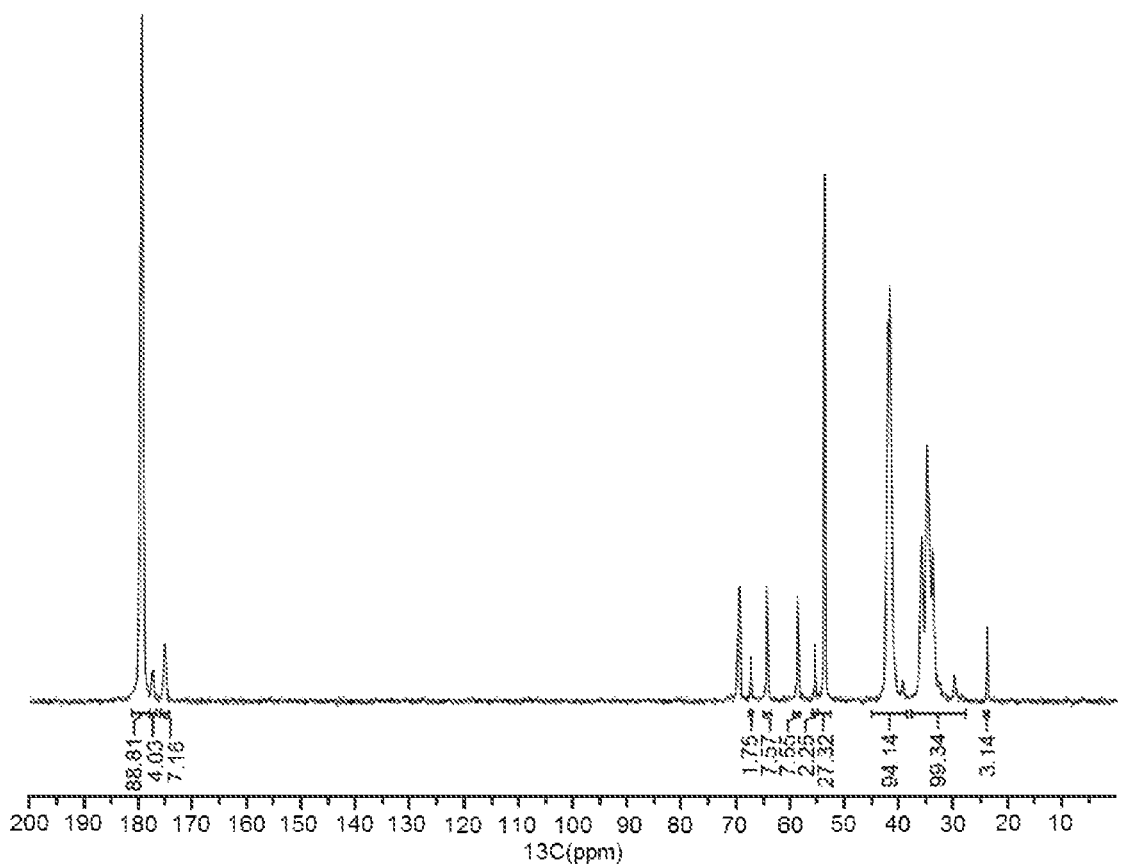
FIG. 1 is an exemplary $^{13}$C NMR spectrum of the associative polymer described in Example 5.

A process for making a powder is provided. The process comprises forming a wet gel comprising one or more associative polymer(s) and optionally one or more surfactant(s), and forming a powder from the wet gel, wherein the associative polymer(s) have a weight average molecular weight of from about 10 kDa to about 2,000 kDa.

In some embodiments, the process comprises forming a wet gel comprising one or more associative polymer(s) and optionally one or more surfactant(s), cutting the wet gel to form granules, and converting the granules to form a powder, wherein the associative polymer(s) have a weight average molecular weight of from about 10 kDa to about 2,000 kDa.

The powder comprises one or more associatively networked polymer(s). For example, the powder can comprise a plurality (e.g., at least two polymer molecules) of associatively networked polymer(s), wherein the associatively networked polymers have the same molecular structure (i.e., one associatively networked polymer), or the powder can comprise a plurality of associatively networked polymers, wherein the associatively networked polymers have varying molecular structures (i.e., more than one associatively networked polymer). The one or more associatively networked polymer(s) can be any suitable polymer. For example, the one or more associatively networked polymer(s) can be homopolymers, copolymers, terpolymers, or greater, or a combination thereof. In certain embodiments, the one or more associatively networked polymer(s) are terpolymers.

The associatively networked polymer(s) can be cationic, anionic, amphoteric, non-ionic, or zwitterionic. In some embodiments, the associatively networked polymer(s) are cationic. As used herein, "cationic" polymers refer to polymers containing cationic monomer units or a combination of cationic monomer units and non-ionic monomer units. In some embodiments, the associatively networked polymer(s) are anionic. As used herein, "anionic" polymers refer to polymers containing anionic monomer units or a combination of anionic monomer units and non-ionic monomer units. In some embodiments, the associatively networked polymer(s) are amphoteric. As used herein, "amphoteric" polymers refer to polymers containing cationic monomer units and anionic monomer units, or cationic monomer units, anionic monomer units, and non-ionic monomer units. In some embodiments, the associatively networked polymer(s) are non-ionic. As used herein, "non-ionic" polymers refer to polymers containing non-ionic monomer units. In some embodiments, the associatively networked polymer(s) are zwitterionic. As used herein, "zwitterionic" polymers refer to polymers containing zwitterionic monomer units or a combination of zwitterionic monomer units and cationic monomer units, anionic monomer units, and/or non-ionic monomer units.

The associatively networked polymer(s) can exist as any suitable structure type. For example, the associatively networked polymer(s) can exist as alternating polymers, random polymers, block polymers, graft polymers, linear polymers, branched polymers, cyclic polymers, or a combination thereof. The associatively networked polymer(s) can contain a single monomer unit, or any suitable number of different monomer units. For example, the associatively networked polymer(s) can contain 2 different monomer units, 3 different monomer units, 4 different monomer units, 5 different monomer units, or 6 different monomer units. The associatively networked polymer(s)' monomer units can exist in any suitable concentration and any suitable proportion.

In certain embodiments, the powder comprises one or more associatively networked polymer(s), wherein the associative polymer (i.e., absent of networking) have a weight average molecular weight of from about 10 kDa to about 2,000 kDa. The associatively networked polymer(s) can have a weight average molecular weight of about 2,000 kDa or less, for example, about 1,800 kDa or less, about 1,600 kDa or less, about 1,400 kDa or less, about 1,200 kDa or less, about 1,000 kDa or less, about 900 kDa, or less, about 800 kDa, or less, about 700 kDa or less, about 600 kDa or less, or about 500 kDa or less. Alternatively, or in addition, the associatively networked polymer(s) can have a weight average molecular weight of about 10 kDa or more, for example, about 50 kDa or more, about 100 kDa or more, about 200 kDa or more, about 300 kDa or more, or about 400 kDa or more. Thus, the associatively networked polymer(s) can have a weight average molecular weight bounded by any two of the aforementioned endpoints. For example, the associatively networked polymer(s) can have a weight average molecular weight of from about 10 kDa to about 500 kDa, from about 50 kDa to about 500 kDa, from about 100 kDa to about 500 kDa, from about 200 kDa to about 500 kDa, from about 300 kDa to about 500 kDa, from about 400 kDa to about 500 kDa, from about 400 kDa to about 600 kDa, from about 400 kDa to about 700 kDa, from about 400 kDa to about 800 kDa, from about 400 kDa to about 900 kDa, from about 400 kDa to about 1,000 kDa, from about 400 kDa to about 1,200 kDa, from about 400 kDa to about 1,400 kDa, from about 400 kDa to about 1,600 kDa, from about 400 kDa to about 1,800 kDa, from about 400 kDa to about 2,000 kDa, from about 200 kDa to about 2,000 kDa, from about 500 kDa to about 2,000 kDa, or from about 800 kDa to about 2,000 kDa.

Weight average molecular weight can be determined by any suitable technique. While alternate techniques are envisioned, in some embodiments, the weight average molecular weight is determined using size exclusion chromatography (SEC) equipped with a set of TSKgel PW columns (TSKgel Guard+GMPW+GMPW+G1000PW), Tosoh Bioscience LLC, Cincinnati, Ohio) and a Waters 2414 (Waters Corporation, Milford, Mass.) refractive index detector or a DAWN HELEOS II multi-angle light scattering (MALS) detector (Wyatt Technology, Santa Barbara, Calif.). Moreover, the weight average molecular weight is determined from either calibration with polyethylene oxide/polyethylene glycol standards ranging from 150-875,000 Daltons or directly using light scattering data with known refractive index increment ("dn/dc").

In certain embodiments, the weight average molecular weight is determined by hydrolysis of the associative polymer to remove the hydrolysable side chains and then further analyzed with size exclusion chromatography (SEC). The associative polymer can be hydrolyzed by any suitable technique. For example, the associative polymer can be hydrolyzed by treatment with a 0.1 wt. % solution of NaOH at pH 12 with a cage stirrer at 400 rpm for one hour. As used herein, "hydrolysable side chains" refer to any side chain on an associative monomer unit or an additional monomer unit that can be cleaved through hydrolysis. Without wishing to be bound to any particular theory, the associative polymer, comprising an associative monomer unit, may need to be hydrolyzed prior to size exclusion chromatography due to low recovery rate from the column. Generally, hydrolysis of the associative polymer does not cleave the polymer backbone and preserves the degree of polymerization of the associative polymer.

In certain embodiments, the associative monomer unit does not contain a hydrolysable side chain. In embodiments where the associative monomer unit does not contain a hydrolysable side chain, the weight average molecular weight can be determined by analyzing a surrogate of the associative polymer. For example, the weight average molecular weight can be determined by synthesizing a polymer using the exact same formulation in the absence of the associative monomer unit. Without wishing to be bound to any particular theory, the polymer synthesized with the same formulation maintains a similar degree of polymerization and results in a weight average molecular weight similar to an associative polymer wherein the associative monomer unit is present.

Illustrative embodiments of the associative polymer(s) generally include one or more associative monomer unit(s)

and one or more additional monomer unit(s). As used herein, "additional monomer unit" refers to any monomer unit other than the associative monomer unit. In certain embodiments, the one or more additional monomer units are derived from a water-soluble monomer (e.g., acrylamide, diallyldimethylammonium chloride ("DADMAC"), 2-(acryloyloxy)-N,N,N-trimethylethanaminium chloride ("DMAEA.MCQ"), etc.). As used herein, "derived" when referring to a monomer unit, means that the monomer unit has substantially the same structure of a monomer from which it was made, wherein the terminal olefin has been transformed during the process of polymerization. In some embodiments, the associative polymer(s) include one or more associative monomer unit(s), a monomer unit derived from a monomer of Formula I, and one or more additional monomer unit(s). In certain embodiments, the associative polymer(s) include an associative monomer unit, a monomer unit derived from a monomer of Formula I, and an additional monomer unit.

In some embodiments, the one or more associative monomer unit(s), and the one or more additional monomer unit(s) can be incorporated into the associative polymer(s) using monomers, dimers, trimers, oligomers, adducts, or a combination thereof of the monomers structures from which they are derived. For example, the one or more associative monomer unit(s), or the one or more additional monomer unit(s) can exist as a dimer, trimer, oligomer, or adduct prior to incorporation into the associative polymer(s).

The associative polymer(s) can comprise any one or more suitable additional monomer unit(s) selected from a cationic monomer unit, an anionic monomer unit, a nonionic monomer unit, a zwitterionic monomer unit, and a combination of two or more thereof. For example, the associative polymer(s) can comprise a cationic monomer unit and an anionic monomer unit, an anionic monomer unit and a nonionic monomer unit, a cationic monomer unit and a nonionic monomer unit, or a cationic monomer unit, an anionic monomer unit, and a nonionic monomer unit. In certain embodiments, the associative polymer(s) comprise and/or further comprise a zwitterionic monomer unit. The associative polymer(s) can be synthesized by any suitable polymerization method. For example, the associative polymer(s) can be made through free radical polymerization, addition polymerization, free radical addition polymerization, cationic addition polymerization, anionic addition polymerization, emulsion polymerization, solution polymerization, suspension polymerization, precipitation polymerization, or a combination thereof. In certain embodiments, polymerization occurs through free radical polymerization.

Thus, a suitable additional monomer unit can be derived from any one or more suitable monomers capable of participating in free radical polymerization. For example, the associative polymer(s) can comprise one or more additional monomer units derived from a monomer selected from a monomer of Formula I, 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

In some embodiments, the associative polymer(s) comprise a monomer unit derived from a monomer of Formula I:

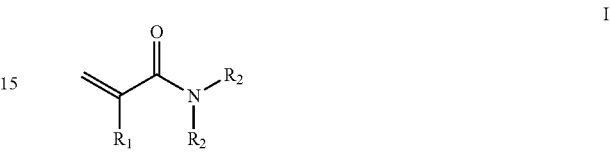

wherein $R_1$ is H or $C_1$-$C_4$ alkyl (e.g., methyl, ethyl, n-propyl, iso-propyl, n-butyl, sec-butyl, or tert-butyl) and each $R_2$ is independently H or an organic group. As used herein, the term "organic group" refers to an alkyl group, an aryl group, a fluoroalkyl group, or a fluoroaryl group. In certain embodiments, the monomer unit derived from a monomer of Formula I is considered an additional monomer unit.

In certain embodiments of the substituent $R_2$, the organic group is a $C_1$-$C_6$ alkyl group (i.e., 1, 2, 3, 4, 5, or 6 carbon units in length). In some embodiments, the $C_1$-$C_6$ alkyl group is saturated, unsaturated, branched, straight-chained, cyclic, or a combination thereof. An exemplary list of $C_1$-$C_6$ alkyl groups is methyl, ethyl, n-propyl, iso-propyl, n-butyl, sec-butyl, tert-butyl, n-pentyl, sec-pentyl, neo-pentyl, or hexyl. In certain embodiments, the $C_1$-$C_6$ alkyl group is substituted with one or more alkyl substituents, aryl substituents, heteroatoms, or combinations thereof (e.g., benzyl, phenylethyl, phenylpropyl, etc.). In some embodiments, the $C_1$-$C_6$ alkyl group can be a $C_1$-$C_6$ heteroalkyl group (i.e., 1, 2, 3, 4, 5, or 6 carbon units in length). As used herein, "heteroalkyl group" refers to a saturated or unsaturated, substituted or unsubstituted, straight-chained, branched, or cyclic aliphatic group that contains at least 1 heteroatom (e.g., O, S, N, and/or P) in the core of the molecule (i.e., the carbon backbone).

In certain embodiments of the substituent $R_2$, the organic group is an aryl group. The aryl group can be any substituted or unsubstituted aryl or heteroaryl group, wherein the heteroaryl group is an aromatic 5- or 6-membered monocyclic group that has at least one heteroatom (e.g., O, S, or N) in at least one of the rings. The heteroaryl group can contain one or two oxygen or sulfur atoms and/or from one to four nitrogen atoms, provided that the total number of heteroatoms in the ring is four or less and the ring has at least one carbon atom. Optionally, the nitrogen, oxygen, and sulfur atoms can be oxidized (i.e., has undergone a process of losing electrons), and the nitrogen atoms optionally can be quaternized. In some embodiments, the aryl compound is phenyl, pyrrolyl, furanyl, thiophenyl, pyridyl, isoxazolyl, oxazolyl, isothiazolyl, thiazolyl, imidazolyl, thiadiazolyl, tetrazolyl, triazolyl, oxadiazolyl, pyrazolyl, pyrazinyl, triazinyl, pyrimidinyl, or pyridazinyl.

In certain embodiments of the substituent $R_2$, the organic group is a $C_1$-$C_6$ fluoroalkyl group or a $C_1$-$C_6$ fluoroaryl group. As used herein, the terms "fluoroalkyl" and "fluoroaryl" refer to any alkyl group or aryl group, respectively, with one or more fluorine atoms.

In certain embodiments, the monomer of Formula I is acrylamide or methacrylamide.

The associative polymer(s) can comprise the one or more additional monomer unit(s) in any suitable concentration, so long as the associative polymer(s) include a suitable portion of one or more associative monomer unit(s) as provided herein. The associative polymer(s) can comprise a sum total of about 90 mol % or more of the one or more additional monomer unit(s), for example, about 91 mol % or more, about 92 mol % or more, about 93 mol % or more, about 94 mol % or more, about 95 mol % or more, about 96 mol % or more, about 97 mol % or more, about 98 mol % or more, or about 99 mol % or more. Alternatively, or in addition to, the associative polymer(s) can comprise a sum total of about 99.995 mol % or less of the one or more additional monomer unit(s), for example, about 99.99 mol % or less, about 99.9 mol % or less, about 99.75 mol % or less, about 99.5 mol % or less, about 99.4 mol % or less, about 99.3 mol % or less, about 99.2 mol % or less, or about 99.1 mol % or less. Thus, the associative polymer(s) can comprise the one or more additional monomer unit(s) in a sum total concentration bounded by any two of the aforementioned endpoints. The associative polymer(s) can comprise a sum total from about 90 mol % to about 99.995 mol % of the one or more additional monomer unit(s), for example, from about 91 mol % to about 99.995 mol %, from about 92 mol % to about 99.995 mol %, from about 93 mol % to about 99.995 mol %, from about 94 mol % to about 99.995 mol %, from about 95 mol % to about 99.995 mol %, from about 97 mol % to about 99.995 mol %, from about 98 mol % to about 99.995 mol %, from about 99 mol % to about 99.995 mol %, from about 99 mol % to about 99.99 mol %, from about 99 mol % to about 99.9 mol %, from about 99 mol % to about 99.75 mol %, from about 99 mol % to about 99.5 mol %, from about 99 mol % to about 99.4 mol %, from about 99 mol % to about 99.3 mol %, from about 99 mol % to about 99.2 mol %, from about 99 mol % to about 99.1 mol %, from about 99.5 mol % to about 99.99 mol %, from about 99.5 mol % to about 99.995 mol %, from about 99.75 mol % to about 99.99 mol %, or from about 99.75 mol % to about 99.995 mol %.

The associative polymer(s) can comprise one or more associative monomer unit(s) of any suitable type(s). As described herein, "associative monomer unit" refers to any monomer unit capable of coordinating with itself, other associative monomer units, surfactants, or a combination thereof. The coordination can occur through any suitable interaction. For example, the coordination can occur through ionic bonding, hydrogen bonding, hydrophobic interactions, dipolar interactions, Van der Waals forces, or a combination of two or more such coordination types.

In some embodiments, the associative monomer unit is formed post polymerization by attaching an associative moiety to a polymer. As used herein, "associative moiety" refers to any pendant chemical structure capable of coordinating with itself, other associative monomer units, surfactants, or a combination thereof. The coordination can occur through any suitable interaction. For example, the coordination can occur through ionic bonding, hydrogen bonding, hydrophobic interactions, dipolar interactions, Van der Waals forces, or a combination of two or more such coordination types. In some embodiments, the associative moiety is attached directly to the terminal end of a polymer, attached through a linker to the terminal end of a polymer, attached directly to the polymer backbone, attached to the polymer backbone through a linker, or a combination thereof.

In certain embodiments, the one or more associative monomer unit(s) of the one or more associatively networked polymer(s) are structurally similar. As used herein, "structurally similar" means that the associative monomer unit(s) have similar chemical functional groups. In some embodiments, the associative monomer unit(s) each comprise at least one hydroxyl substituent. In some embodiments, the associative monomer unit(s) each comprise at least one amine substituent. In some embodiments, the associative monomer unit(s) each comprise a polyether chain. In some embodiments, the associative monomer unit(s) each comprise a polyether chain, wherein the length of the polyether chains are separated by six carbon units or less (i.e., 6, 5, 4, 3, 2, 1, or 0). For example, if an associative monomer unit has a polyether chain length of 16 carbon units, then a structurally similar associative monomer unit will have a polyether chain length from 10-22 carbon units (i.e., 10, 11, 12, 13, 14, 15, 16, 17, 18, 19, 20, 21, or 22). In certain embodiments, the polyether chains each comprise the same number of carbon ether units. In some embodiments, the associative monomer unit(s) each comprise an alkyl chain. In some embodiments, the associative monomer unit(s) each comprise alkyl chains, wherein the length of the alkyl chains are separated by six carbon units or less (i.e., 6, 5, 4, 3, 2, 1, or 0). For example, if an associative monomer unit has an alkyl chain length of 16 carbon units, then a structurally similar associative monomer unit will have an alkyl chain length from 10-22 carbon units (i.e., 10, 11, 12, 13, 14, 15, 16, 17, 18, 19, 20, 21, or 22). In certain embodiments, the alkyl chains each comprise the same number of carbon units. In certain embodiments, the associative monomer unit(s) are the same.

In certain embodiments, the one or more associative monomer unit(s) are incorporated into the polymer through polymerization with one or more associative monomer(s). Thus, the one or more associative monomer unit(s) can be derived from any one or more suitable associative monomer(s) selected from a nonionic associative monomer, a cationic associative monomer, an anionic associative monomer, a zwitterionic associative monomer, and a combination thereof. The one or more associative monomer(s) are capable of participating in polymerization. In certain embodiments, the one or more associative monomer(s) comprise an unsaturated subunit (e.g., acrylate, acrylamide, etc.), separate from the associative moiety, capable of participating in free radical polymerization. Generally, the one or more associative monomer(s) are selected from an acrylate, an acrylamide, or a combination thereof.

In an embodiment, the associative monomer unit is a nonionic associative monomer unit. Generally, the nonionic associative monomer unit is derived from an acrylate and/or an acrylamide monomer of Formula II:

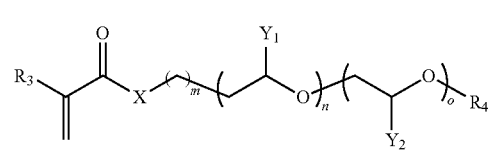

wherein $R_3$ is H or $C_1$-$C_{10}$ alkyl (e.g., $(CH_2)_k CH_3$), wherein k is an integer from 0 to 9 (i.e., 0, 1, 2, 3, 4, 5, 6, 7, 8, or 9), X is O or NH, m, n, and o are independently integers from 0 to 100, wherein when (n+o)≤3, m is at least 7, each $Y_1$ and $Y_2$ are independently H or $C_1$-$C_4$ alkyl (e.g., methyl, ethyl, n-propyl, iso-propyl, n-butyl, sec-butyl, or tert-butyl), and $R_4$ is H or a hydrophobic group. In some embodiments, "$C_1$-$C_{10}$ alkyl" refers to a branched $C_1$-$C_{10}$ alkyl group. In certain embodiments, each $Y_1$ and $Y_2$ is independently chosen to produce block or random copolymers of ethylene oxide ("EO"), propylene oxide ("PO"), or a combination thereof. In some embodiments, m, n, and o refer to an average (rounded to the nearest integer) chain length of the designated subunits (i.e., average carbon chain length or average EO/PO chain length). As used herein, the term "hydrophobic group" refers to an alkyl group, an aryl group, a fluoroalkyl group, or a fluoroaryl group.

In certain embodiments of the substituent $R_4$, the hydrophobic group is a $C_1$-$C_{32}$ alkyl group (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbon units in length). In some embodiments, the $C_1$-$C_{32}$ alkyl group is saturated, unsaturated, branched, straight-chained, cyclic, or a combination thereof. An exemplary list of $C_1$-$C_{32}$ alkyl groups is methyl, ethyl, n-propyl, iso-propyl, n-butyl, sec-butyl, tert-butyl, n-pentyl, sec-pentyl, neo-pentyl, hexyl, heptyl, octyl, nonyl, lauryl, stearyl, cetyl, behenyl, cyclopentyl, cyclohexyl, propenyl, 2-butenyl, 3-butenyl, 2-pentenyl, 3-pentenyl, or 4-pentenyl. In certain embodiments, the $C_1$-$C_{32}$ alkyl carbon group is further substituted with one or more alkyl substituents, aryl substituents, heteroatoms, or combinations thereof. In some embodiments, the $C_1$-$C_{32}$ alkyl group can be a $C_1$-$C_{32}$ heteroalkyl group (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbon units in length). As used herein, "heteroalkyl group" refers to a saturated or unsaturated, substituted or unsubstituted, straight-chained, branched, or cyclic aliphatic group that contains at least 1 heteroatom (e.g., O, S, N, and/or P) in the core of the molecule (i.e., the carbon backbone).

As used herein, the term "substituted" means that one or more hydrogens on the designated atom or group are replaced with another group provided that the designated atom's normal valence is not exceeded. For example, when the substituent is oxo (i.e., =O), then two hydrogens on the carbon atom are replaced. Combinations of substituents are permissible provided that the substitutions do not significantly adversely affect synthesis or use of the associative polymer.

In certain embodiments of the substituent $R_4$, the hydrophobic group is an aryl group. The aryl group can be any substituted or unsubstituted aryl or heteroaryl group, wherein the heteroaryl group is an aromatic 5- or 6-membered monocyclic group, 9- or 10-membered bicyclic group, or an 11- to 14-membered tricyclic group, which has at least one heteroatom (e.g., O, S, or N) in at least one of the rings. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen, oxygen, and sulfur atoms optionally can be oxidized, and the nitrogen atoms optionally can be quaternized. Heteroaryl groups that are bicyclic or tricyclic must include at least one fully aromatic ring, but the other fused ring or rings can be aromatic or non-aromatic. In some embodiments, the aryl group is phenyl, naphthyl, pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, or pyridazinyl.

In certain embodiments of the substituent $R_4$, the hydrophobic group is a $C_1$-$C_{32}$ fluoroalkyl group or a $C_1$-$C_{32}$ fluoroaryl group. As used herein, the terms "fluoroalkyl" and "fluoroaryl" refer to any alkyl group or aryl group, respectively, with one or more fluorine atoms.

In certain embodiments, the nonionic associative monomer unit is derived from an acrylate monomer comprising an acrylate head group of Formula III:

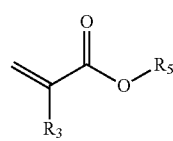

III wherein $R_5$ is —$CH_2(CH_2)_pCH_3$, $R_3$ is H or $C_1$-$C_{10}$ alkyl (e.g., $(CH_2)_kCH_3$), wherein k is an integer from 0 to 9 (i.e., 0, 1, 2, 3, 4, 5, 6, 7, 8, or 9)), and p is an integer from 3 to 100 (e.g., from 4 to 50, from 6 to 50, from 8 to 50, from 10 to 50, from 12 to 50, from 16 to 50, or from 18 to 50. In some embodiments, the acrylate monomer of Formula III is a mixture of two or more such acrylates, such that the average (rounded to the nearest integer) value of p is an integer from 3 to 100 (e.g., from 4 to 50, from 6 to 50, from 8 to 50, from 10 to 50, from 12 to 50, from 16 to 50, or from 18 to 50). In some embodiments, "$C_1$-$C_{10}$ alkyl" refers to a branched $C_1$-$C_{10}$ alkyl group. In certain embodiments, $R_5$ is a branched alkyl group from 3 to 100 carbon units in length. Generally, the nonionic associative monomer is selected from laurylacrylate, cetylacrylate, stearylacrylate, behenylacrylate, or a combination thereof. In certain embodiments, the nonionic associative monomer unit is laurylacrylate, i.e., $R_3$=H and p=10.

In certain embodiments, the nonionic associative monomer unit is derived from an acrylate monomer comprising an acrylate head group of Formula IV:

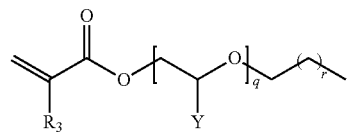

IV wherein $R_3$ is H or $C_1$-$C_{10}$ alkyl (e.g., $(CH_2)_kCH_3$), wherein k is an integer from 0 to 9 (i.e., 0, 1, 2, 3, 4, 5, 6, 7, 8, or 9), q is an integer from 2 to 100 (e.g., from 4 to 50, from 6 to 50, from 8 to 50, from 10 to 50, from 12 to 50, from 16 to 50, from 18 to 50, from 16 to 100, from 18 to 100, or from 50 to 100), r is an integer from 0 to 30 (e.g., from 2 to 30, from 4 to 30, from 6 to 30, from 8 to 30, from 10 to 30, from 12 to 30, from 16 to 30, from 18 to 30, from 20 to 30, from 22 to 30, or from 24 to 30), and each Y is independently H or $CH_3$. In some embodiments, "$C_1$-$C_{10}$ alkyl" refers to a branched $C_1$-$C_{10}$ alkyl group. In certain embodiments, each Y is independently selected to produce block or random copolymers of ethylene oxide ("EO"), propylene oxide ("PO"), or a combination thereof. In some embodiments, the acrylate monomer of Formula IV is a mixture of two or more such acrylates, such that the average (rounded to the nearest integer) value of q is an integer from 2 to 100, (e.g., from 4 to 50, from 6 to 50, from 8 to 50, from 10 to 50, from 12 to 50, from 16 to 50, from 18 to 50, from 16 to 100, from 18 to 100, or from 50 to 100), and the average (rounded to the nearest integer) value of r is an integer from 0 to 30 (e.g., from 2 to 30, from 4 to 30, from 6 to 30, from 8 to 30, from 10 to 30, from 12 to 30, from 16 to 30, from 18 to 30, from 20 to 30, from 22 to 30, or from 24 to 30). In some embodiments, the acrylate monomer of Formula IV is lauryl polyethoxy (25) methacrylate, cetyl polyethoxy (25) methacrylate, stearyl polyethoxy (25) methacrylate, behenyl polyethoxy (25) methacrylate, or a combination thereof. In certain embodiments, the nonionic associative monomer unit is a VISIOMER® ether methacrylate commercially available from Evonik Industries (Essen, Germany). In some embodiments, the nonionic associative monomer unit is cetyl and/or stearyl polyethoxy (25) methacrylic ester, marketed under the product name methacrylic ester (25 EO) C16-C18 fatty alcohol ("C18PEG1105MA"), commercially available from Evonik Industries (Essen, Germany).

In certain embodiments, the nonionic associative monomer unit is derived from an acrylate monomer comprising an acrylate head group of Formula V:

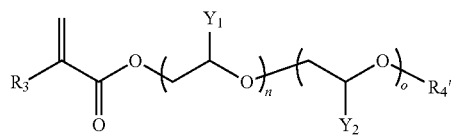

V wherein $R_3$ is H or $C_1$-$C_{10}$ alkyl (e.g., $(CH_2)_k CH_3$), wherein k is an integer from 0 to 9 (i.e., 0, 1, 2, 3, 4, 5, 6, 7, 8, or 9), each $Y_1$ and $Y_2$ are independently H or $C_1$-$C_4$ alkyl (e.g., methyl, ethyl, n-propyl, iso-propyl, n-butyl, sec-butyl, or tert-butyl), and n and o are independently integers ranging from 0 to about 100 (e.g., from about 0 to about 90, from about 0 to about 80, from about 0 to about 70, from about 0 to about 60, from about 0 to about 50, from about 10 to about 100, or from about 10 to about 50), $R_4'$ is $C_8$-$C_{30}$ alkyl group (i.e., 8, 9, 10, 11, 12, 13, 14, 15, 16, 17, 18, 19, 20, 21, 22, 23, 24, 25, 26, 27, 28, 29, or 30 carbon units in length), wherein n and o cannot both be 0. In some embodiments, "$C_1$-$C_{10}$ alkyl" refers to a branched $C_1$-$C_{10}$ alkyl group. In certain embodiments, each $Y_1$ and $Y_2$ are independently selected to produce block or random copolymers of ethylene oxide ("EO"), propylene oxide ("PO"), or a combination thereof. In some embodiments, the acrylate monomer of Formula V is a mixture of two or more such acrylates, such that the average (rounded to the nearest integer) values of n and o are independently integers from 0 to 100, (e.g., from 0 to 50, from 6 to 50, from 8 to 50, from 10 to 50, from 12 to 50, from 16 to 50, from 18 to 50, from 16 to 100, from 18 to 100, or from 50 to 100). In certain embodiments, the acrylate monomer of Formula V contains a side chain derived from a Plurafac® surfactant, commercially available from BASF Corporation (Florham Park, N.J.).

In another embodiment, the associative monomer unit is a cationic associative monomer unit. Generally, the cationic associative monomer unit is derived from an acrylate salt monomer and/or an acrylamide salt monomer of Formula VI:

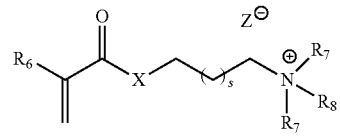

VI wherein $R_6$ and $R_7$ are each independently H or $C_1$-$C_{10}$ to alkyl (e.g., $(CH_2)_t CH_3$) wherein t is an integer from 0 to 9 (i.e., 0, 1, 2, 3, 4, 5, 6, 7, 8, or 9), X is O or NH, s is an integer from 0 to 20 (e.g., from 2 to 20, from 4 to 20, from 6 to 20, from 8 to 20, from 5 to 10, from 10 to 20, from 5 to 15, from 12 to 20, from 0 to 10, from 0 to 8, from 0 to 6, or from 0 to 4), Z is any anion, and $R_8$ is a hydrophobic group. In some embodiments, the acrylate and/or acrylamide salt of Formula VI is a mixture of two or more such acrylates and/or acrylamides, such that the average (rounded to the nearest integer) value of s is an integer from 0 to 20 (e.g., from 2 to 20, from 4 to 20, from 6 to 20, from 8 to 20, from 5 to 10, from 10 to 20, from 5 to 15, from 12 to 20, from 0 to 10, from 0 to 8, from 0 to 6, or from 0 to 4). In some embodiments, "$C_1$-$C_{10}$ alkyl" refers to a branched $C_1$-$C_{10}$ alkyl group. As used herein, the term "hydrophobic group" refers to an alkyl group, an aryl group, a fluoroalkyl group, or a fluoroaryl group.

In certain embodiments of the substituent $R_8$, the hydrophobic group is a $C_1$-$C_{32}$ alkyl group (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbon units in length). In some embodiments, the $C_1$-$C_{32}$ alkyl group is saturated, unsaturated, branched, straight-chained, cyclic, or a combination thereof. An exemplary list of $C_1$-$C_{32}$ alkyl groups is methyl, ethyl, n-propyl, iso-propyl, n-butyl, sec-butyl, tert-butyl, n-pentyl, sec-pentyl, neo-pentyl, hexyl, heptyl, octyl, nonyl, lauryl, stearyl, cetyl, behenyl, cyclopentyl, cyclohexyl, propenyl, 2-butenyl, 3-butenyl, 2-pentenyl, 3-pentenyl, or 4-pentenyl. In certain embodiments, the $C_1$-$C_{32}$ alkyl group is further substituted with one or more alkyl substituents, aryl substituents, heteroatoms, or combinations thereof. In some embodiments, the $C_1$-$C_{32}$ alkyl group can be a $C_1$-$C_{32}$ heteroalkyl group (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbon units in length). As used herein, "heteroalkyl group" refers to a saturated or unsaturated, substituted or unsubstituted, straight-chained, branched, or cyclic aliphatic chain that contains at least 1 heteroatom (e.g., O, S, N, and/or P) in the core of the molecule (i.e., the carbon backbone).

In certain embodiments of the substituent $R_8$, the hydrophobic group is an aryl group. The aryl group can be any substituted or unsubstituted aryl or heteroaryl group, wherein the heteroaryl group is an aromatic 5- or 6-membered monocyclic group, 9- or 10-membered bicyclic group, and 11- to 14-membered tricyclic group, which has at least one heteroatom (e.g., O, S, or N) in at least one of the rings. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen, oxygen, and sulfur atoms optionally can be oxidized, and the nitrogen atoms optionally can be quaternized. Heteroaryl groups that are bicyclic or tricyclic must include at least one fully aromatic ring, but the other fused ring or rings can be aromatic or non-aromatic. In some embodiments, the aryl compound is phenyl, naphthyl, pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, or pyridazinyl.

In certain embodiments of the substituent $R_8$, the hydrophobic group is a $C_1$-$C_{32}$ fluoroalkyl group or a $C_1$-$C_{32}$ fluoroaryl group. As used herein, the terms "fluoroalkyl" and "fluoroaryl" refer to any alkyl group or aryl group, respectively, with one or more fluorine atoms.

The ammonium salt of Formula VI can have any suitable anion counter ion (i.e., "Z"). In some embodiments, the anion counter ion ("Z") comprises an element selected from a halogen (e.g., fluoride, chloride, bromide, or iodide), sulfur, carbon, nitrogen, phosphorous, and a combination thereof. An exemplary list of anions comprises fluoride, chloride, bromide, iodide, sulfide, sulfite, sulfate, sulfonated, bisulfate, bisulfite, thiosulfate, carbonate, bicarbonate, nitrate, nitrite, phosphate, hydrogen phosphate, dihydrogen phosphate, phosphite, hydrogen phosphite, dihydrogen phosphite, hexafluorophosphate, carboxylate, acetate, mesylate, tosylate, or triflate. In certain embodiments, Z is selected from fluoride, chloride, bromide, mesylate, tosylate, or a combination thereof.

In certain embodiments, the cationic associative monomer unit is derived from an acrylamide salt monomer of Formula VII:

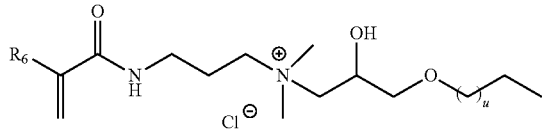

wherein $R_6$ is H or $C_1$-$C_{10}$ alkyl (e.g., $(CH_2)_tCH_3$) wherein t is an integer from 0 to 9 (i.e., 0, 1, 2, 3, 4, 5, 6, 7, 8, or 9), and u is an integer from 0 to 30 (e.g., from 2 to 30, from 4 to 30, from 6 to 30, from 8 to 30, from 5 to 25, from 10 to 30, from 12 to 30, from 15 to 25, from 16 to 30, from 18 to 30, from 20 to 30, from 22 to 30, or from 24 to 30). In some embodiments, "$C_1$-$C_{10}$ alkyl" refers to a branched $C_1$-$C_{10}$ alkyl group. In some embodiments, the acrylamide salt of Formula VII is a mixture of two or more such acrylamides, such that the average (rounded to the nearest integer) value of u is an integer from 0 to 30 (e.g., from 2 to 30, from 4 to 30, from 6 to 30, from 8 to 30, from 5 to 25, from 10 to 30, from 12 to 30, from 15 to 25, from 16 to 30, from 18 to 30, from 20 to 30, from 22 to 30, or from 24 to 30). In certain embodiments, the acrylamide salt of Formula VII is "MAPTAC-C12 derivative" (i.e., where $R_6$ is $CH_3$ and u is 10).

In another embodiment, the associative monomer unit is an anionic associative monomer unit. Generally, the anionic associative monomer unit is derived from an acrylate and/or an acrylamide monomer of Formula VIII:

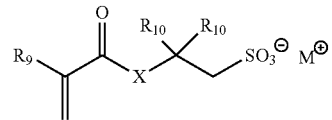

wherein $R_9$ is H or $C_1$-$C_{10}$ alkyl (e.g., $(CH_2)_vCH_3$) wherein v is an integer from 0 to 9 (i.e., 0, 1, 2, 3, 4, 5, 6, 7, 8, or 9), X is O or NH, M is any cation, and each $R_{10}$ is independently H or a hydrophobic group. In some embodiments, "$C_1$-$C_{10}$ alkyl" refers to a branched $C_1$-$C_{10}$ alkyl group. As used herein, the term "hydrophobic group" refers to an alkyl group, an aryl group, a fluoroalkyl group, or a fluoroaryl group.

In certain embodiments of the substituent $R_{10}$, the hydrophobic group is a $C_1$-$C_{32}$ alkyl group (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbon units in length). In some embodiments, the $C_1$-$C_{32}$ alkyl group is saturated, unsaturated, branched, straight-chained, cyclic, or a combination thereof. An exemplary list of $C_1$-$C_{32}$ alkyl groups is methyl, ethyl, n-propyl, iso-propyl, n-butyl, sec-butyl, tert-butyl, n-pentyl, sec-pentyl, neo-pentyl, hexyl, heptyl, octyl, nonyl, lauryl, stearyl, cetyl, behenyl, cyclopentyl, cyclohexyl, propenyl, 2-butenyl, 3-butenyl, 2-pentenyl, 3-pentenyl, or 4-pentenyl. In certain embodiments, the $C_1$-$C_{32}$ alkyl group is further substituted with one or more alkyl substituents, aryl substituents, heteroatoms, or combinations thereof. In some embodiments, the $C_1$-$C_{32}$ alkyl group can be a $C_1$-$C_{32}$ heteroalkyl group (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 carbon units in length). As used herein, "heteroalkyl group" refers to a saturated or unsaturated, substituted or unsubstituted, straight-chained, branched, or cyclic aliphatic group that contains at least 1 heteroatom (e.g., O, S, N, and/or P) in the core of the molecule (i.e., the carbon backbone).

In certain embodiments of the substituent $R_{10}$, the hydrophobic group is an aryl group. The aryl group can be any substituted or unsubstituted aryl or heteroaryl group, wherein the heteroaryl group is an aromatic 5- or 6-membered monocyclic group, 9- or 10-membered bicyclic group, and 11- to 14-membered tricyclic group, which has at least one heteroatom (e.g., O, S, or N) in at least one of the rings. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen, oxygen, and sulfur atoms optionally can be oxidized, and the nitrogen atoms optionally can be quaternized. Heteroaryl groups that are bicyclic or tricyclic must include at least one fully aromatic ring, but the other fused ring or rings can be aromatic or non-aromatic. In some embodiments, the aryl compound is phenyl, naphthyl, pyrrolyl, isoindolyl, indolizinyl, indolyl, furanyl, benzofuranyl, benzothiophenyl, thiophenyl, pyridyl, acridinyl, naphthyridinyl, quinolinyl, isoquinolinyl, isoxazolyl, oxazolyl, benzoxazolyl, isothiazolyl, thiazolyl, benzthiazolyl, imidazolyl, thiadiazolyl, tetrazolyl, triazolyl, oxadiazolyl, benzimidazolyl, purinyl, pyrazolyl, pyrazinyl, pteridinyl, quinoxalinyl, phthalazinyl, quinazolinyl, triazinyl, phenazinyl, cinnolinyl, pyrimidinyl, or pyridazinyl.

In certain embodiments of the substituent $R_{10}$, the hydrophobic group is a $C_1$-$C_{32}$ fluoroalkyl group or a $C_1$-$C_{32}$ fluoroaryl group. As used herein, the terms "fluoroalkyl" and "fluoroaryl" refer to any alkyl group or aryl group, respectively, with one or more fluorine atoms.

The sulfonate salt can have any suitable cation counter ion (i.e., "M"). For example, the cation counter ion ("M") can be a proton, ammonium, a quaternary amine, a cation of an alkali metal, a cation of an alkaline earth metal, a cation of a transition metal, a cation of a rare-earth metal, a main group element cation, or a combination thereof. In some embodiments, the cation counter ion is a proton or a cation of lithium, sodium, potassium, magnesium, calcium, manganese, iron, zinc, or a combination thereof. In certain embodiments, M is selected from hydrogen, lithium, sodium, potassium, or a combination thereof.

The one or more associative monomer unit(s) can be present in the associative polymer in any suitable amount. The associative polymer can comprise a sum total of about 10 mol % or less of the one or more associative monomer unit(s), for example, about 9 mol % or less, about 8 mol % or less, about 7 mol % or less, about 6 mol % or less, about 5 mol % or less, about 4 mol % or less, about 3 mol % or less, about 2 mol % or less, or about 1 mol % or less. Alternatively, or in addition to, the associative polymer can comprise about 0.005 mol % or more of the one or more associative monomer unit(s), for example, about 0.01 mol % or more, about 0.1 mol % or more, about 0.25 mol % or more, about 0.3 mol % or more, about 0.4 mol % or more, or about 0.5 mol % or more. Thus, the associative polymer can comprise the one or more associative monomer unit(s) in a concentration bounded by any two of the aforementioned endpoints. The associative polymer can comprise from about 0.005 mol % to about 10 mol % of the one or more associative monomer unit(s), for example, from about 0.005 mol % to about 9 mol %, from about 0.005 mol % to about 8 mol %, from about 0.005 mol % to about 7 mol %, from about 0.005 mol % to about 6 mol %, from about 0.005 mol % to about 5 mol %, from about 0.005 mol % to about 4 mol %, from about 0.005 mol % to about 3 mol %, from about 0.005 mol % to about 2 mol %, from about 0.005 mol % to about 1 mol %, from about 0.01 mol % to about 1 mol %, from about 0.1 mol % to about 1 mol %, from about 0.25 mol % to about 1 mol %, from about 0.3 mol % to about 1 mol %, from about 0.4 mol % to about 1 mol %, from about 0.5 mol % to about 1.0 mol %, from about 0.01 mol % to about 0.5 mol %, or from about 0.01 mol % to about 0.25 mol %.

In some embodiments, the associative polymer comprises an associative monomer unit derived from a monomer of Formula II, a monomer unit derived from a monomer of Formula I, and an additional cationic monomer unit. In some embodiments, the associative polymer comprises an associative monomer unit derived from a monomer of Formula II, a monomer unit derived from a monomer of Formula I, and an additional monomer unit derived from DMAEA.MCQ. In some embodiments, the associative polymer comprises an associative monomer unit derived from a monomer of Formula II, an additional monomer unit derived from acrylamide, and an additional monomer unit derived from DMAEA.MCQ. In certain embodiments, the associative polymer comprises an associative monomer unit derived from VISIOMER® monomer C18PEG1105MA, an additional monomer unit derived from acrylamide, and an additional monomer unit derived from DMAEA.MCQ.

In some embodiments, the associative polymer comprises an associative monomer unit derived from a monomer of Formula II, a monomer unit derived from a monomer of Formula I, and an additional anionic monomer unit. In some embodiments, the associative polymer comprises an associative monomer unit derived from a monomer of Formula II, a monomer unit derived from a monomer of Formula I, and an additional monomer unit derived from sodium acrylate. In some embodiments, the associative polymer comprises an associative monomer unit derived from a monomer of Formula II, an additional monomer unit derived from acrylamide, and an additional monomer unit derived from sodium acrylate. In certain embodiments, the associative polymer comprises an associative monomer unit derived from VISIOMER® monomer C18PEG1105MA, an additional monomer unit derived from acrylamide, and an additional monomer unit derived from sodium acrylate.

In some embodiments, the associative polymer comprises an associative monomer unit derived from a monomer of Formula VI, a monomer unit derived from a monomer of Formula I, and an additional cationic monomer unit. In some embodiments, the associative polymer comprises an associative monomer unit derived from a monomer of Formula VI, a monomer unit derived from a monomer of Formula I, and an additional monomer unit derived from DMAEA.MCQ. In some embodiments, the associative polymer comprises an associative monomer unit derived from a monomer of Formula VI, an additional monomer unit derived from acrylamide, and an additional monomer unit derived from DMAEA.MCQ. In certain embodiments, the associative polymer comprises an associative monomer unit derived from MAPTAC-C12 derivative of Formula VII, an additional monomer unit derived from acrylamide, and an additional monomer unit derived from DMAEA.MCQ.

In some embodiments, the associative polymer comprises an associative monomer unit derived from a monomer of Formula VI, a monomer unit derived from a monomer of Formula I, and an additional anionic monomer unit. In some embodiments, the associative polymer comprises an associative monomer unit derived from a monomer of Formula VI, a monomer unit derived from a monomer of Formula I, and an additional monomer unit derived from sodium acrylate. In some embodiments, the associative polymer comprises an associative monomer unit derived from a monomer of Formula VI, an additional monomer unit derived from acrylamide, and an additional monomer unit derived from sodium acrylate. In certain embodiments, the associative polymer comprises an associative monomer unit derived from MAPTAC-C12 derivative of Formula VII, an additional monomer unit derived from acrylamide, and an additional monomer unit derived from sodium acrylate.

In some embodiments, the associative polymer comprises an associative monomer unit derived from a monomer of Formula VIII, a monomer unit derived from a monomer of Formula I, and an additional cationic monomer unit. In some embodiments, the associative polymer comprises an associative monomer unit derived from a monomer of Formula VIII, a monomer unit derived from a monomer of Formula I, and an additional monomer unit derived from DMAEA.MCQ.

In some embodiments, the associative polymer comprises an associative monomer unit derived from a monomer of Formula VIII, a monomer unit derived from a monomer of Formula I, and an additional anionic monomer unit. In some embodiments, the associative polymer comprises an associative monomer unit derived from a monomer of Formula VIII, a monomer unit derived from a monomer of Formula I, and an additional monomer unit derived from sodium acrylate.

Also provided is an associative polymer of Formula $AP_1$:

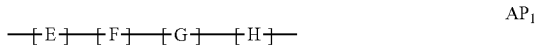

$$AP_1$$

wherein E is one or more associative monomer unit(s), F is one or more additional monomer unit(s), G is one or more monomer unit(s) derived from a monomer of Formula I, H is optionally present and is one or more piperidine-2,6-dione unit(s), wherein the one or more piperidine-2,6-dione(s) are formed upon cyclization of an acrylamide nitrogen of the monomer unit derived from the monomer of Formula I ("G") on a carbonyl of the additional monomer unit ("F"), wherein the associative polymer has a weight average molecular weight of from about 10 kDa to about 2,000 kDa.

In some embodiments, the associative polymer is of formula $AP_2$:

$$AP_2$$

wherein E is one or more associative monomer unit(s), E' is a mole percentage value of from about 0.005 to about 10, F is one or more additional monomer unit(s), F' is a mole percentage value of from about 0.005 to about 90, G is one or more monomer unit(s) derived from a monomer of Formula I, and G' is a mole percentage value of from about 10 to about 99.99. Monomer unit E is defined by the associative monomer units described herein. Monomer units F and G are defined by the additional monomer units and monomer units derived from the monomer of Formula I, respectively, described herein.

As described herein, the associative polymer of formula $AP_2$ can exist as an alternating polymer, random polymer, block polymer, graft polymer, linear polymer, branched polymer, cyclic polymer, or a combination thereof. Thus, E, F, and G can exist in any suitable order (e.g., EGF, EFG, GEF, GFE, FEG, or FGE), including repeating individual units (e.g., EEFFFGG, EFGGEFEE, EFGEEE, EEEEFG, etc.).

The amount of one or more associative monomer unit(s) ("E'"), and the sum total of one or more additional monomer unit(s) ("F'"+"G'") are as described previously for the one or more associative monomer unit(s) and the sum total of one or more additional monomer unit(s).

In some embodiments, the associative polymer of formula $AP_2$ undergoes charge degradation to provide an associative polymer of formula $AP_3$:

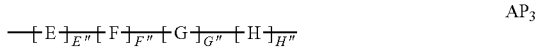

$$AP_3$$

wherein E is one or more associative monomer unit(s), E" is a mole percentage value of from about 0.005 to about 10, F is one or more additional monomer unit(s), F" is a mole percentage value of from about 0.005 to about 90, G is one or more monomer unit(s) derived from a monomer of Formula I, G" is a mole percentage value of from about 10 to about 99.99, H is one or more piperidine-2,6-dione unit(s), wherein the one or more piperidine-2,6-dione(s) are formed upon cyclization of an acrylamide nitrogen of the monomer unit derived from a monomer of Formula I ("G") on a carbonyl of the additional monomer unit ("F"), and H" is a mole percentage value of from about 0 (i.e., trace amounts) to about 10. As used herein, "charge degradation" refers to the process of a monomer unit derived from a monomer of Formula I cyclizing on a charged additional monomer unit (i.e., a cationic and/or anionic monomer unit), such that the charged substituent of the additional monomer unit is displaced, and thus, the polymer has less cationic monomer units and/or less anionic monomer units. Without wishing to be bound by any particular theory, it is believed that the charge degradation can occur spontaneously, or can be facilitated by one or more components in the polymer solution.

In certain embodiments, the associative polymer is of formula $AP_3$:

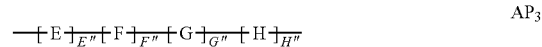

$$AP_3$$

wherein E is one or more associative monomer unit(s), E" is a mole percentage value of from about 0.005 to about 10, F is one or more additional monomer unit(s), F" is a mole percentage value of from about 0.005 to about 90, G is one or more monomer unit(s) derived from a monomer of Formula I, G" is a mole percentage value of from about 10 to about 99.99, H is one or more units of the formula

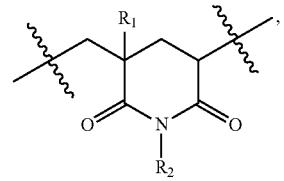

wherein $R_1$ is H or $C_1$-$C_4$ alkyl (e.g., methyl, ethyl, n-propyl, iso-propyl, n-butyl, sec-butyl, or tert-butyl) and $R_2$ is H or an organic group, and H" is a mole percentage value of from about 0 (i.e., trace amounts) to about 10. In certain embodiments, $R_1$ and $R_2$ are hydrogen.

As described herein, the associative polymer of formula $AP_3$ can exist as an alternating polymer, random polymer, block polymer, graft polymer, linear polymer, branched polymer, cyclic polymer, or a combination thereof. Thus, E, F, G, and H can exist in any suitable order (e.g., EGFH, EGHF, EHFG, EHGF, EFGH, EFHG, FEGH, FEHG, FHEG, FHGE, FGEH, FGHE, GHFE, GHEF, GEFH, GEHF, GFHE, GFEH, HEFG, HEGF, HGEF, HGFE, HFEG, or HFGE), including repeating individual units (e.g., EEFFFGGHHH, EFGGEFEEH, EFGEEEHH, HHHEEEEFG, etc.).

In certain embodiments, the associative polymer is of formula $AP_4$:

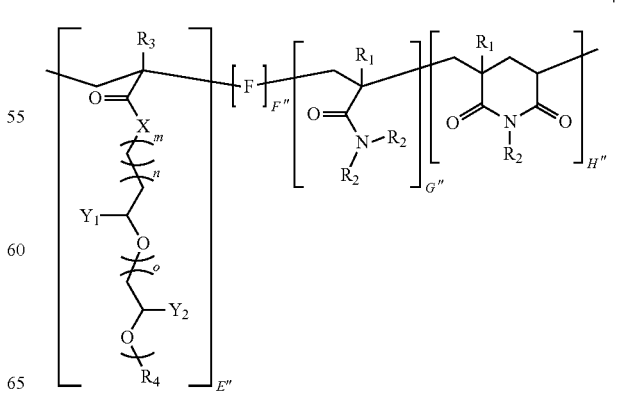

$$AP_4$$

wherein each $R_1$ is independently H or $C_1$-$C_4$ alkyl (e.g., methyl, ethyl, n-propyl, iso-propyl, n-butyl, sec-butyl, or tert-butyl), each $R_2$ is independently H or an organic group, $R_3$ is H or $C_1$-$C_{10}$ alkyl (e.g., $(CH_2)_k CH_3$), wherein k is an integer from 0 to 9 (i.e., 0, 1, 2, 3, 4, 5, 6, 7, 8, or 9), X is O or NH, m, n, and o are independently integers from 0 to 100, wherein when (n+o)≤3, m is at least 7, each $Y_1$ and $Y_2$ are independently H or $C_1$-$C_4$ alkyl (e.g., methyl, ethyl, n-propyl, iso-propyl, n-butyl, sec-butyl, or tert-butyl), and $R_4$ is H or a hydrophobic group, E" is a mole percentage value of from about 0.005 to about 10, F is one or more additional monomer unit(s), F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

In certain embodiments of the associative polymer of formula $AP_4$, F is derived from a diallyldimethylammonium chloride ("DADMAC") monomer. In certain embodiments of the associative polymer of formula $AP_4$, F is derived from a 2-(acryloyloxy)-N,N,N-trimethylethanaminium chloride ("DMAEA.MCQ") monomer.

In certain embodiments, the associative polymer is of formula $AP_5$:

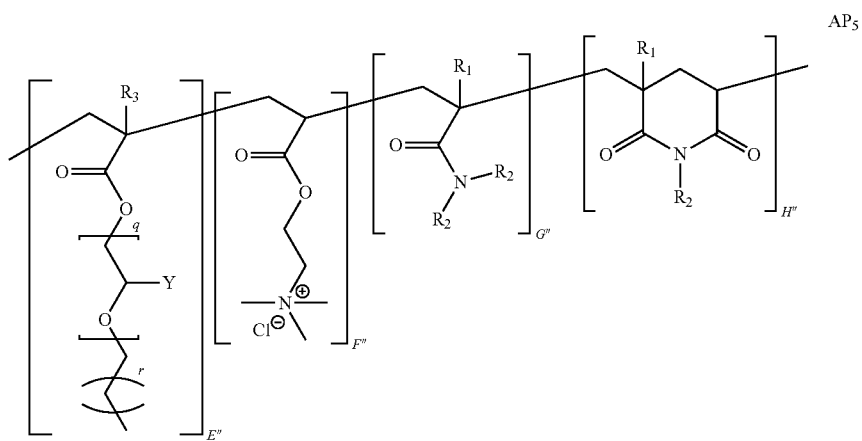

wherein each $R_1$ is independently H or $C_1$-$C_4$ alkyl (e.g., methyl, ethyl, n-propyl, iso-propyl, n-butyl, sec-butyl, or tert-butyl), each $R_2$ is independently H or an organic group, $R_3$ is H or $C_1$-$C_{10}$ alkyl (e.g., $(CH_2)_k CH_3$), wherein k is an integer from 0 to 9, q is an integer from 2 to 100, r is an integer from 0 to 30, each Y is independently H or $CH_3$, E" is a mole percentage value of from about 0.005 to about 10, F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

In certain embodiments, the associative polymer is of formula $AP_6$:

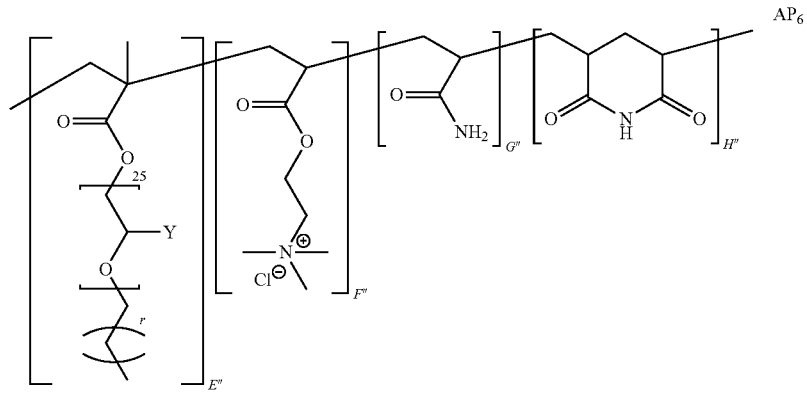

wherein r is an integer from 0 to 30 (e.g., from 2 to 30, from 4 to 30, from 6 to 30, from 8 to 30, from 10 to 30, from 12 to 30, from 16 to 30, from 18 to 30, from 20 to 30, from 22 to 30, or from 24 to 30), each Y is independently H or $CH_3$, E" is a mole percentage value of from about 0.005 to about 10, F" is a mole percentage value of from about 0.005 to about 90, G" is a mole percentage value of from about 10 to about 99.99, and H" is a mole percentage value of from about 0 (i.e., trace amounts) to about 10. In certain embodiments, r is an integer from 14 to 16.

In certain embodiments, the associative polymer is of formula $AP_7$:

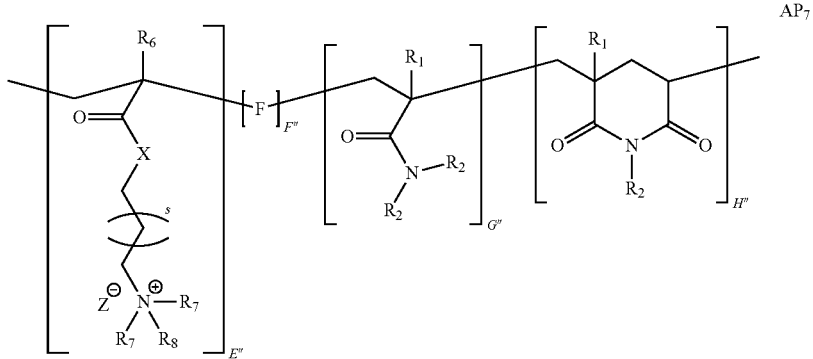

wherein each $R_1$ is independently H or $C_1$-$C_4$ alkyl (e.g., methyl, ethyl, n-propyl, iso-propyl, n-butyl, sec-butyl, or tert-butyl), each $R_2$ is independently H or an organic group, $R_6$ and $R_7$ are each independently H or $C_1$-$C_{10}$ alkyl (e.g., $(CH_2)_tCH_3$) wherein t is an integer from 0 to 9, X is O or NH, s is an integer from 0 to 20, Z is any anion, and $R_8$ is a hydrophobic group, E" is a mole percentage value of from about 0.005 to about 10, F is one or more additional monomer unit(s), F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

In certain embodiments, the associative polymer is of formula $AP_8$:

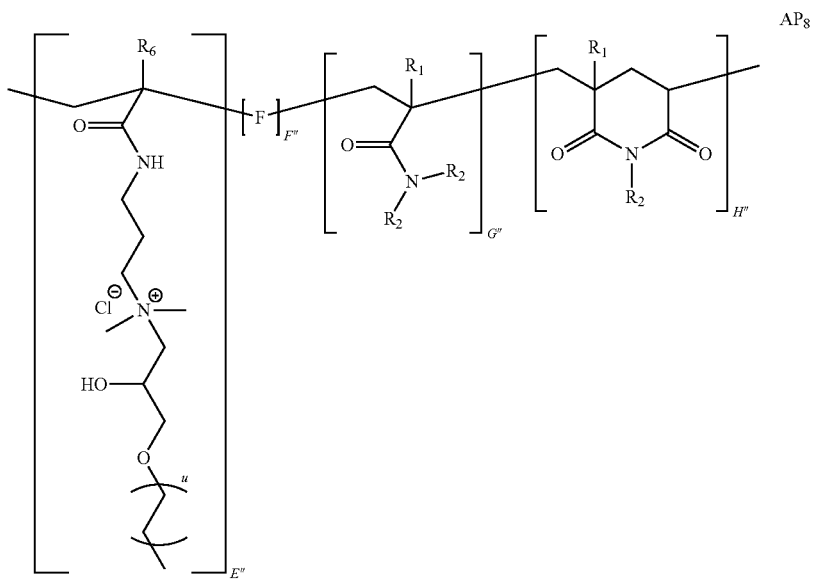

wherein each $R_1$ is independently H or $C_1$-$C_4$ alkyl (e.g., methyl, ethyl, n-propyl, iso-propyl, n-butyl, sec-butyl, or tert-butyl), each $R_2$ is independently H or an organic group, $R_6$ is H or $C_1$-$C_{10}$ alkyl (e.g., $(CH_2)_tCH_3$) wherein t is an integer from 0 to 9, and u is an integer from 0 to 30, E" is a mole percentage value of from about 0.005 to about 10, F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

In certain embodiments, the associative polymer is of formula $AP_9$:

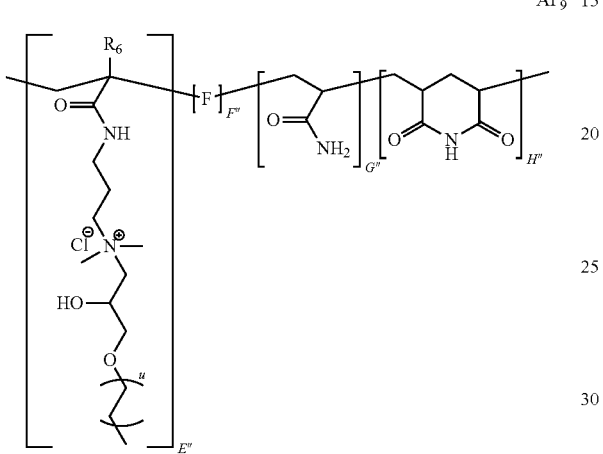

wherein $R_6$ is H or $C_1$-$C_{10}$ alkyl (e.g., $(CH_2)_tCH_3$) wherein t is an integer from 0 to 9, and u is an integer from 0 to 30, E" is a mole percentage value of from about 0.005 to about 10, F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

In certain embodiments of the associative polymers of formula $AP_{7-9}$ (i.e., $AP_7$, $AP_8$, or $AP_9$), F is derived from one or more monomers selected from acrylic acid, methacrylic acid, or salts thereof.

In certain embodiments, the associative polymer is of formula $AP_{10}$:

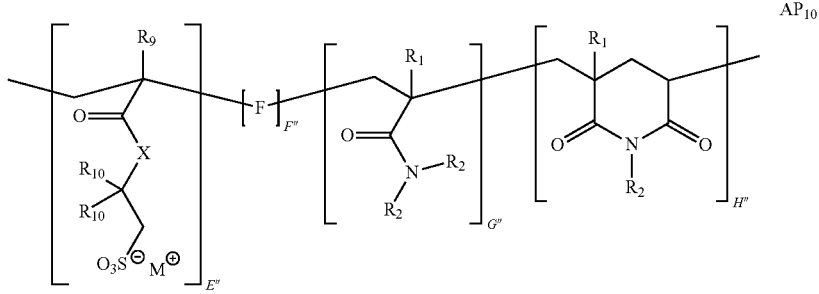

wherein each $R_1$ is independently H or $C_1$-$C_4$ alkyl (e.g., methyl, ethyl, n-propyl, iso-propyl, n-butyl, sec-butyl, or tert-butyl), each $R_2$ is independently H or an organic group, $R_9$ is H or $C_1$-$C_{10}$ alkyl (e.g., $(CH_2)_vCH_3$) wherein v is an integer from 0 to 9, X is O or NH, M is any cation, and each $R_{10}$ is independently H or a hydrophobic group, E" is a mole percentage value of from about 0.005 to about 10, F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

In certain embodiments, the associative polymer is of formula $AP_{11}$:

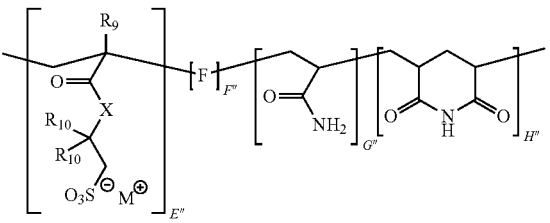

wherein $R_9$ is H or $C_1$-$C_{10}$ alkyl (e.g., $(CH_2)_vCH_3$) wherein v is an integer from 0 to 9, X is O or NH, M is any cation, and each $R_{10}$ is independently H or a hydrophobic group, E" is a mole percentage value of from about 0.005 to about 10, F is one or more additional monomer unit(s), F" is a mole percentage value of from about 0.005 to about 90, G" is a mole percentage value of from about 10 to about 99.99, and H" is a mole percentage value of from about 0 (i.e., trace amounts) to about 10. In some embodiments, "$C_1$-$C_{10}$ alkyl" refers to a branched $C_1$-$C_{10}$ alkyl group.

As described herein, the associative polymers of formula $AP_4$-$AP_{11}$ (i.e., $AP_4$, $AP_5$, $AP_6$, $AP_7$, $AP_8$, $AP_9$, $AP_{10}$, or $AP_{11}$) can exist as an alternating polymer, random polymer, block polymer, graft polymer, linear polymer, branched polymer, cyclic polymer, or a combination thereof. Thus, the monomer units can exist in any suitable order, including repeating individual units.

The presence of the monomer unit H can be detected by any suitable method. In some embodiments, monomer H is detected by $^{13}$CNMR, $^1$H NMR, IR spectroscopy, or a combination thereof.

The abundance of the monomer unit H can be determined by any suitable method. In some embodiments, the abundance of the monomer unit H can be determined by relative comparison of the peak integrations of a $^{13}$CNMR spectrum, $^1$HNMR spectrum, IR spectrum, or a combination thereof.

In some embodiments of the associative polymers of formula $AP_{3-11}$ (i.e., $AP_3$, $AP_4$, $AP_5$, $AP_6$, $AP_7$, $AP_8$, $AP_9$, $AP_{10}$, or $AP_{11}$), E" is from about 0.005 mol % to about 10 mol % (e.g., from about 0.005 mol % to about 9 mol %, from about 0.005 mol % to about 8 mol %, from about 0.005 mol % to about 7 mol %, from about 0.005 mol % to about 6 mol %, from about 0.005 mol % to about 5 mol %, from about 0.005 mol % to about 4 mol %, from about 0.005 mol % to about 3 mol %, or from about 0.005 mol % to about 2 mol %), F''' is from about 0.005 mol % to about 90 mol % (e.g., from about 0.005 mol % to about 80 mol %, from about 0.005 mol % to about 70 mol %, from about 0.005 mol % to about 60 mol %, from about 0.005 mol % to about 50 mol %, from about 0.005 mol % to about 40 mol %, from about 0.005 mol % to about 35 mol %, from about 0.005 mol % to about 30 mol %, from about 0.005 mol % to about 25 mol %, from about 0.005 mol % to about 20 mol %, from about 0.005 mol % to about 16 mol %, from about 0.005 mol % to about 12 mol %, from about 0.005 mol % to about 10 mol %, from about 2 mol % to about 20 mol %, from about 4 mol % to about 20 mol %, from about 6 mol % to about 20 mol %, from about 4 mol % to about 16 mol %, from about 4 mol % to about 12 mol %, or from about 4 mol % to about 10 mol %), G''' is from about 10 mol % to about 99.99 mol % (e.g., from about 10 mol % to about 99.99 mol %, from about 20 mol % to about 99.99 mol %, from about 30 mol % to about 99.99 mol %, from about 40 mol % to about 99.99 mol %, from about 50 mol % to about 99.99 mol %, from about 60 mol % to about 99.99 mol %, from about 70 mol % to about 99.99 mol %, from about 80 mol % to about 99.99 mol %, from about 80 mol % to about 99.95 mol %, from about 80 mol % to about 99.9 mol %, from about 80 mol % to about 99.5 mol %, from about 80 mol % to about 99 mol %, from about 80 mol % to about 97 mol %, from about 80 mol % to about 95 mol %, from about 80 mol % to about 92 mol %, from about 80 mol % to about 90 mol %, from about 84 mol % to about 99 mol %, from about 84 mol % to about 94 mol %, from about 84 mol % to about 95 mol %, from about 84 mol % to about 92 mol %, or from about 84 mol % to about 90 mol %), and H''' is from about 0 mol % (i.e., trace amounts) to about 10 mol % (e.g., from about 0.001 mol % to about 10 mol %, from about 0.001 mol % to about 9 mol %, from about 0.001 mol % to about 8 mol %, from about 0.001 mol % to about 7 mol %, from about 0.001 mol % to about 6 mol %, from about 0.001 mol % to about 5 mol %, from about 0.001 mol % to about 4 mol %, from about 0.001 mol % to about 3 mol %, or from about 0.001 mol % to about 2 mol %).

In certain embodiments of the associative polymers of formula ($AP_{3-11}$) (i.e., $AP_3$, $AP_4$, $AP_5$, $AP_6$, $AP_7$, $AP_8$, $AP_9$, $AP_{10}$, or $AP_{11}$), E''' is from about 0.005 mol % to about 1 mol % (e.g., from about 0.01 mol % to about 1 mol %, from about 0.1 mol % to about 1 mol %, from about 0.25 mol % to about 1 mol %, from about 0.3 mol % to about 1 mol %, from about 0.4 mol % to about 1 mol %, from about 0.5 mol % to about 1.0 mol %, from about 0.01 mol % to about 0.5 mol %, or from about 0.01 mol % to about 0.25 mol %), F''' is from about 4 mol % to about 10 mol % (e.g., from about 4 mol % to about 9 mol %, from about 4 mol % to about 8 mol %, from about 4 mol % to about 7 mol %, from about 4 mol % to about 6 mol %, from about 4 mol % to about 5 mol %, from about 5 mol % to about 10 mol %, from about 6 mol % to about 10 mol %, from about 7 mol % to about 10 mol %, from about 8 mol % to about 10 mol %, from about 9 mol % to about 10 mol %, or from about 6 mol % to about 8 mol %), G''' is from about 84 mol % to about 90 mol % (e.g., from about 85 mol % to about 90 mol %, from about 86 mol % to about 90 mol %, from about 87 mol % to about 90 mol %, from about 88 mol % to about 90 mol %, from about 89 mol % to about 90 mol %, from about 84 mol % to about 89 mol %, from about 84 mol % to about 88 mol %, from about 84 mol % to about 87 mol %, from about 84 mol % to about 86 mol %, from about 84 mol % to about 85 mol %, or from about 86 mol % to about 88 mol %), and H''' is from about 0 mol % (i.e., trace amounts) to about 6 mol % (e.g., from about 0.001 mol % to about 5 mol %, from about 0.001 mol % to about 4 mol %, from about 0.001 mol % to about 3 mol %, or from about 0.001 mol % to about 2 mol %, from about 0.001 mol % to about 1 mol %, from about 0.01 mol % to about 1 mol %, from about 0.1 mol % to about 1 mol %, from about 0.25 mol % to about 1 mol %, from about 0.3 mol % to about 1 mol %, from about 0.4 mol % to about 1 mol %, from about 0.5 mol % to about 1.0 mol %, from about 0.01 mol % to about 0.5 mol %, or from about 0.01 mol % to about 0.25 mol %).

The processes provided herein comprise networking one or more associative polymer(s). As used herein, "networking" refers to chemical coordination of one polymer chain to an adjacent polymer chain to promote a different physical property. The networking technique can comprise any suitable chemical coordination. Generally, the networking of one or more associative polymer(s) does not comprise covalently linking adjacent polymer chains. For example, the chemical coordination can occur through ionic bonding, hydrogen bonding, hydrophobic interactions, dipolar interactions, Van der Waals forces, or a combination thereof.

In an embodiment, at least a portion of the networking occurs between the associative monomer units of different polymer chains (i.e., intermolecular interactions). Without wishing to be bound by any particular theory, it is believed that associative monomer units interact momentarily through weak chemical interactions (i.e., ionic bonding, hydrogen bonding, hydrophobic interactions, dipolar interactions, Van der Waals forces, or a combination thereof), resulting in networking adjacent associative polymer(s) temporarily. As used herein, "networking adjacent associative polymer(s) temporarily" refers to an interaction, which can be controlled by the level of dilution, the presence of a surfactant, or a combination thereof. Thus, the networking of associative polymer(s) is reversible, thereby allowing for powders, gels, or low viscosity liquid media to be prepared and/or subsequently dispersed in a solvent.

In another embodiment, at least a portion of the networking occurs between the associative monomer units and one or more surfactant(s). Without wishing to be bound by any particular theory, it is believed that associative monomer units can interact momentarily through weak chemical interactions (i.e., ionic bonding, hydrogen bonding, hydrophobic interactions, dipolar interactions, Van der Waals forces, or a combination thereof) with the one or more surfactant(s), resulting in networking the associative polymer(s) and surfactant(s) temporarily. As used herein, "networking adjacent associative polymer(s) and surfactant(s) temporarily" refers to an interaction, which can be controlled by the level of dilution, the amount of a surfactant, or a combination thereof. Thus, the networking of associative polymer(s) and surfactant(s) is reversible, and allows for powder, gels, or low viscosity liquid media to be prepared and/or subsequently dispersed in a solvent.

In some embodiments, at least a portion of the networking occurs through micellar copolymerization. As used herein, "micellar copolymerization" refers to concurrent formation of micelles comprising associative monomers and/or surfactant(s), and associative polymer(s) comprising associative monomer units. Without wishing to be bound by any particular theory, it is believed that associative monomer units of adjacent polymers can become incorporated into micelles formed from associative monomers and/or surfactant(s), thereby networking the adjacent associative polymer(s) polymers temporarily.

As used herein, "temporary networking" refers to an associative interaction (e.g., within the solution of associative polymer(s), the wet gel, and the powder) which can be controlled by the level of dilution, the presence of a surfactant, or a combination thereof. Contrary to more permanent cross-linking practice known in the art, e.g., cross-linking via covalent bonds, temporary networking can be momentary. As used herein, "temporary" can refer to any length of time extending from the initial formation of the solution of associative polymers to dispersion of the powder in solution. For example, temporary networking provides sufficient structure of the wet gel to allow for machine processing and conversion into a powder. In addition, temporary networking helps to produce a powder that is stable yet maintains reasonable levels of water solubility. Upon dilution in water, the associative interactions (i.e., the temporary networking) decrease, and the powder becomes dispersed in the water or other solvent.

In certain embodiments, the process comprises networking one or more associative polymer(s) and one or more surfactant(s) wherein the one or more associative monomer unit(s) and the one or more surfactant(s) are structurally similar. As used herein, "structurally similar" means that the associative monomer unit(s) and the surfactant(s) have the same or similar chemical functional groups. In some embodiments, the associative monomer unit(s) and the surfactant(s) each comprise at least one hydroxyl substituent. In some embodiments, the associative monomer unit(s) and the surfactant(s) each comprise at least one amine substituent. In some embodiments, the associative monomer unit(s) and the surfactant(s) each comprise a polyether ether chain. In some embodiments, the associative monomer unit(s) and the surfactant(s) each comprise a polyether chain, wherein the length of the polyether chains are separated by six carbon units or less (i.e., 6, 5, 4, 3, 2, 1, or 0). For example, if an associative monomer unit has a polyether chain length of 16 carbon units, then a structurally similar surfactant will have a polyether chain length from 10-22 carbon units (i.e., 10, 11, 12, 13, 14, 15, 16, 17, 18, 19, 20, 21, or 22). In certain embodiments, the polyether chains comprise the same number of carbon units. In some embodiments, the associative monomer unit(s) and the surfactant(s) each comprise an alkyl chain. In some embodiments, the associative monomer unit(s) and the surfactant(s) each comprise alkyl chains, wherein the length of the alkyl chains are separated by six carbon units or less (i.e., 6, 5, 4, 3, 2, 1, or 0). For example, if an associative monomer unit has an alkyl chain length of 16 carbon units, then a structurally similar surfactant will have an alkyl chain length from 10-22 carbon units (i.e., 10, 11, 12, 13, 14, 15, 16, 17, 18, 19, 20, 21, or 22). In certain embodiments, the alkyl chains each comprise the same number of carbons. In certain embodiments, the associative monomer unit(s) and the surfactant(s) comprise the same structural subunit.

In some embodiments, the process for making the powder further comprises one or more surfactant(s). The surfactant can be any suitable surfactant selected from an anionic surfactant, a cationic surfactant, a nonionic surfactant, and a combination thereof. In some embodiments, the one or more surfactant(s) may exist as a dimer. For example, the surfactant can have one polar head group and two non-polar tails, or two polar head groups and one non-polar tail, or two polar head groups and two non-polar tails. Without wishing to be bound to any particular theory, it is believed that the surfactant helps to provide structure to the wet gel and increases solubility of the resulting powder upon dilution in water or other solvent.

In an embodiment, the surfactant is a cationic surfactant. In certain embodiments, the cationic surfactant is an ammonium salt of Formula IX:

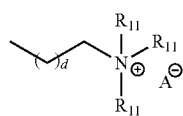

IX wherein each $R_{11}$ is independently H or $C_1$-$C_{10}$ alkyl (e.g., $(CH_2)_e CH_3$) wherein e is an integer from 0 to 9 (i.e., 0, 1, 2, 3, 4, 5, 6, 7, 8, or 9), A is any anion, and d is an integer from 6 to 34 (e.g., from 6 to 30, from 6 to 24, from 6 to 20, from 6 to 16, from 6 to 12, from 5 to 25, from 10 to 20, from 15 to 25, from 10 to 24, or from 10 to 30). In some embodiments, "$C_1$-$C_{10}$ alkyl" refers to a branched $C_1$-$C_{10}$ alkyl group. In some embodiments, the ammonium salt of Formula IX is a mixture of two or more such ammonium salts, such that the average (rounded to the nearest integer) value of d is an integer from 6 to 34 (e.g., from 6 to 30, from 6 to 24, from 6 to 20, from 6 to 16, from 6 to 12, from 5 to 25, from 10 to 20, from 15 to 25, from 10 to 24, or from 10 to 30). In certain embodiments, the cationic surfactant is hexadecyltrimethylammonium p-toluenesulfonate or hexadecyltrimethylammonium chloride.

The ammonium salt can have any suitable anion counter ion (i.e., "A"). In some embodiments, the anion counter ion ("A") comprises an element selected from a halogen (i.e., fluoride, chloride, bromide, or iodide), sulfur, carbon, nitrogen, phosphorous, and a combination thereof. An exemplary list of anions comprises fluoride, chloride, bromide, iodide, sulfide, sulfite, sulfate, bisulfate, bisulfite, thiosulfate, carbonate, bicarbonate, nitrate, nitrite, phosphate, hydrogen phosphate, dihydrogen phosphate, phosphite, hydrogen phosphite, dihydrogen phosphite, hexafluorophosphate, carboxylate, acetate, mesylate, tosylate, or triflate. In certain embodiments, A is selected from fluoride, chloride, bromide, mesylate, tosylate, or a combination thereof.

In some embodiments, the surfactant is an anionic surfactant. In certain embodiments, the anionic surfactant is a sulfate salt of Formula X:

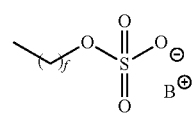

X wherein B is any cation, and f is an integer from 7 to 35 (e.g., from 7 to 29, from 7 to 23, from 7 to 19, from 7 to 15, from 7 to 11, from 11 to 19, from 11 to 23, or from 11 to 29). In some embodiments, the sulfate salt of Formula X is a mixture of two or more such sulfate salts, such that the average (rounded to the nearest integer) value off is an integer from 7 to 35 (e.g., from 7 to 29, from 7 to 23, from 7 to 19, from 7 to 15, from 7 to 11, from 11 to 19, from 11 to 23, or from 11 to 29). In certain embodiments, the anionic surfactant is sodium dodecylsulfate (i.e., f is 11).

The sulfate salt can have any suitable cation counter ion (i.e., "B"). For example, the cation counter ion ("B") can be a proton, ammonium, a quaternary amine, a cation of an alkali metal, a cation of an alkaline earth metal, a cation of a transition metal, a cation of a rare-earth metal, a main group element cation, or a combination thereof. In some embodiments, the cation counter ion is hydrogen or a cation of lithium, sodium, potassium, magnesium, calcium, manganese, iron, zinc, or a combination thereof. In certain embodiments, B is selected from hydrogen, lithium, sodium, potassium, or a combination thereof.

In some embodiments, the surfactant is a nonionic surfactant. The nonionic surfactant can be any suitable nonionic surfactant. In some embodiments, the nonionic surfactant comprises repeating units of ethylene oxide, propylene oxide, or ethylene oxide and propylene oxide. In certain embodiments, the surfactant comprises block or random copolymers of ethylene oxide ("EO"), propylene oxide ("PO"), or a combination thereof.

In certain embodiments, the nonionic surfactant is of Formula XI:

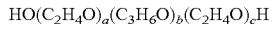

XI wherein a, b, and c are independently integers ranging from about 2 to about 200 (e.g., from about 2 to about 175, from about 2 to about 150, from about 2 to about 125, from about 2 to about 100, from about 50 to about 200, from about 50 to about 150, or from about 50 to about 100), and a, b, and c are the same or different. In some embodiments, the nonionic surfactant of Formula X is a mixture of two or more such surfactants, such that a, b, and c refer to an average (rounded to the nearest integer) chain length of the designated subunits (i.e., average chain length of EO and PO) wherein a, b, and c are independently integers from about 2 to about 200 (e.g., from about 2 to about 175, from about 2 to about 150, from about 2 to about 125, from about 2 to about 100, from about 50 to about 200, from about 50 to about 150, or from about 50 to about 100). In certain embodiments, the nonionic surfactant is PLURONIC® F-127 surfactant, i.e., $HO(C_2H_4O)_{101}(C_3H_6O)_{56}(C_2H_4O)_{101}H$, marketed by BASF Corporation (Florham Park, N.J.).

In some embodiments, the nonionic surfactant is of Formula XII:

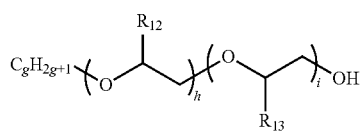

wherein g is an integer ranging from about 6 to about 50 (e.g., from about 6 to about 42, from about 6 to about 36, from about 6 to about 30, from about 6 to about 24, from about 6 to about 18, from about 6 to about 12, from about 8 to about 30, from about 12 to about 50, from about 12 to about 36, or from about 12 to about 24), each $R_{12}$ and $R_{13}$ are independently H or $C_1$-$C_4$ alkyl (e.g., methyl, ethyl, n-propyl, iso-propyl, n-butyl, sec-butyl, or tert-butyl), and h and i are independently integers ranging from 0 to about 100 (e.g., from about 0 to about 90, from about 0 to about 80, from about 0 to about 70, from about 0 to about 60, from about 0 to about 50, from about 10 to about 100, or from about 10 to about 50). In some embodiments, the surfactant of Formula XII is a mixture of two or more such surfactants, such that g, h, and i refer to an average (rounded to the nearest integer) chain length of the designated subunits (i.e., average carbon chain length or average EO (or substituted EO) chain length), wherein g is an integer from about 6 to about 50 (e.g., from about 6 to about 42, from about 6 to about 36, from about 6 to about 30, from about 6 to about 24, from about 6 to about 18, from about 6 to about 12, from about 8 to about 30, from about 12 to about 50, from about 12 to about 36, or from about 12 to about 24), and h and i are independently integers ranging from 0 to about 100 (e.g., from about 0 to about 90, from about 0 to about 80, from about 0 to about 70, from about 0 to about 60, from about 0 to about 50, from about 10 to about 100, or from about 10 to about 50).

In certain embodiments, the nonionic surfactant is of Formula XII:

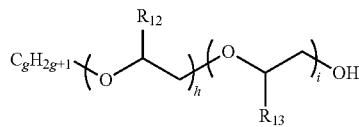

wherein g is an integer ranging from about 6 to about 50 (e.g., from about 6 to about 42, from about 6 to about 36, from about 6 to about 30, from about 6 to about 24, from about 6 to about 18, from about 6 to about 12, from about 12 to about 36, or from about 12 to about 24), $R_{12}$ and $R_{13}$ are H, and h and i are independently integers ranging from 0 to about 100 (e.g., from about 0 to about 90, from about 0 to about 80, from about 0 to about 70, from about 0 to about 60, from about 0 to about 50, from about 10 to about 100, or from about 10 to about 50). In certain embodiments, the surfactant is BRIJ® S20, i.e., a polyethylene glycol octadecyl ether of the formula $C_{18}H_{37}(OC_2H_4)_{h'}OH$, wherein h' is an integer ranging from about 2 to about 200, marketed by Croda International PLC (East Yorkshire, United Kingdom).

In certain embodiments, the nonionic surfactant is of Formula XII:

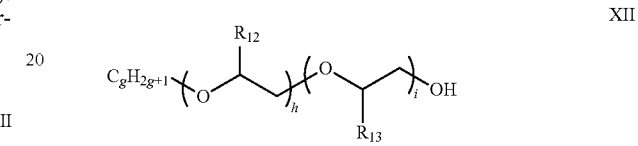

wherein g is an integer ranging from about 6 to about 50 (e.g., from about 6 to about 42, from about 6 to about 36, from about 6 to about 30, from about 6 to about 24, from about 6 to about 18, from about 6 to about 12, from about 12 to about 50, from about 12 to about 36, or from about 12 to about 24), i is 0, $R_{12}$ is H, and h is an integer ranging from about 2 to about 30 (e.g., from 2 to 30, from 4 to 30, from 6 to 30, from 8 to 30, from 10 to 30, from 12 to 30, from 16 to 30, from 18 to 30, from 20 to 30, from 22 to 30, or from 24 to 30). In certain embodiments, the surfactant is a Lutensol® fatty alcohol ethoxylate commercially available from BASF Corporation (Florham Park, N.J.). More preferably, the surfactant is polyethoxy (25) cetyl and/or stearyl alcohol, marketed under the product name (25 EO) C16-C18 fatty alcohol ("LutensolAT® 25"), commercially available from BASF Corporation (Florham Park, N.J.).

In certain embodiments, the nonionic surfactant is of Formula XII:

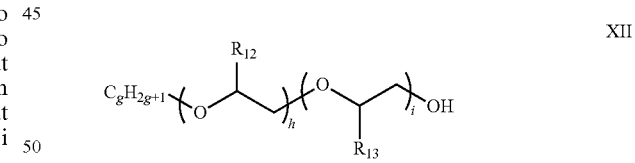

wherein g is an integer ranging from about 8 to about 30 (e.g., from 10 to 30, from 12 to 30, from 16 to 30, from 18 to 30, from 20 to 30, from 22 to 30, or from 24 to 30), each $R_{12}$ and $R_{13}$ are independently H or $C_1$-$C_4$ alkyl (e.g., methyl, ethyl, n-propyl, iso-propyl, n-butyl, sec-butyl, or tert-butyl), and h and i are independently integers ranging from 0 to about 50 (e.g., from about 0 to about 40, from about 0 to about 30, from about 0 to about 20, from about 10 to about 50, from about 10 to about 40, from about 10 to about 30, or from about 10 to about 20). In certain embodiments, the surfactant is a Plurafac® surfactant, commercially available from BASF Corporation (Florham Park, N.J.).

In certain embodiments, the nonionic surfactant is of Formula XIII:

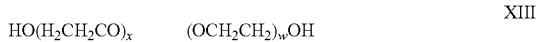

XIII wherein w, x, y, and z are integers from about 0 to about 50 (e.g., from about 0 to about 40, from about 0 to about 30, from about 0 to about 20, from about 0 to about 16, from about 0 to about 12, or from about 0 to about 8), and w, x, y, and z are the same or different. In some embodiments, the nonionic surfactant of Formula XIII is a mixture of two or more such surfactants, such that w, x, y, and z refer to an average (rounded to the nearest integer) chain length of the designated subunits (i.e., average chain length of EO) wherein w, x, y, and z are integers from about 0 to about 50 (e.g., from about 0 to about 40, from about 0 to about 30, from about 0 to about 20, from about 0 to about 16, from about 0 to about 12, or from about 0 to about 8). In certain embodiments, the nonionic surfactant is TWEEN® 20 surfactant, i.e., w+x+y+z=20, marketed by Croda International PLC (East Yorkshire, United Kingdom).

When the one or more surfactant(s) is present in the powder, the one or more surfactant(s) can be present in the powder at any suitable concentration. The powder can comprise a sum total of about 20 wt. % or less of the surfactant(s), for example, about 15 wt. % or less, about 10 wt. % or less, about 9 wt. % or less, about 8 wt. % or less, about 7 wt. % or less, about 6 wt. % or less, or about 5 wt. % or less. Alternatively, or in addition to, the powder can comprise a sum total of about 0.001 wt. % or more of the surfactant(s), for example, about 0.01 wt. %, about 0.1 wt. %, about 0.25 wt. % or more, about 0.5 wt. % or more, about 1 wt. % or more, about 2 wt. % or more, about 3 wt. % or more, or about 4 wt. % or more. Thus, the powder can comprise the one or more surfactant(s) in a concentration bounded by any two of the aforementioned endpoints. The powder can comprise a sum total of from about 0.001 wt. % to about 5 wt. %, from about 0.01 wt. % to about 5 wt. %, from about 0.1 wt. % to about 5 wt. % surfactant, for example, from about 0.25 wt. % to about 5 wt. %, from about 0.5 wt. % to about 5 wt. %, from about 1 wt. % to about 5 wt. %, from about 2 wt. % to about 5 wt. %, from about 3 wt. % to about 5 wt. %, from about 4 wt. % to about 5 wt. %, from about 4 wt. % to about 10 wt. %, from about 4 wt. % to about 9 wt. %, from about 4 wt. % to about 8 wt. %, from about 4 wt. % to about 7 wt. %, from about 4 wt. % to about 6 wt. %, from about 0.001 wt. % to about 10 wt. %, from about 0.01 wt. % to about 10 wt. %, from about 0.1 wt. % to about 10 wt. %, from about 0.001 wt. % to about 15 wt. %, from about 0.01 wt. % to about 15 wt. %, from about 0.1 wt. % to about 15 wt. %, from about 0.001 wt. % to about 20 wt. %, from about 0.01 wt. % to about 20 wt. %, from about 0.1 wt. % to about 20 wt. %, or from about 0.001 wt. % to about 1 wt. %.

In an embodiment, the one or more surfactant(s) are added before the formation of the powder (e.g., to the polymer solution, before or after polymerization, or to the wet gel). When the surfactant(s) are added before the formation of the powder, the surfactant(s) are incorporated into the wet gel, and thereby the powder. Generally, the surfactant(s) improve the processability of the wet gel into a powder. Typically the surfactant(s) further improve the solubility or dispersibility of the resulting powder in aqueous media or other solvent.

In some embodiments, the one or more surfactant(s) is added to the powder after being processed from the wet gel. In some embodiments, the one or more surfactant(s) are not necessary for the wet gel to be processed. In particular, the chemical interactions of the associative monomer units may be strong enough to network the associative polymer(s) in the absence of surfactant(s). While the surfactant is not always necessary for the formation of the powder, the resulting powder (absent of one or more surfactant(s)) is generally less soluble in an aqueous medium. For example, the one or more surfactant(s) tend to facilitate re-wetting of the associative polymer(s) and speed up the process of forming a solution in water. Thus, a surfactant can be added after formation of the powder in order to improve solubility and dispersibility of the resulting powder in an aqueous medium or other solvent.

The polymerization to form the associative polymer(s) can be carried out according to any suitable polymerization known in the art. For example, the associative polymer(s) can be made by emulsion polymerization, dispersion polymerization, solution polymerization, gel polymerization, or a combination thereof. The polymerization to form the associative polymer(s) can occur through any suitable mechanism. For example, the polymerization can occur through cationic polymerization, anionic polymerization, free-radical polymerization, coordination polymerization, or combinations thereof. Typically, polymerization occurs through free radical polymerization.

In some embodiments, the polymerization to form the associative polymer(s) comprises one or more polymerization component(s). In certain embodiments, the one or more polymerization component(s) are not removed from the reaction mixture such that one or more of the polymerization component(s) remains in the polymer solution, the polymer wet gel, and/or the powder. In other embodiments, the one or more polymerization component(s) are removed such that the one or more polymerization component(s) are not present in the polymer solution, the polymer wet gel, and/or the powder. In some embodiments, the one or more polymerization component(s) are transformed such that one or more transformed polymerization components are present in the polymer solution, the polymer wet gel, and/or the powder. An exemplary list of polymerization components is an initiator, a chain transfer agent, a chelant, a redox agent, a buffer, and a combination thereof.

In some embodiments, the polymerization comprises one or more initiator(s). The initiator can be any suitable initiator. In some embodiments, the initiator is a free radical initiator. In certain embodiments, the initiator is selected from the group of azobis compounds. An exemplary list of initiators is 2,2'-azobis(2,4-dimethyl valeronitrile), 2,2'-azobis(4-methoxy-2,4-dimethyl valeronitrile), 1,1'-azobis(cyclohexane-1-carbonitrile), 2,2'-azobis(2-methylbutyronitrile), 2,2'-azobis(2-methylpropionamidine)dihydrochloride, 2,2'-azobis[2-(2-imidazolin-2-yl)propane]dihydrochloride, 2,2'-azobis[N-(2-carboxyethyl)-2-methylpropionamidine] hydrate (anhydride), and 2,2'-azobis[2-(2-imidazolin-2-yl) propane].

In some embodiments, the polymerization comprises one or more chain transfer agent(s). The chain transfer agent can be any suitable chain transfer agent. An exemplary list of chain transfer agents is carbon tetrachloride, carbon tetrabromide, bromotrichloromethane, pentaphenylethane, sodium formate, sodium hypophosphite, thiophenol, 4,4'-thiobisbenzenethiol, 4-methylbenzenethiol, and aliphatic thiols such as isooctyl 3-mercaptopropionate, tert-nonyl mercaptan, and N-acetyl-L-cysteine, N-2-mercaptoethyl)acetamide, glutathione, N-(2-mercaptopropionyl)glycine, and 2-mercaptoethanol.

In some embodiments, the polymerization comprises one or more chelant(s). The chelant can be any suitable chelant. In certain embodiments, the chelant is a polydentate organic compound. An exemplary list of chelating agents is diethylenetriaminepentaacetic acid ("DTPA"), ethylenediaminetetraacetic acid ("EDTA"), nitrilotriacetic acid ("NTA"), diethylenetriaminepentaacetic acid, N,N-bis(carboxymethyl)-L-glutamic acid, trisodium N-(hydroxyethyl)-ethylenediaminetriacetate, adipic acid, and salts thereof.

In some embodiments, the polymerization comprises one or more redox agent(s). The redox agent can be any suitable redox agent. In some embodiments, the redox agent aids in terminating the polymerization. In certain embodiments, the redox reagent is an organic peroxide, an inorganic peroxide, or a combination thereof. An exemplary list of redox agents is sodium bisulfate; a thiosulfate, ferrous ammonium sulfate; ascorbic acid, an amine, a hypophosphite, sodium bromate, a chlorate, a permanganate, ammonium persulfate, potassium persulfate, sodium persulfate, t-butyl hydrogen peroxide, hydrogen peroxide, ozone, and salts thereof. In some embodiments, the redox agent is added as a redox pair such that one agent participates in reduction and one agent participates in oxidation. In certain embodiments, the redox agent is the initiator.

In some embodiments, the polymerization comprises a buffer system. The buffer system can be any suitable organic and/or inorganic buffer system. In certain embodiments, the buffer system comprises an organic and/or inorganic acid and/or base capable of controlling the pH lower than about 6 (e.g., from about 0 to about 6, from about 1 to about 6, from about 2 to about 6, from about 3 to about 6, from about 4 to about 6, from about 5 to about 6, from about 0 to about 1, from about 0 to about 2, from about 0 to about 3, from about 0 to about 4, or from about 0 to about 5). An exemplary list of buffers is adipic acid, pimelic acid, glutaric acid, citric acid, acetic acid, an inorganic acid (e.g., phosphoric acid), an amine, and salts thereof.

The solution of one or more associative polymer(s) and optionally one or more surfactant(s) can be converted to a wet gel by any suitable technique. In some embodiments, the solution of one or more associative polymer(s) and optionally one or more surfactant(s) spontaneously becomes a wet gel. For example, the solution-based monomers can polymerize in the presence of the one or more surfactant(s) and polymerization results in a transition from solution-based monomers to solution-based polymers which spontaneously begin to solidify to form the polymer wet gel. In some embodiments, the solution of one or more associative polymer(s) and optionally one or more surfactant(s) may need to be dried prior to formation of a wet gel. For example, the solution of one or more associative polymer(s) and optionally one or more surfactant(s) can be converted to a wet gel through drying (e.g., placing in an oven and/or ambient temperature evaporation), cooling, change in pressure, or a combination thereof. As used herein, "wet gel" refers to any material produced when a solution of one or more associative polymer(s) and optionally one or more surfactant(s) transitions from a fluid-like to solid-like state. In certain embodiments, the wet gel maintains a taffy-like consistency and is not sticky.

The wet gel comprises the resulting associatively networked polymer, optionally one or more surfactant(s), and a solvent. Generally, the wet gel contains about 20 wt. % to about 80 wt. % of the associatively networked polymer. In an embodiment, the polymer wet gel comprises from about 25 wt. % to about 50 wt. % polymer. In certain embodiments, the polymer wet gel comprises from about 30 wt. % to about 40 wt. % polymer.

The wet gel can be processed to a powder by any suitable process. In some embodiments, the wet gel is processed to a powder by cutting the wet gel to form granules, drying the granules, and converting the dried granules to form a powder. In some embodiments, the wet gel is processed to a powder by drying the wet gel, cutting the dried wet gel into granules, and converting the granules to a powder. In some embodiments, the wet gel is process to a powder by drying the wet gel, cutting the dried wet gel to granules, drying the granules, and converting the dried granules to form a powder. The wet gel can be cut by any suitable method. In certain embodiments, the wet gel is machine processed (for example, using a Retsch Mill Cutter) to form wet gel granules. In certain embodiments, the wet gel is cut with the aid of a lubricant. The lubricant can be any suitable lubricant (e.g., a petroleum oil based lubricant). The wet gel granules can be converted to a powder by any suitable method. In some embodiments, "converting the granules to form a powder" refers to the process of, for example, optionally drying the granules further, grinding the granules, or drying and grinding the granules to produce a powder, though the converting may include other processing steps. For example, converting the granules to a powder can further comprise sifting.

The powder can have any suitable moisture content. Generally, the moisture content is from about 0 wt. % to about 30 wt. % (e.g., from about 0.01 wt. % to about 30 wt. %, from about 0.1 wt. % to about 30 wt. %, or from about 1 wt. % to about 30 wt. %). In certain embodiments of the powder, the moisture content is from about 0 wt. % to about 25 wt. % (e.g., from about 0.01 wt. % to about 25 wt. %, from about 0.1 wt. % to about 25 wt. %, or from about 1 wt. % to about 25 wt. %). In certain embodiments of the powder, the moisture content is from about 0 wt. % to about 20 wt. % (e.g., from about 0.01 wt. % to about 20 wt. %, from about 0.1 wt. % to about 20 wt. %, from about 0.1 wt. % to about 10 wt. %, or from about 1 wt. % to about 20 wt. %). In certain embodiments, the moisture content is about 10 wt. %.

The powder can have any suitable mean particle size (i.e., mean particle diameter). The mean particle size can be determined by any suitable method known in the art. Generally, the mean particle size is determined by a Horiba Laser Scattering Particle Size Distribution Analyzer LA-950. The powder can have a mean particle size of about 1 micron or more, for example, about 10 microns or more, about 20 microns or more, about 50 microns or more, about 100 microns or more, about 200 microns or more, or about 500 microns or more. Alternatively, or in addition, the powder can have a mean particle size of about 10,000 microns or less, for example, about 8,000 microns or less, about 6,000 microns or less, about 4,000 microns or less, or about 2,000 microns or less. Thus, the powder can have a mean particle size bounded by any two of the aforementioned endpoints. The powder can have a mean particle size of from about 1 micron to about 10,000 microns, for example, from about 1 micron to about 8,000 microns, from about 1 micron to about 6,000 microns, from about 1 micron to about 4,000 microns, from about 1 micron to about 2,000 microns, from about 10 microns to about 2,000 microns, from about 20 microns to about 2,000 microns, from about 50 microns to about 2,000 microns, from about 100 microns to about 2,000 microns, from about 200 microns to about 2,000 microns, or from about 500 microns to about 2,000 microns.

The powder can have any suitable particle shape. In some embodiments, the powder particles are non-spherical. Without wishing to be bound to any particular theory, it is believed that non-spherical particles are generally formed when the powder has been manufactured by a gel-, spray-, or drum-based process (e.g., via cutting and drying). In some embodiments, the powder particles are spherical. Without wishing to be bound to any particular theory, it is believed that spherical particles are generally formed when the powder has been manufactured by a bead-based process.

In some embodiments, the powder, at a median particle size of at least 300 microns, is soluble as up to a 20 wt. % solution in water with stirring by a cage stirrer at 400 rpm within one hour at room temperature. In some embodiments, the powder, at a median particle size of at least 300 microns, is soluble as up to a 10 wt. % solution in water with stirring by a cage stirrer at 400 rpm within one hour at room temperature. In certain embodiments, the powder, at a median particle size of at least 300 microns, is soluble as up to a 5 wt. % solution in water with stirring by a cage stirrer at 400 rpm within one hour at room temperature. In certain embodiments, the powder, at a median particle size of at least 300 microns, is soluble as up to a 1 wt. % solution in water with stirring by a cage stirrer at 400 rpm within one hour at room temperature. In some embodiments, generally, when the powder does not comprise one or more surfactant(s), the powder, at a median particle size of at least 300 microns, does not completely dissolve, or is sparingly soluble in water (i.e., did not completely dissolve as a 1 wt. % solution in water within one hour at room temperature). Without wishing to be bound by any particular theory, it is believed that the chemical interactions (e.g., networking) diminish as the concentrations of associative polymer(s) and optional surfactant(s) are reduced below their critical concentration, thereby releasing the active polymer strength aid (i.e., associative polymer) and further improving solubility. As used herein, "critical concentration" refers to the concentration at which the associative polymer(s) and surfactant(s) transition from being solution-based to maintaining an organized network structure.

The resulting powder can have any suitable intrinsic viscosity. For example, the powder can have an intrinsic viscosity of from about 0.05 dL/g to about 7 dL/g (e.g., from about 0.05 dL/g to about 6 dL/g., from about 0.05 dL/g to about 5 dL/g, from about 0.05 dL/g to about 4 dL/g, from about 0.05 dL/g to about 3 dL/g, from about 0.05 dL/g to about 2 dL/g, from about 0.05 dL/g to about 1 dL/g, from about 0.05 dL/g to about 0.5 dL/g, from about 0.1 dL/g to about 7 dL/g, from about 0.1 dL/g to about 6 dL/g, or from about 0.5 dL/g to about 5 dL/g). In some embodiments, the powder has an intrinsic viscosity from about 0.1 dL/g to about 6. In certain embodiments, the powder has an intrinsic viscosity of from about 0.5 dL/g to about 5 dL/g.

Intrinsic viscosity ("IV") is defined by a series of reduced specific viscosity ("RSV") measurements extrapolated to the limit of infinite dilution, i.e., when the concentration of powder is equal to zero. The RSV is measured at a given powder concentration and temperature and calculated as follows:

$$RSV = \frac{\left(\frac{\eta}{\eta_0} - 1\right)}{c} = \frac{\left(\frac{t}{t_0} - 1\right)}{c}$$

wherein $\eta$ is viscosity of the powder solution, $\eta_0$ is viscosity of the solvent at the same temperature, an t is elution time of powder solution, $t_0$ is elution time of solvent, and c is concentration (g/dL) of the powder in solution. Thus, intrinsic viscosity is defined by dL/g. Variables t and to are measured using powder solution and solvent that is in 1.0 N sodium nitrate solution with a Cannon Ubbelohde semimicro dilution viscometer (size 75) at 30±0.02° C.

The resulting powder can have any suitable Huggins constant. For example, the resulting powder can have a Huggins constant from about 0.1 to about 20 (e.g., from about 0.1 to about 15, from about 0.1 to about 10, from about 0.3 to about 10, from about 0.1 to about 5, from about 0.5 to about 20, from about 0.5 to about 10, from about 1 to about 20, from about 1 to about 10, or from about 1 to about 5). In some embodiments, the powder can have a Huggins constant of from about 0.3 to about 10 as determined by varying concentrations of the powder, wherein the concentrations have been chosen such that they produce a value of $$\left(\frac{t}{t_0}\right)$$

between about 1.2 and 2.2, in a 1.0 N sodium nitrate solution. In some embodiments, the powder can have a Huggins constant of from about 0.3 to about 5 as determined by varying concentrations of the powder, wherein the concentrations have been chosen such that they produce a value of $$\left(\frac{t}{t_0}\right)$$

between about 1.2 and 2.2, in a 1.0 N sodium nitrate solution. In certain embodiments, the powder has a Huggins constant of from about 0.6 to about 3 as determined by varying concentrations of the powder, wherein the concentrations have been chosen such that they produce a value of $$\left(\frac{t}{t_0}\right)$$

between about 1.2 and 2.2, in a 1.0 N sodium nitrate solution. The Huggins constant is calculated as follows:

$$\text{Huggins constant} = \frac{\text{slope of } (RSV \sim c)}{IV^2}$$

A powder is also provided herein. The powder comprises one or more associatively networked polymer(s) comprising one or more associative monomer unit(s) and one or more monomer units selected from at least one of a cationic monomer unit, an anionic monomer unit, a nonionic monomer unit, a zwitterionic monomer unit, or a combination thereof, and optionally one or more surfactant(s), wherein the associative polymer(s) have a weight average molecular weight of from about 10 kDa to about 2,000 kDa. In some embodiments, the powder comprises one or more low molecular weight associative polymer(s) that are reversibly associated in a polymer network, wherein the association is controllable via degree of dilution in aqueous media, or amount of surfactant present.

In some embodiments, the powder comprises a nonionic surfactant and an associative polymer comprising an associative monomer unit derived from a monomer of Formula II, a monomer unit derived from a monomer of Formula I, and an additional cationic monomer unit. In some embodiments, the powder comprises a nonionic surfactant and an associative polymer comprising an associative monomer unit derived from a monomer of Formula II, a monomer unit derived from a monomer of Formula I, and an additional monomer unit derived from DMAEA.MCQ. In some embodiments, the powder comprises a nonionic surfactant and an associative polymer comprising an associative monomer unit derived from a monomer of Formula II, an additional monomer unit derived from acrylamide, and an additional monomer unit derived from DMAEA.MCQ. In certain embodiments, the powder comprises a nonionic surfactant and an associative polymer comprising an associative monomer unit derived from VISIOMER® monomer C18PEG1105MA, an additional monomer unit derived from acrylamide, and an additional monomer unit derived from DMAEA.MCQ. In certain embodiments, the powder comprises a nonionic surfactant of Formula XII, and an associative polymer comprising an associative monomer unit derived from VISIOMER® monomer C18PEG1105MA, an additional monomer unit derived from acrylamide, and an additional monomer unit derived from DMAEA.MCQ. In certain embodiments, the powder comprises PLURONIC®

F-127 surfactant and/or LutensolAT® 25 surfactant, and an associative polymer comprising an associative monomer unit derived from VISIOMER® monomer C18PEG1105MA, an additional monomer unit derived from acrylamide, and an additional monomer unit derived from DMAEA.MCQ.

In some embodiments, the powder comprises a nonionic surfactant and an associative polymer comprising an associative monomer unit derived from a monomer of Formula II, a monomer unit derived from a monomer of Formula I, and an additional anionic monomer unit. In some embodiments, the powder comprises a nonionic surfactant and an associative polymer comprising an associative monomer unit derived from a monomer of Formula II, a monomer unit derived from a monomer of Formula I, and an additional monomer unit derived from sodium acrylate. In some embodiments, the powder comprises a nonionic surfactant and an associative polymer comprising an associative monomer unit derived from a monomer of Formula II, an additional monomer unit derived from acrylamide, and an additional monomer unit derived from sodium acrylate. In certain embodiments, the powder comprises a nonionic surfactant and an associative polymer comprising an associative monomer unit derived from VISIOMER® monomer C18PEG1105MA, an additional monomer unit derived from acrylamide, and an additional monomer unit derived from sodium acrylate. In certain embodiments, the powder comprises a nonionic surfactant of Formula XII, and an associative polymer comprising an associative monomer unit derived from VISIOMER® monomer C18PEG1105MA, an additional monomer unit derived from acrylamide, and an additional monomer unit derived from sodium acrylate. In certain embodiments, the powder comprises PLURONIC® F-127 surfactant and/or LutensolAT® 25 surfactant, and an associative polymer comprising an associative monomer unit derived from VISIOMER® monomer C18PEG1105MA, an additional monomer unit derived from acrylamide, and an additional monomer unit derived from sodium acrylate.

In some embodiments, the powder comprises a cationic surfactant and an associative polymer comprising an associative monomer unit derived from a monomer of Formula VI, a monomer unit derived from a monomer of Formula I, and an additional cationic monomer unit. In some embodiments, the powder comprises a cationic surfactant and an associative polymer comprising an associative monomer unit derived from a monomer of Formula VI, a monomer unit derived from a monomer of Formula I, and an additional monomer unit derived from DMAEA.MCQ. In some embodiments, the powder comprises a cationic surfactant and an associative polymer comprising an associative monomer unit derived from a monomer of Formula VI, an additional monomer unit derived from acrylamide, and an additional monomer unit derived from DMAEA.MCQ. In certain embodiments, the powder comprises a cationic surfactant and an associative polymer comprising an associative monomer unit derived from MAPTAC-C12 derivative of Formula VII, an additional monomer unit derived from acrylamide, and an additional monomer unit derived from DMAEA.MCQ. In certain embodiments, the powder comprises a cationic surfactant of Formula IX, and an associative polymer comprising an associative monomer unit derived from MAPTAC-C12 derivative of Formula VII, an additional monomer unit derived from acrylamide, and an additional monomer unit derived from DMAEA.MCQ. In certain embodiments, the powder comprises cetyltrimethylammonium chloride and/or hexadecyltrimethylammonium p-toluenesulfonate, and an associative polymer comprising an associative monomer unit derived from MAPTAC-C12 derivative of Formula VII, an additional monomer unit derived from acrylamide, and an additional monomer unit derived from DMAEA.MCQ.

In some embodiments, the powder comprises a cationic surfactant and an associative polymer comprising an associative monomer unit derived from a monomer of Formula VI, a monomer unit derived from a monomer of Formula I, and an additional anionic monomer unit. In some embodiments, the powder comprises a cationic surfactant and an associative polymer comprising an associative monomer unit derived from a monomer of Formula VI, a monomer unit derived from a monomer of Formula I, and an additional monomer unit derived from sodium acrylate. In some embodiments, the powder comprises a cationic surfactant and an associative polymer comprising an associative monomer unit derived from a monomer of Formula VI, an additional monomer unit derived from acrylamide, and an additional monomer unit derived from sodium acrylate. In certain embodiments, the powder comprises a cationic surfactant and an associative polymer comprising an associative monomer unit derived from MAPTAC-C12 derivative of Formula VII, an additional monomer unit derived from acrylamide, and an additional monomer unit derived from sodium acrylate. In certain embodiments, the powder comprises a cationic surfactant of Formula IX, and an associative polymer comprising an associative monomer unit derived from MAPTAC-C12 derivative of Formula VII, an additional monomer unit derived from acrylamide, and an additional monomer unit derived from sodium acrylate. In certain embodiments, the powder comprises cetyltrimethylammonium chloride and/or hexadecyltrimethylammonium p-toluenesulfonate, and an associative polymer comprising an associative monomer unit derived from MAPTAC-C12 derivative of Formula VII, an additional monomer unit derived from acrylamide, and an additional monomer unit derived from sodium acrylate.

In some embodiments, the powder comprises an anionic surfactant and an associative polymer comprising an associative monomer unit derived from a monomer of Formula VIII, a monomer unit derived from a monomer of Formula I, and an additional cationic monomer unit. In some embodiments, the powder comprises an anionic surfactant and an associative polymer comprising an associative monomer unit derived from a monomer of Formula VIII, a monomer unit derived from a monomer of Formula I, and an additional monomer unit derived from DMAEA.MCQ. In some embodiments, the powder comprises an anionic surfactant and an associative polymer comprising an associative monomer unit derived from a monomer of Formula VIII, an additional monomer unit derived from acrylamide, and an additional monomer unit derived from DMAEA.MCQ. In certain embodiments, the powder comprises an anionic surfactant of formula X, and an associative polymer comprising an associative monomer unit derived from a monomer of Formula VIII, an additional monomer unit derived from acrylamide, and an additional monomer unit derived from DMAEA.MCQ. In certain embodiments, the powder comprises sodium dodecyl sulfate, and an associative polymer comprising an associative monomer unit derived from a monomer of Formula VIII, an additional monomer unit derived from acrylamide, and an additional monomer unit derived from DMAEA.MCQ.

In some embodiments, the powder comprises an anionic surfactant and an associative polymer comprising an associative monomer unit derived from a monomer of Formula VIII, a monomer unit derived from a monomer of Formula I, and an additional anionic monomer unit. In some embodiments, the powder comprises an anionic surfactant and an associative polymer comprising an associative monomer unit derived from a monomer of Formula VIII, a monomer unit derived from a monomer of Formula I, and an additional monomer unit derived from sodium acrylate. In some embodiments, the powder comprises an anionic surfactant and an associative polymer comprising an associative monomer unit derived from a monomer of Formula VIII, an additional monomer unit derived from acrylamide, and an additional monomer unit derived from sodium acrylate. In certain embodiments, the powder comprises an anionic surfactant of formula X, and an associative polymer comprising an associative monomer unit derived from a monomer of Formula VIII, an additional monomer unit derived from acrylamide, and an additional monomer unit derived from sodium acrylate. In certain embodiments, the powder comprises sodium dodecyl sulfate, and an associative polymer comprising an associative monomer unit derived from a monomer of Formula VIII, an additional monomer unit derived from acrylamide, and an additional monomer unit derived from sodium acrylate.

The individual components of the powder, for example, the one or more associative polymer(s) and one or more optional surfactant(s), are as defined by the parameters set forth herein.

The individual structures of the one or more associative polymer(s), for example, the one or more associative monomer unit(s) and one or more monomer unit(s) selected from at least one of a cationic monomer unit, an anionic monomer unit, a nonionic monomer unit, a zwitterionic monomer unit, or a combination thereof, are as defined by the parameters set forth herein.

The individual structures of the one or more surfactant(s) are as defined by the parameters set forth herein.

The quantities of the individual components of the powder, for example, the amount of the one or more associative polymer(s) and optionally one or more surfactant(s), are as defined by the parameters set forth herein.

The quantities of the individual monomer units of the associative polymer(s), for example, the amount of the one or more associative monomer unit(s) and one or more monomer unit(s) selected from at least one of a cationic monomer unit, an anionic monomer unit, a nonionic monomer unit, a zwitterionic monomer unit, or a combination thereof, are as defined by the parameters set forth herein.

In certain embodiments, the physical characteristics of the powder are as defined by the parameters set forth herein.

The invention is further illustrated by the following embodiments.

(1) A powder, comprising one or more associative polymer(s) comprising one or more associative monomer unit(s) and one or more additional monomer unit(s) selected from at least one of a cationic monomer unit, an anionic monomer unit, a nonionic monomer unit, a zwitterionic monomer unit, or a combination thereof, and optionally one or more surfactant(s), wherein the associative polymer(s) have a weight average molecular weight of from about 10 kDa to about 2,000 kDa.

(2) The powder of embodiment (1), wherein the one or more associative monomer unit(s) is derived from an acrylate monomer, an acrylamide monomer, or a combination thereof.

(3) The powder of embodiment (1) or (2), wherein the one or more associative polymer(s) comprises a nonionic associative monomer unit.

(4) The powder of embodiment (3), wherein the nonionic associative monomer unit is derived from a monomer of Formula II:

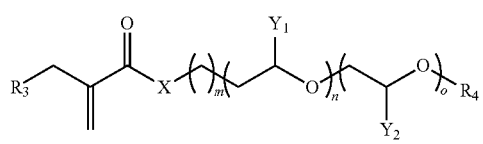

wherein $R_3$ is H or $C_1$-$C_{10}$ alkyl, X is O or NH, m, n, and o are independently integers from 0 to 100, wherein when (n+o)≤3, m is at least 7, each $Y_1$ and $Y_2$ are independently H or $C_1$-$C_4$ alkyl, and $R_4$ is H or a hydrophobic group.

(5) The powder of embodiment (4), wherein the nonionic associative monomer unit is derived from a monomer of Formula III:

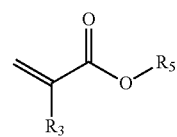

wherein $R_5$ is —$CH_2(CH_2)_pCH_3$, $R_3$ is H or $C_1$-$C_{10}$ alkyl, and p is an integer from 3 to 100.

(6) The powder of embodiment (5), wherein the nonionic monomer unit is derived from laurylacrylate, cetylacrylate, stearylacrylate, behenylacrylate, or a combination thereof.

(7) The powder of embodiment (6), wherein the nonionic monomer unit is derived from laurylacrylate.

(8) The powder of embodiment (4), wherein the nonionic associative monomer unit is derived from a monomer of Formula IV:

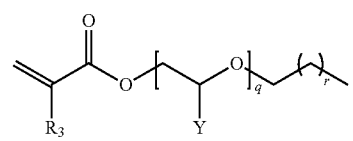

wherein $R_3$ is H or $C_1$-$C_{10}$ alkyl, q is an integer from 2 to 100, r is an integer from 0 to 30, and each Y is independently H or $CH_3$.

(9) The powder of embodiment (8), wherein the nonionic monomer unit is derived from lauryl polyethoxy (25) methacrylate, cetyl polyethoxy (25) methacrylate, stearyl polyethoxy (25) methacrylate, behenyl polyethoxy (25) methacrylate, or a combination thereof.

(10) The powder of embodiment (9), wherein the nonionic monomer unit is derived from a mixture of cetyl polyethoxy (25) methacrylate and stearyl polyethoxy (25) methacrylate.

(11) The powder of embodiment (1) or (2), wherein the one or more associative polymer(s) comprises a cationic associative monomer unit.

(12) The powder of embodiment (11), wherein the cationic associative monomer unit is derived from a monomer of Formula VI:

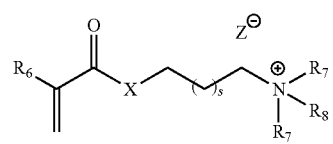

wherein $R_6$ and $R_7$ are each independently H or $C_1$-$C_{10}$ alkyl, X is O or NH, s is an integer from 0 to 20, Z is any anion, and $R_8$ is a hydrophobic group.

(13) The powder of embodiment (12), wherein the cationic associative monomer unit is derived from a monomer of Formula VII:

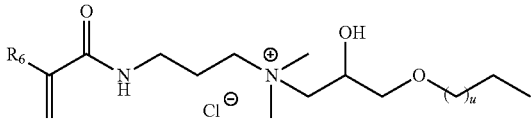

wherein $R_6$ is H or $C_1$-$C_{10}$ alkyl, and u is an integer from 0 to 30.

(14) The powder of embodiment (13), wherein the cationic associative monomer unit is derived from a monomer of Formula VII:

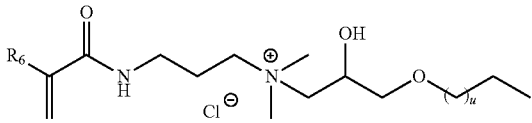

wherein $R_6$ is $CH_3$, and u is 10.

(15) The powder of embodiment (1) or (2), wherein the one or more associative polymer(s) comprises an anionic associative monomer unit.

(16) The powder of embodiment (15), wherein the anionic associative monomer unit is derived from a monomer of Formula VIII:

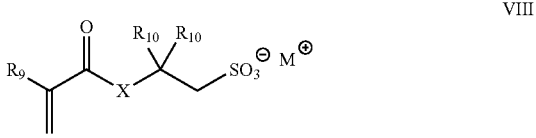

wherein $R_9$ is H or $C_1$-$C_{10}$ alkyl, X is O or NH, M is any cation, and each $R_{10}$ is independently H or an organic group.

(17) The powder of any one of embodiments (1)-(16), wherein the additional monomer unit is derived from a monomer selected from a monomer of Formula I:

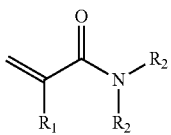

wherein $R_1$ is H or $C_1$-$C_4$ alkyl and each $R_2$ is independently H or an organic group; 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid; salts thereof; and combinations thereof.

(18) The powder of embodiment (17), wherein the additional monomer unit is derived from a monomer of Formula I:

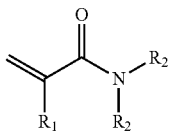

wherein $R_1$ is H or $C_1$-$C_4$ alkyl and each $R_2$ is independently H or an organic group.

(19) The powder of embodiment (18), wherein the organic group is a $C_1$-$C_6$ alkyl group.

(20) The powder of embodiment (18), wherein the additional monomer unit is derived from acrylamide.

(21) The powder of embodiment (19), wherein the additional monomer unit is derived from methacrylamide.

(22) The powder of embodiment (17), wherein the additional monomer unit is a cationic monomer unit derived from a monomer selected from 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), diallyldimethylammonium chloride ("DADMAC"), diallylamine, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), salts thereof, and combinations thereof.

(23) The powder of embodiment (22), wherein the additional monomer unit is derived from 2-(acryloyloxy)-N,N,N-trimethylethanaminium chloride ("DMAEA.MCQ").

(24) The powder of embodiment (22), wherein the additional monomer unit is derived from diallyldimethylammonium chloride ("DADMAC").

(25) The powder of embodiment (17), wherein the additional monomer unit is an anionic monomer unit derived from a monomer selected from 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

(26) The powder of embodiment (25), wherein the additional monomer unit is derived from acrylic acid.

(27) The powder of embodiment (25), wherein the additional monomer unit is derived from sodium acrylate.

(28) The powder of any one of embodiments (1-(27, wherein the powder comprises one or more surfactant(s).

(29) The powder of embodiment (28), wherein the surfactant is an anionic surfactant.

(30) The powder of embodiment (29), wherein the anionic surfactant is a sulfate salt of Formula X:

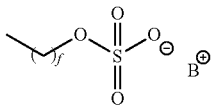

wherein B is any cation, and f is an integer from 7 to 35.

(31) The powder of embodiment (30, wherein the anionic surfactant is sodium dodecylsulfate.

(32) The powder of embodiment (28), wherein the surfactant is a cationic surfactant.

(33) The powder of embodiment (32), wherein the cationic surfactant is an ammonium salt of Formula IX:

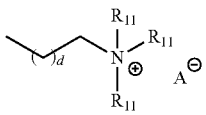

IX wherein each $R_{11}$ is independently H or $C_1$-$C_{10}$ alkyl, A is any anion, and d is an integer from 6 to 34.

(34) The powder of embodiment (33), wherein the cationic surfactant is hexadecyltrimethylammoniump-toluenesulfonate, hexadecyltrimethylammonium chloride, or a combination thereof.

(35) The powder of embodiment (28), wherein the surfactant is nonionic.

(36) The powder of embodiment (35), wherein the nonionic surfactant is a block or random polymer comprising ethylene oxide, propylene oxide, or a combination thereof.

(37) The powder of embodiment (36), wherein the polymer is of Formula XI:

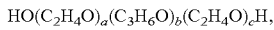

XI wherein a, b, and c are integers ranging from about 2 to about 200 and a, b, and c are the same or different.

(38) The powder of embodiment (37), wherein the nonionic surfactant is $HO(C_2H_4O)_{101}(C_3H_6O)_{56}(C_2H_4O)_{101}H$.

(39) The powder of embodiment (35), wherein the nonionic surfactant is of Formula XII:

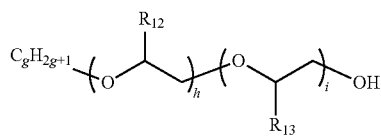

XII wherein g is an integer ranging from about 6 to about 50, each $R_{12}$ and $R_{13}$ are independently H or $C_1$-$C_4$ alkyl, and h and i are independently integers ranging from 0 to about 100.

(40) The powder of embodiment (39), wherein the nonionic surfactant is a polyethylene glycol octadecyl ether of the formula $C_{18}H_{37}(OC_2H_4)_{h'}OH$, wherein h' is an integer ranging from about 2 to about 200.

(41) The powder of embodiment (35), wherein the nonionic surfactant is of Formula XIII:

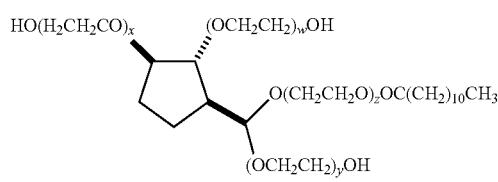

XIII wherein w, x, y, and z are integers from about 0 to about 50, and w, x, y, and z are the same or different.

(42) The powder of embodiment (41), wherein the nonionic surfactant is TWEEN® 20 surfactant, i.e., w+x+y+z=20.

(43) The powder of embodiment (39), wherein the nonionic surfactant is of Formula XII:

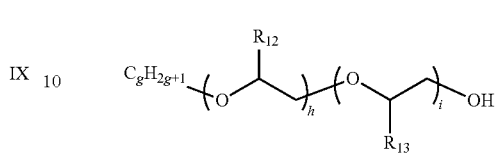

XII wherein g is an integer ranging from about 6 to about 50, i is 0, $R_{12}$ is H, and h is an integer ranging from about 2 to about 30.

(44) The powder of embodiment (43), wherein the nonionic surfactant is polyethoxy (25) lauryl alcohol, polyethoxy (25) cetyl alcohol, polyethoxy (25) stearyl alcohol, polyethoxy (25) behenyl alcohol, or a combination thereof.

(45) The powder of embodiment (44), wherein the nonionic surfactant is a mixture of polyethoxy (25) cetyl alcohol and polyethoxy (25) stearyl alcohol.

(46) The powder of any one of embodiments (1)-(45), wherein the one or more associative polymer(s) comprises a sum total from about 0.005 mol % to about 10 mol % of the one or more associative monomer unit(s).

(47) The powder of embodiment (46), wherein the one or more associative polymer(s) comprises a sum total from about 0.005 mol % to about 0.50 mol % of the one or more associative monomer unit(s).

(48) The powder of embodiment (47), wherein the one or more associative polymer(s) comprises a sum total from about 0.005 mol % to about 0.25 mol % of the one or more associative monomer unit(s).

(49) The powder of any one of embodiments (1)-(48), wherein the one or more associative polymer(s) comprises a sum total from about 90 mol % to about 99.995 mol % of the one or more additional monomer unit(s).

(50) The powder of embodiment (49), wherein the one or more associative polymer(s) comprises a sum total from about 99.5 mol % to about 99.995 mol % of the one or more additional monomer unit(s).

(51) The powder of embodiment (50), wherein the one or more associative polymer(s) comprises a sum total from about 99.75 mol % to about 99.995 mol % of the one or more additional monomer unit(s).

(52) The powder of any one of embodiments (1)-(51), wherein the powder, at a median particle size of at least 300 microns, is completely soluble as up to a 1 wt. % solution in water with stirring by a cage stirrer at 400 rpm within one hour at room temperature.

(53) The powder of embodiments (1)-(27), wherein the powder, at a median particle size of at least 300 microns, is sparingly soluble in water (i.e., did not completely dissolve as a 1 wt. % solution in water within one hour at room temperature).

(54) The powder of any one of embodiments (1)-(53), wherein the one or more associative polymer(s) have a weight average molecular weight of from about 200 kDa to about 2,000 kDa.

(55) The powder of embodiment (54), wherein the one or more associative polymer(s) have a weight average molecular weight of from about 500 kDa to about 2,000 kDa.

(56) The powder of embodiment (55), wherein the one or more associative polymer(s) have a weight average molecular weight of from about 800 kDa to about 2,000 kDa.

(57) The powder of any one of embodiments (1)-(56), wherein the powder has an intrinsic viscosity of from about 0.05 dL/g to about 7 dL/g.

(58) The powder of embodiment (57), wherein the powder has an intrinsic viscosity of from about 0.5 dL/g to about 5 dL/g.

(59) The powder of any one of embodiments (1)-(58), wherein the powder has a Huggins constant of from about 0.3 to about 10.

(60) The powder of embodiment (59), wherein the powder has a Huggins constant of from about 0.3 to about 5.

(61) The powder of any one of embodiments (28)-(60), wherein the powder comprises a sum total from about 0.001 wt. % to about 20 wt. % of the one or more surfactant(s).

(62) The powder of embodiment (28), wherein the powder comprises polyethoxy (25) cetyl and/or stearyl alcohol, and an associative polymer comprising acrylamide, DMAEA.MCQ, and cetyl and/or stearyl polyethoxy (25) methacrylate.

(63) The powder of embodiment (28), wherein the powder comprises polyethoxy (25) cetyl and/or stearyl alcohol, and an associative polymer comprising monomer units derived from acrylamide, sodium acrylate, and cetyl and/or stearyl polyethoxy (25) methacrylate.

(64) The powder of embodiment (28), wherein the powder comprises hexadecyltrimethylammonium p-tolunensulfonate and/or cetyltrimethylammonium chloride, and an associative polymer comprising monomer units derived from acrylamide, DMAEA.MCQ, and Formula VII:

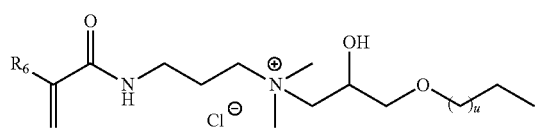

VII wherein $R_6$ is $CH_3$, and u is 10.

(65) The powder of embodiment (28), wherein the powder comprises hexadecyltrimethylammonium p-tolunensulfonate and/or cetyltrimethylammonium chloride, and an associative polymer comprising monomer units derived from acrylamide, sodium acrylate, and Formula VII:

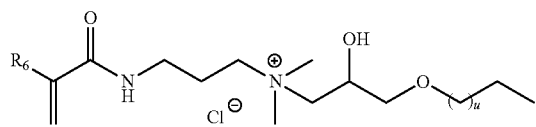

VII wherein $R_6$ is $CH_3$, and u is 10.

(66) An associative polymer of formula $AP_1$:

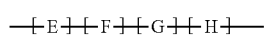

$AP_1$ wherein E is one or more associative monomer unit(s), F is one or more additional monomer unit(s), G is one or more monomer unit(s) derived from a monomer of Formula I, H is optionally present and is one or more piperidine-2,6-dione unit(s), wherein the one or more piperidine-2,6-dione(s) are formed upon cyclization of an acrylamide nitrogen of the monomer unit derived from a monomer of Formula I ("G") on a carbonyl of the additional monomer unit ("F"), and wherein the associative polymer has a weight average molecular weight of from about 10 kDa to about 2,000 kDa.

(67) The associative polymer of embodiment (66), wherein H is not present, and the associative polymer is of the formula $AP_2$:

$AP_2$ wherein E is one or more associative monomer unit(s), E' is a mole percentage value of from about 0.005 to about 10, F is one or more additional monomer unit(s), F' is a mole percentage value of from about 0.005 to about 90, G is one or more monomer unit(s) derived from a monomer of Formula I, and G' is a mole percentage value of from about 10 to about 99.99.

(68) The associative polymer of embodiment (67), wherein E' is from about 0.005 mol % to about 1 mol %, F' is from about 4 mol % to about 16 mol %, and G' is from about 84 mol % to about 96 mol %.

(69) The associative polymer of embodiment (67) or 68), wherein E is a nonionic associative monomer unit.

(70) The associative polymer of embodiment (69), wherein the nonionic associative monomer unit is derived from a monomer of Formula II:

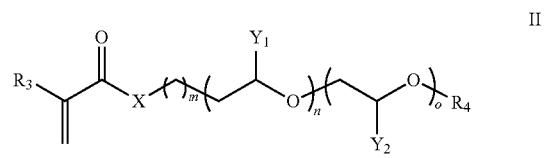

II wherein $R_3$ is H or $C_1$-$C_{10}$ alkyl, X is O or NH, m, n, and o are independently integers from 0 to 100, wherein when $(n+o) \leq 3$, m is at least 7, each $Y_1$ and $Y_2$ are independently H or $C_1$-$C_4$ alkyl, and $R_4$ is H or a hydrophobic group.

(71) The associative polymer of embodiment (70), wherein the nonionic associative monomer unit is derived from a monomer of Formula III:

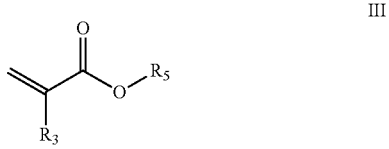

III wherein $R_5$ is —$CH_2(CH_2)_pCH_3$, $R_3$ is H or $C_1$-$C_{10}$ alkyl, and p is an integer from 3 to 100.

(72) The associative polymer of embodiment (71), wherein the nonionic monomer unit is derived from laurylacrylate, cetylacrylate, stearylacrylate, behenylacrylate, or a combination thereof.

(73) The associative polymer of embodiment (72), wherein the nonionic monomer unit is derived from laurylacrylate.

(74) The associative polymer of embodiment (70), wherein the nonionic associative monomer unit is derived from a monomer of Formula IV:

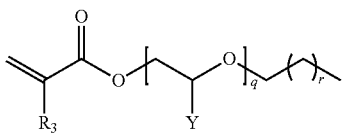

wherein R₃ is H or $C_1$-$C_{10}$ alkyl, q is an integer from 2 to 100, r is an integer from 0 to 30, and each Y is independently H or $CH_3$.

(75) The associative polymer of embodiment (74), wherein the nonionic monomer unit is derived from lauryl polyethoxy (25) methacrylate, cetyl polyethoxy (25) methacrylate, stearyl polyethoxy (25) methacrylate, behenyl polyethoxy (25) methacrylate, or a combination thereof.

(76) The associative polymer of embodiment (75), wherein the nonionic monomer unit is derived from a mixture of cetyl polyethoxy (25) methacrylate and stearyl polyethoxy (25) methacrylate.

(77) The associative polymer of embodiment (67) or (68), wherein E is a cationic associative monomer unit.

(78) The associative polymer of embodiment (77), wherein the cationic associative monomer unit is derived from a monomer of Formula VI:

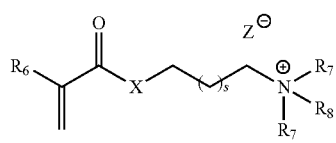

wherein $R_6$ and $R_7$ are each independently H or $C_1$-$C_{10}$ alkyl, X is O or NH, s is an integer from 0 to 20, Z is any anion, and $R_8$ is a hydrophobic group.

(79) The associative polymer of embodiment (78), wherein the cationic associative monomer unit is derived from a monomer of Formula VII:

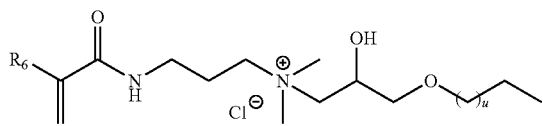

wherein $R_6$ is H or $C_1$-$C_{10}$ alkyl, and u is an integer from 0 to 30.

(80) The associative polymer of embodiment (79), wherein the cationic associative monomer unit is derived from a monomer of Formula VII:

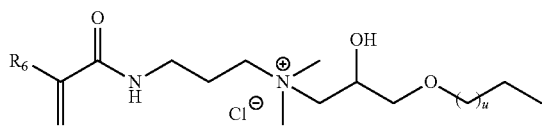

wherein $R_6$ is $CH_3$, and u is 10.

(81) The associative polymer of embodiment (67) or (68), wherein E is an anionic associative monomer unit.

(82) The associative polymer of embodiment (81), wherein the anionic associative monomer unit is derived from a monomer of Formula VIII:

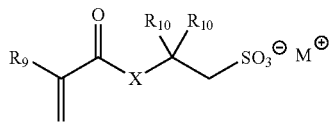

wherein $R_9$ is H or $C_1$-$C_{10}$ alkyl, X is O or NH, M is any cation, and each $R_{10}$ is independently H or a hydrophobic group.

(83) The associative polymer of any one of embodiments (67)-(82), wherein F is derived from a monomer selected from 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

(84) The associative polymer of embodiment (83), wherein F is derived from a monomer selected from diallyldimethylammonium chloride ("DADMAC"), 2-(acryloyloxy)-N,N,N-trimethylethanaminium chloride ("DMAEA.MCQ"), acrylic acid, methacrylic acid, salts thereof, and combinations thereof.

(85) The associative polymer of any one of embodiments (67)-(84), wherein G is derived from a monomer of Formula I:

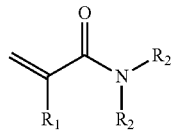

wherein $R_1$ is H or $C_1$-$C_4$ alkyl and each $R_2$ is independently H or an organic group.

(86) The associative polymer of embodiment (85), wherein the organic group is a $C_1$-$C_6$ alkyl group.

(87) The associative polymer of embodiment (86), wherein G is derived from a monomer selected from acrylamide, methacrylamide, or a combination thereof.

(88) The associative polymer of embodiment (66), wherein H is present, and the associative polymer is of the formula $AP_3$:

$$\text{---}[\text{E}]_{E''}[\text{F}]_{F''}[\text{G}]_{G''}[\text{H}]_{H''}\text{---} \qquad AP_3$$

wherein E is one or more associative monomer unit(s), E" is a mole percentage value of from about 0.005 to about 10, F is one or more additional monomer unit(s), F" is a mole percentage value of from about 0.005 to about 90, G is one or more monomer unit(s) derived from a monomer of Formula I, G" is a mole percentage value of from about 10 to about 99.99, H is one or more piperidine-2,6-dione unit(s), and H" is a mole percentage value of from about 0 (i.e., trace amounts) to about 10.

(89) The associative polymer of embodiment (88), wherein H is of the formula

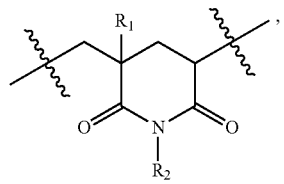

wherein $R_1$ is H or $C_1$-$C_4$ alkyl, and $R_2$ is H or an organic group.

(90) The associative polymer of embodiment (89), wherein the organic group is a $C_1$-$C_6$ alkyl group.

(91) The associative polymer of embodiment (89), wherein $R_1$ and $R_2$ are hydrogen.

(92) The associative polymer of any one of embodiments (88)-(91), wherein E" is from about 0.005 mol % to about 1 mol %, F" is from about 4 mol % to about 10 mol %, G" is from about 84 mol % to about 90 mol %, and H" is from about 0 mol % (i.e., trace amounts) to about 10 mol %.

(93) The associative polymer of any one of embodiments (88)-(92), wherein E is a nonionic associative monomer unit.

(94) The associative polymer of embodiment (93), wherein the nonionic associative monomer unit is derived from a monomer of Formula II:

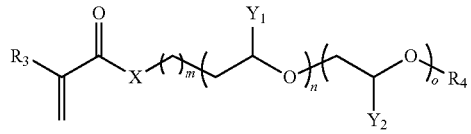

wherein $R_3$ is H or $C_1$-$C_{10}$ alkyl, X is O or NH, m, n, and o are independently integers from 0 to 100, wherein when (n+o)≤3, m is at least 7, each $Y_1$ and $Y_2$ are independently H or $C_1$-$C_4$ alkyl, and $R_4$ is H or a hydrophobic group.

(95) The associative polymer of embodiment (94), wherein the nonionic associative monomer unit is derived from a monomer of Formula III:

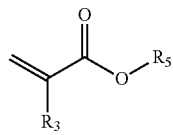

wherein $R_5$ is —$CH_2(CH_2)_pCH_3$, $R_3$ is H or $C_1$-$C_{10}$ alkyl, and p is an integer from 3 to 100.

(96) The associative polymer of embodiment (95), wherein the nonionic monomer unit is derived from laurylacrylate, cetylacrylate, stearylacrylate, behenylacrylate, or a combination thereof.

(97) The associative polymer of embodiment (96), wherein the nonionic monomer unit is derived from laurylacrylate.

(98) The associative polymer of embodiment (93), wherein the nonionic associative monomer unit is derived from a monomer of Formula IV:

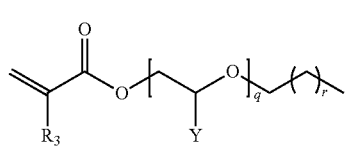

wherein $R_3$ is H or $C_1$-$C_{10}$ alkyl, q is an integer from 2 to 100, r is an integer from 0 to 30, and each Y is independently H or $CH_3$.

(99) The associative polymer of embodiment (94), wherein the nonionic associative monomer unit is derived from lauryl polyethoxy (25) methacrylate, cetyl polyethoxy (25) methacrylate, stearyl polyethoxy (25) methacrylate, behenyl polyethoxy (25) methacrylate, or a combination thereof.

(100) The associative polymer of embodiment (99), wherein the nonionic monomer unit is derived from a mixture of cetyl polyethoxy (25) methacrylate and stearyl polyethoxy (25) methacrylate.

(101) The associative polymer of any one of embodiments (88)-(92), wherein E is a cationic associative monomer unit.

(102) The associative polymer of embodiment (101), wherein the cationic associative monomer unit is derived from a monomer of Formula VI:

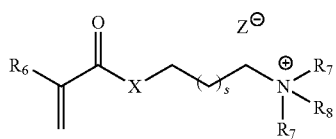

wherein $R_6$ and $R_7$ are each independently H or $C_1$-$C_{10}$ alkyl, X is O or NH, s is an integer from 0 to 20, Z is any anion, and $R_8$ is a hydrophobic group.

(103) The associative polymer of embodiment (102), wherein the cationic associative monomer unit is derived from a monomer of Formula VII:

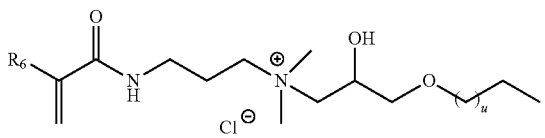

wherein $R_6$ is H or $C_1$-$C_{10}$ alkyl, and u is an integer from 0 to 30.

(104) The associative polymer of embodiment (103), wherein the cationic associative monomer unit is derived from a monomer of Formula VII:

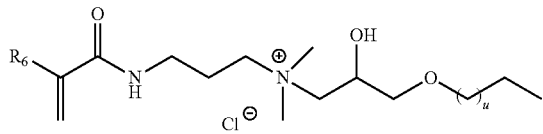

wherein $R_6$ is $CH_3$, and u is 10.

(105) The associative polymer of any one of embodiments (88)-(92), wherein E is an anionic associative monomer unit.

(106) The associative polymer of embodiment (105), wherein the anionic associative monomer unit is derived from a monomer of Formula VIII:

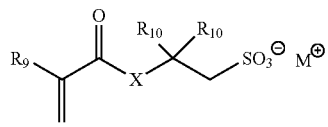

wherein $R_9$ is H or $C_1$-$C_{10}$ alkyl, X is O or NH, M is any cation, and each $R_{10}$ is independently H or a hydrophobic group.

(107) The associative polymer of any one of embodiments (88)-(106), wherein G is derived from a monomer of Formula I:

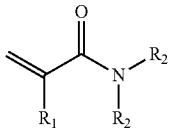

wherein $R_1$ is H or $C_1$-$C_4$ alkyl and each $R_2$ is independently H or an organic group.

(108) The associative polymer of embodiment (107), wherein the organic group is a $C_1$-$C_6$ alkyl group.

(109) The associative polymer of embodiment (107), wherein G is derived from acrylamide.

(110) The associative polymer of embodiment (108), wherein G is derived from methacrylamide.

(111) The associative polymer of any one of embodiments (88)-(110), wherein F is derived from a monomer selected from 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

(112) The associative polymer of embodiment (111), wherein F is a cationic monomer unit derived from a monomer selected from 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), salts thereof, and combinations thereof.

(113) The associative polymer of embodiment (112), wherein F is derived from 2-(acryloyloxy)-N,N,N-trimethylethanaminium chloride ("DMAEA.MCQ").

(114) The associative polymer of embodiment (112), wherein the additional monomer unit is derived from diallyldimethylammonium chloride ("DADMAC").

(115) The associative polymer of embodiment (111), wherein F is an anionic monomer unit derived from a monomer selected from 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

(116) The associative polymer of embodiment (115), wherein F is derived from acrylic acid.

(117) The associative polymer of embodiment (115), wherein F is derived from sodium acrylate.

(118) The associative polymer of any one of embodiments (66)-(117), wherein the associative polymer has a weight average molecular weight of from about 200 kDa to about 2,000 kDa.

(119) The associative polymer of embodiment (118), wherein the associative polymer has a weight average molecular weight of from about 500 kDa to about 2,000 kDa.

(120) The associative polymer of embodiment (119), wherein the associative polymer has a weight average molecular weight of from about 800 kDa to about 2,000 kDa.

(121) The associative polymer of embodiment (88), wherein the associative polymer is of the formula $AP_4$:

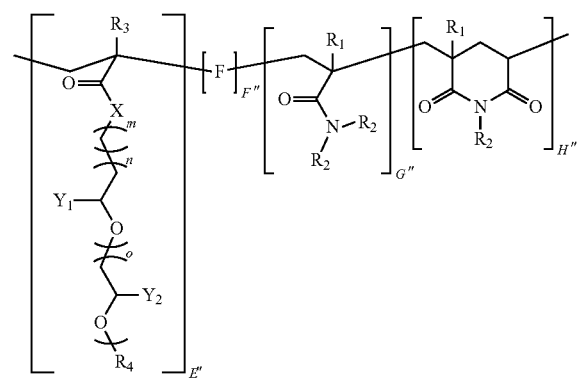

wherein each $R_1$ is independently H or $C_1$-$C_4$ alkyl, each $R_2$ is independently H or an organic group, $R_3$ is H or $C_1$-$C_{10}$ alkyl, X is O or NH, m, n, and o are independently integers from 0 to 100, wherein when (n+o)≤3, m is at least 7, each $Y_1$ and $Y_2$ are independently H or $C_1$-$C_4$ alkyl, and $R_4$ is H or a hydrophobic group.

(122) The associative polymer of embodiment (88), wherein the associative polymer is of the formula $AP_6$:

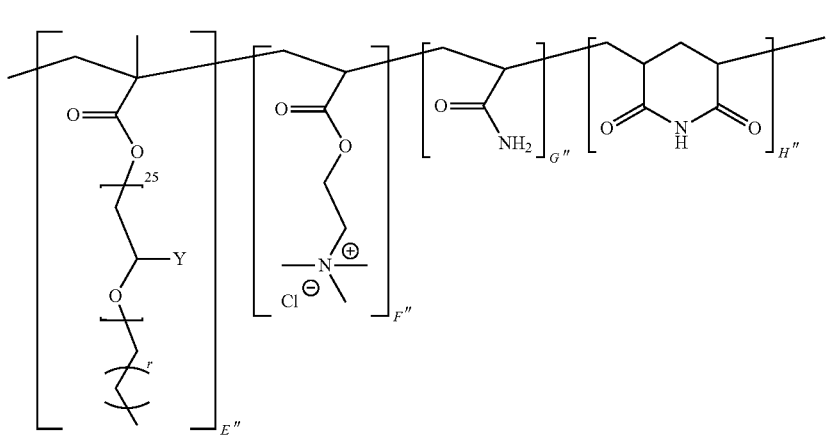

wherein r is an integer from 0 to 30 and each Y is independently H or CH$_3$.

(123) The associative polymer of embodiment (88), wherein the associative polymer is of the formula AP$_7$:

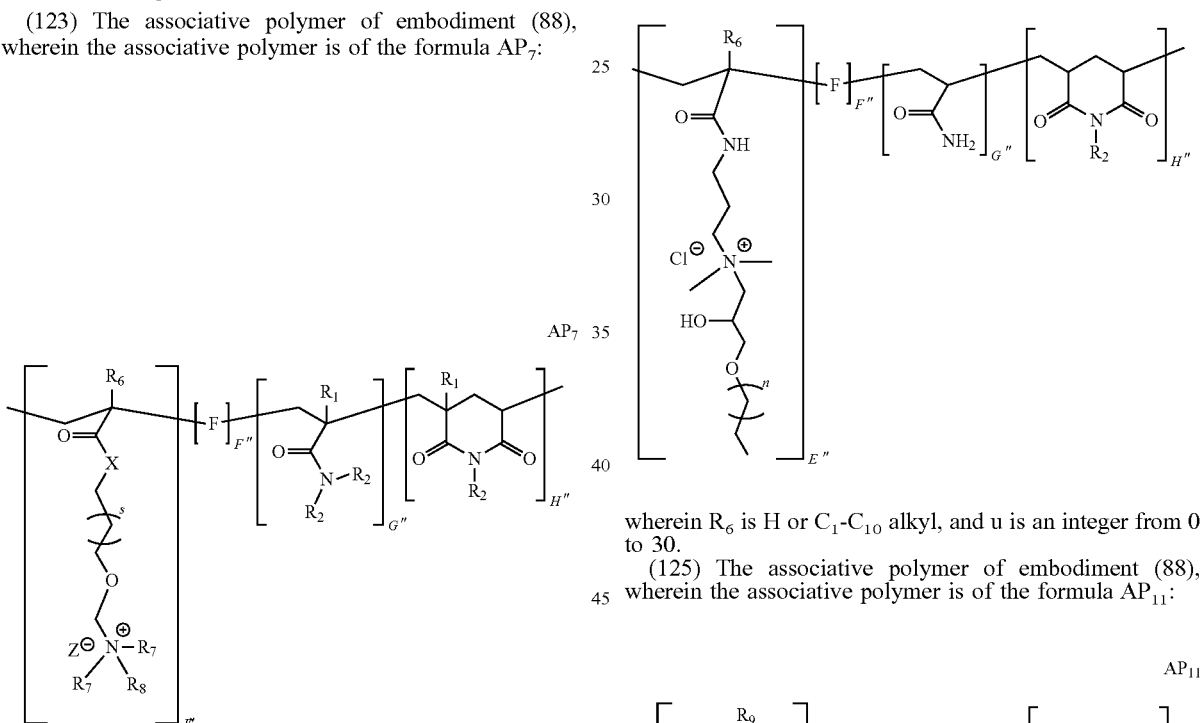

wherein each R$_1$ is independently H or C$_1$-C$_4$ alkyl, each R$_2$ is independently H or an organic group, R$_6$ and R$_7$ are each independently H or C$_1$-C$_{10}$ alkyl, X is O or NH, s is an integer from 0 to 20, Z is any anion, and R$_8$ is a hydrophobic group.

(124) The associative polymer of embodiment (88), wherein the associative polymer is of the formula AP$_9$:

wherein R$_6$ is H or C$_1$-C$_{10}$ alkyl, and u is an integer from 0 to 30.

(125) The associative polymer of embodiment (88), wherein the associative polymer is of the formula AP$_{11}$:

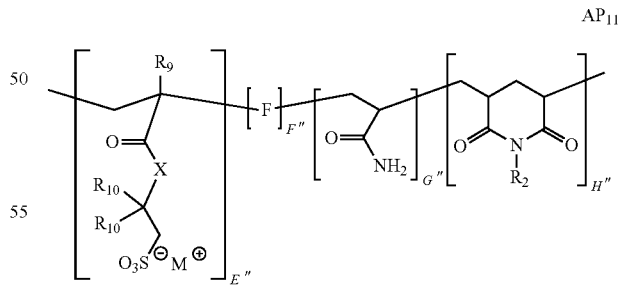

wherein R$_9$ is H or C$_1$-C$_{10}$ alkyl, X is O or NH, M is any cation, and each R$_{10}$ is independently H or a hydrophobic group.

(126) A process for making a powder, comprising forming a powder from a wet gel, wherein the wet gel comprises one or more associative polymer(s), and optionally one or more surfactant(s), wherein the one or more associative polymer(s) have a weight average molecular weight of from about 10 kDa to about 2,000 kDa.

(127) The process of embodiment (126), wherein the wet gel is machine processed to a powder.

(128) The process of embodiment (126) or (127), wherein the one or more associative polymer(s) comprises one or more associative monomer(s) unit derived from an acrylate monomer, acrylamide monomer, or a combination thereof.

(129) The process of any one of embodiments (126)-(128), wherein the one or more associative polymer(s) comprises a nonionic associative monomer unit.

(130) The process of embodiment (129), wherein the nonionic associative monomer unit is derived from a monomer of Formula II:

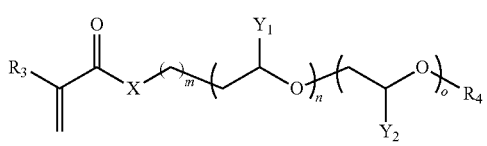

wherein $R_3$ is H or $C_1$-$C_{10}$ alkyl, X is O or NH, m, n, and o are independently integers from 0 to 100, wherein when (n+o)≤3, m is at least 7, each $Y_1$ and $Y_2$ are independently H or $C_1$-$C_4$ alkyl, and $R_4$ is H or a hydrophobic group.

(131) The process of embodiment (130), wherein the nonionic associative monomer unit is derived from a monomer of Formula III:

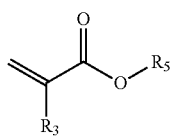

wherein $R_5$ is —$CH_2(CH_2)_pCH_3$, $R_3$ is H or $C_1$-$C_{10}$ alkyl, and p is an integer from 3 to 100.

(132) The process of embodiment (131), wherein the nonionic monomer unit is derived from laurylacrylate, cetylacrylate, stearylacrylate, behenylacrylate, or a combination thereof.

(133) The process of embodiment (132), wherein the nonionic monomer unit is derived from laurylacrylate.

(134) The process of embodiment (130), wherein the nonionic associative monomer unit is derived from a monomer of Formula IV:

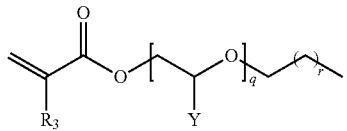

wherein $R_3$ is H or $C_1$-$C_{10}$ alkyl, q is an integer from 2 to 100, r is an integer from 0 to 30, and each Y is independently H or $CH_3$.

(135) The process of embodiment (132), wherein the nonionic monomer unit is derived from lauryl polyethoxy (25) methacrylate, cetyl polyethoxy (25) methacrylate, stearyl polyethoxy (25) methacrylate, behenyl polyethoxy (25) methacrylate, or a combination thereof.

(136) The process of embodiment (135), wherein the nonionic monomer unit is derived from a mixture of cetyl polyethoxy (25) methacrylate and stearyl polyethoxy (25) methacrylate.

(137) The process of any one of embodiments (126)-(128), wherein the one or more associative polymer(s) comprises a cationic associative monomer unit.

(138) The process of embodiment (137), wherein the cationic associative monomer unit is derived from a monomer of Formula VI:

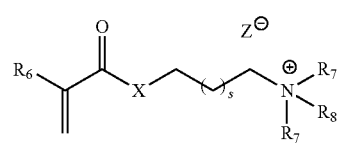

wherein $R_6$ and $R_7$ are each independently H or $C_1$-$C_{10}$ alkyl, X is O or NH, s is an integer from 0 to 20, Z is any anion, and $R_8$ is a hydrophobic group.

(139) The process of embodiment (138), wherein the cationic associative monomer unit is derived from a monomer of Formula VII:

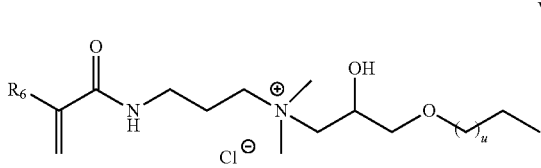

wherein $R_6$ is H or $C_1$-$C_{10}$ alkyl, and u is an integer from 0 to 30.

(140) The process of embodiment (139), wherein the cationic associative monomer unit is derived from a monomer of Formula VII:

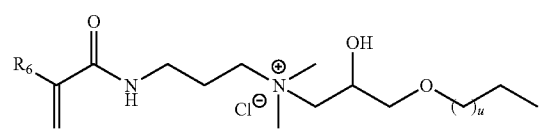

wherein $R_6$ is $CH_3$, and u is 10.

(141) The process of any one of embodiments (126)-(128), wherein the one or more associative polymer(s) comprises an anionic associative monomer unit.

(142) The process of embodiment (141), wherein the anionic associative monomer unit is derived from a monomer of Formula VIII:

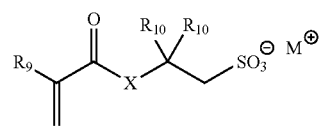

wherein $R_9$ is H or $C_1$-$C_{10}$ alkyl, X is O or NH, M is any cation, and each $R_{10}$ is independently H or a hydrophobic group.

(143) The process of any one of embodiments (126)-(142), wherein the one or more associative polymer(s) comprise one or more additional monomer unit(s) selected from a cationic monomer unit, an anionic monomer unit, a nonionic monomer unit, and a combination thereof.

(144) The process of embodiment (143), wherein the additional monomer unit is derived from a monomer selected from a monomer of Formula I:

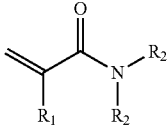

wherein $R_1$ is H or $C_1$-$C_4$ alkyl and each $R_2$ is independently H or an organic group; 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino] propyl]-phosphonic acid, methacrylic acid, acrylic acid; salts thereof; and combinations thereof.

(145) The process of embodiment (143) or (144), wherein the additional monomer unit is derived from a monomer of Formula I:

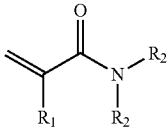

wherein $R_1$ is H or $C_1$-$C_4$ alkyl and each $R_2$ is independently H or an organic group.

(146) The process of embodiment (145), wherein the organic group is a $C_1$-$C_6$ alkyl group.

(147) The process of embodiment (145), wherein the additional monomer unit is derived from acrylamide.

(148) The process of embodiment (146), wherein the additional monomer unit is derived from methacrylamide.

(149) The process of embodiment (144), wherein the additional monomer unit is a cationic monomer unit derived from a monomer selected from 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), diallyldimethylammonium chloride ("DADMAC"), diallylamine, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), salts thereof, and combinations thereof.

(150) The process of embodiment (149), wherein the additional monomer unit is derived from 2-(acryloyloxy)-N,N,N-trimethylethanaminium chloride ("DMAEA.MCQ").

(151) The process of embodiment (149), wherein the additional monomer unit is derived from diallyldimethylammonium chloride ("DADMAC").

(152) The process of embodiment (144), wherein the additional monomer unit is an anionic monomer unit derived from a monomer selected from 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

(153) The process of embodiment (152), wherein the additional monomer unit is derived from acrylic acid.

(154) The process of embodiment (152), wherein the additional monomer unit is derived from sodium acrylate.

(155) The process of any one of embodiments (126)-(154), wherein the wet gel comprises one or more surfactant(s).

(156) The process of embodiment (155), wherein the surfactant is an anionic surfactant.

(157) The process of embodiment (156), wherein the anionic surfactant is a sulfate salt of Formula X:

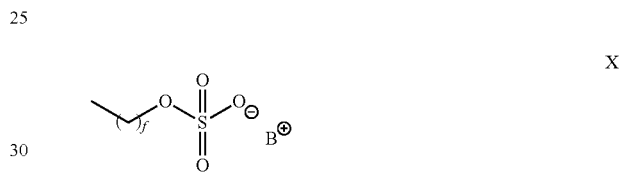

wherein B is any cation, and f is an integer from 7 to 35.

(158) The process of embodiment (157), wherein the anionic surfactant is sodium dodecylsulfate.

(159) The process of embodiment (155), wherein the surfactant is a cationic surfactant.

(160) The process of embodiment (159), wherein the cationic surfactant is an ammonium salt of Formula IX:

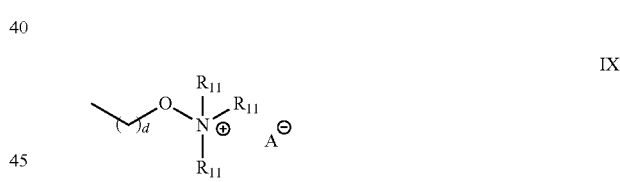

wherein each $R_{11}$ is independently H or $C_1$-$C_{10}$ alkyl, A is any anion, and d is an integer from 6 to 34.

(161) The process of embodiment (160), wherein the cationic surfactant is hexadecyltrimethylammoniump-tolunesulfonate, hexadecyltrimethylammonium chloride, or a combination thereof.

(162) The process of embodiment (155), wherein the surfactant is nonionic.

(163) The process of embodiment (162), wherein the nonionic surfactant is a block or random polymer comprising ethylene oxide, propylene oxide, or a combination thereof.

(164) The process of embodiment (163), wherein the polymer is of Formula XI:

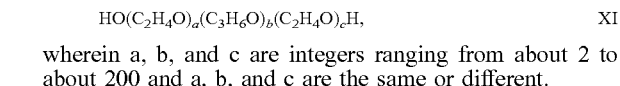

wherein a, b, and c are integers ranging from about 2 to about 200 and a, b, and c are the same or different.

(165) The process of embodiment (164), wherein the nonionic surfactant is HO(C$_2$H$_4$O)$_{101}$(C$_3$H$_6$O)$_{56}$(C$_2$H$_4$O)$_{101}$H.

(166) The process of embodiment (165), wherein the nonionic surfactant is of Formula XII:

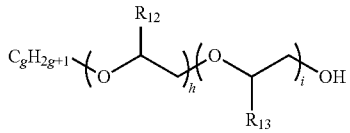

wherein g is an integer ranging from about 6 to about 50, each $R_{12}$ and $R_{13}$ are independently H or $C_1$-$C_4$ alkyl, and h and i are independently integers ranging from 0 to about 100.

(167) The process of embodiment (166), wherein the nonionic surfactant is a polyethylene glycol octadecyl ether of the formula $C_{18}H_{37}(OC_2H_4)_{h'}OH$, wherein h' is an integer ranging from about 2 to about 200.

(168) The process of embodiment (162), wherein the nonionic surfactant is of Formula XIII:

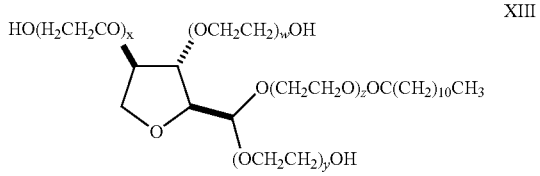

wherein w, x, y, and z are integers from about 0 to about 50, and w, x, y, and z are the same or different.

(169) The process of embodiment (168), wherein the nonionic surfactant is TWEEN® 20 surfactant, i.e., w+x+y+z=20.

(170) The process of embodiment (166), wherein the nonionic surfactant is of Formula XII:

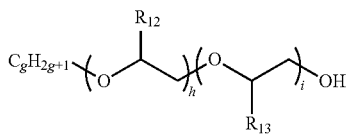

wherein g is an integer ranging from about 6 to about 50, i is 0, $R_{12}$ is H, and h is an integer ranging from about 2 to about 30.

(171) The process of embodiment (170), wherein the nonionic surfactant is polyethoxy (25) lauryl alcohol, polyethoxy (25) cetyl alcohol, polyethoxy (25) stearyl alcohol, polyethoxy (25) behenyl alcohol, or a combination thereof.

(172) The process of embodiment (171), wherein the nonionic surfactant is a mixture of polyethoxy (25) cetyl alcohol and polyethoxy (25) stearyl alcohol.

(173) The process of any one of embodiments (155)-(172), wherein the one or more associative polymer(s) are formed in the presence of a surfactant.

(174) The process of any one of embodiments (126)-(172), wherein the one or more associative polymer(s) are formed in the absence of a surfactant.

(175) The process of embodiment (174), wherein one or more surfactant(s) are added to the powder.

(176) The process of any one of embodiments (126)-(175), wherein the powder, at a median particle size of at least 300 microns, is completely soluble as up to a 1 wt. % solution in water with stirring by a cage stirrer at 400 rpm within one hour at room temperature.

(177) The process of any one of embodiments (126)-(154), wherein the powder, at a median particle size of at least 300 microns, is sparingly soluble in water (i.e., did not completely dissolve as a 1 wt. % solution in water within one hour at room temperature).

(178) The process of any one of embodiments (126)-(177), wherein the one or more associative polymer(s) have a weight average molecular weight of from about 200 kDa to about 2,000 kDa.

(179) The process of embodiment (178), wherein the one or more associative polymer(s) have a weight average molecular weight of from about 500 kDa to about 2,000 kDa.

(180) The process of embodiment (179), wherein the one or more associative polymer(s) have a weight average molecular weight of from about 800 kDa to about 2,000 kDa.

(181) The process of any one of embodiments (126)-(180), wherein the powder has an intrinsic viscosity of from about 0.05 dL/g to about 7 dL/g.

(182) The process of embodiment (181), wherein the powder has an intrinsic viscosity of from about 0.5 dL/g to about 5 dL/g.

(183) The process of any one of embodiments (126)-(182), wherein the powder has a Huggins constant of from about 0.3 to about 10.

(184) The process of embodiment (183), wherein the powder has a Huggins constant of from about 0.3 to about 5.

The following examples further illustrate the invention but, of course, should not be construed as in any way limiting its scope.

Example 1

This example, provided as a control, demonstrates the effect on the inability to be machine processed into a powder, exhibited by a low molecular weight polymer without networking via an associative monomer unit or a surfactant.

Polymer 1 (control) comprising 95/5 mol % acrylamide/DMAEA.MCQ was synthesized in the following manner:

An 1,000 g aqueous solution at pH 2-5 containing 34 wt. % monomer mixture of 95/5 mol % acrylamide/DMAEA.MCQ, azo initiator, chain transfer agent, buffer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1 \times 10^6$ g/mol. The resulting polymer gel was too soft and sticky to be processed with the aid of 1 wt. % (relative to weight of polymer gel) petroleum oil based lubricant in a cutting mill (Restch Mill Cutter) at 1500 rpm. The resulting polymer gel was manually divided into small pieces on a tray and dried in an oven at 85° C. to remove the moisture and then ground to powder with an intrinsic viscosity of 3.20 dg/L and Huggins constant of 0.31 in 1.0 N $NaNO_3$ solution at 30° C. The weight average molecular weight was determined by hydrolysis (using 0.1 wt. % solution of NaOH at pH 12 with a cage stirrer at 400 rpm for one hour) of the resulting polymer, followed by size exclusion chromatography.

As is apparent from the results set forth in Table 1, low molecular weight Polymer 1, lacking temporary networking via an associative monomer, was incapable of being machine processed to form a powder. This was further evidenced by the procedure requiring manual division of the soft and sticky polymer.

TABLE 1

| Polymer | Intrinsic Viscosity (dg/L) | Huggins Constant | Weight Average Molecular Weight (kDa) | Wet Gel Processable |
|---|---|---|---|---|
| 1 | 3.20 | 0.31 | 930 | No |
| 2 | 2.91 | 1.05 | 820 | Yes |
| 3 | 1.96 | 1.36 | 490 | Yes |

Example 2

This example demonstrates the effect on the ability to be machine processed into a powder, exhibited by a low molecular weight polymer comprising temporary networking via an associative monomer unit and a surfactant.

Polymer 2 comprising 94.94/5/0.06 mol % acrylamide/DMAEA.MCQ/C18PEG1105MA was synthesized in the following manner:

An 1,000 g aqueous solution at pH 2-5 containing 34 wt. % monomer mixture of 94.94/5/0.06 mol % acrylamide/DMAEA.MCQ/C18PEG1105MA (VISIOMER® monomer; 55% active; Evonik Industries, Essen, Germany), 1 wt. % of PLURONIC® F127 surfactant (BASF Corporation, Florham Park, N.J.), azo initiator, chain transfer agent, buffer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1\times10^6$ g/mol. The resulting wet gel, which maintained a taffy like consistency and was not sticky, was processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to decrease the moisture content to about 10 wt. % and then ground to powder having an intrinsic viscosity of 2.91 dg/L and Huggins constant of 1.05 in 1 N NaNO$_3$ solution at 30° C. The weight average molecular weight was determined by hydrolysis (using 0.1 wt. % solution of NaOH at pH 12 with a cage stirrer at 400 rpm for one hour) of the resulting polymer, followed by size exclusion chromatography.

As is apparent from the results set forth in Table 1, low molecular weight Polymer 2, comprising temporary networking, was capable of being machine processed to form a powder. This was further evidenced by the procedure allowing for use of a cutting mill to process the wet gel.

Example 3

This example demonstrates the effect on the ability to be processed into a powder, exhibited by a low molecular weight polymer comprising temporary networking via an associative monomer unit and surfactant.

Polymer 3 comprising 94.84/5/0.12 mol % acrylamide/DMAEA.MCQ/C18PEG1105MA was synthesized in the following manner:

An 1,000 g aqueous solution at pH 2-5 containing 34 wt. % monomer mixture of 94.8/5/0.12 mol % acrylamide/DMAEA.MCQ/C18PEG1105MA (VISIOMER® monomer; 55% active; Evonik Industries, Essen, Germany), 1 wt. % of PLURONIC® F127 surfactant (BASF Corporation, Florham Park, N.J.), azo initiator, chain transfer agent, buffer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $0.5\times10^6$ g/mol. The resulting wet gel, which maintained a taffy like consistency and was not sticky, was processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to decrease the moisture content to about 10 wt. % and then ground to powder having an intrinsic viscosity of 1.96 dg/L and Huggins constant of 1.36 in 1 N NaNO$_3$ solution at 30° C. The weight average molecular weight was determined by hydrolysis (using 0.1 wt. % solution of NaOH at pH 12 with a cage stirrer at 400 rpm for one hour) of the resulting polymer, followed by size exclusion chromatography.

As is apparent from the results set forth in Table 1, low molecular weight Polymer 3, comprising temporary networking, was capable of being machine processed to form a powder. This was further evidenced by the procedure allowing for use of a cutting mill to process the wet gel.

Example 4

This example demonstrates the effect on the ability to be machine processed into a powder, exhibited by a low molecular weight polymer comprising temporary networking via an associative monomer unit only (i.e., not further comprising a surfactant in the monomer phase).

Polymer 4 comprising 89.965/10/0.035 mol % acrylamide/DMAEA.MCQ/C18PEG1105MA was synthesized in the following manner:

An 1,000 g aqueous solution at pH 2-5 containing 37 wt. % monomer mixture of 89.965/10/0.035 mol % acrylamide/DMAEA.MCQ/C18PEG1105MA (VISIOMER® monomer; 55% active; Evonik Industries, Essen, Germany), azo initiator, chain transfer agent, buffer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1.0\times10^6$ g/mol. The resulting wet gel, which maintained a taffy like consistency and was not sticky, was marginally processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to decrease the moisture content to about 10 wt. % and then ground to powder. The resulting powder had a median particle size of 568.9 microns (the mean particle size was 634.4), as determined using a Horiba Laser Scattering Particle Size Distribution Analyzer LA-950 with the setting of refractive index of powder at 1.5000. The powder did not completely dissolve as a 1 wt. % solution in synthetic tap water with stirring of cage stirrer at 400 rpm within one hour. The powder, as a 1 wt. % solution in synthetic tap water, had a viscosity of 744 cps, as measured on a Brookfield Model DV-E Viscometer with Spindle 62 at 30 rpm. The weight average molecular weight was determined by hydrolysis (using 0.1 wt. % solution of NaOH at pH 12 with a cage stirrer at 400 rpm for one hour) of the resulting polymer, followed by size exclusion chromatography.

As is apparent from the results set forth in Table 2, low molecular weight Polymer 4, not comprising a surfactant, was marginally capable of being machine processed to form a powder. The resulting powder was sparingly soluble in water (i.e., did not completely dissolve as a 1 wt. % solution in local tap water with stirring of cage stirrer at 400 rpm within one hour).

TABLE 2

| Polymer | Weight Average MW (kDa) | Surfactant in powder (wt. %) | Wet Gel Processable | Solubility | Viscosity of 1 wt. % solution in water (cps) |
|---|---|---|---|---|---|
| 4 | 840 | 0 | Yes (marginal) | Poor | 744 |
| 5 | 930 | 2.2 | Yes | Good | 317 |

Example 5

This example demonstrates the effect on the ability to be machine processed into a powder, exhibited by a low molecular weight polymer comprising temporary networking via an associative monomer unit and surfactant.

Polymer 5 comprising 89.965/10/0.035 mol % acrylamide/DMAEA.MCQ/C18PEG1105MA was synthesized in the following manner:

An 1,000 g aqueous solution at pH 2-5 containing 37 wt. % monomer mixture of 89.965/10/0.035 mol % acrylamide/DMAEA.MCQ/C18PEG1105MA (VISIOMER® monomer; 55% active; Evonik Industries, Essen, Germany), 1 wt. % LutensolAT® 25 surfactant, or ethoxylated (25 mol EO) C16-18 fatty alcohol (BASF Corporation, Florham Park, N.J.), azo initiator, chain transfer agent, buffer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1.0 \times 10^6$ g/mol. The resulting wet gel, which maintained a taffy like consistency and was not sticky, was processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to decrease the moisture content to about 10 wt. % and then ground to powder. The resulting powder had a median particle size of 559.7 microns (the mean particle size was 609.3), as determined using a Horiba Laser Scattering Particle Size Distribution Analyzer LA-950 with the setting of refractive index of powder at 1.5000. The powder completely dissolved as a 1 wt. % solution in synthetic tap water with stirring of cage stirrer at 400 rpm within one hour. The powder polymer, as a 1 wt. % solution in synthetic tap water, had a viscosity of 317 cps, as measured on a Brookfield Model DV-E Viscometer with Spindle 62 at 30 rpm. The weight average molecular weight was determined by hydrolysis (using 0.1 wt. % solution of NaOH at pH 12 with a cage stirrer at 400 rpm for one hour) of the resulting polymer, followed by size exclusion chromatography. The structure of Polymer 5 was further analyzed by $^{13}C$ NMR spectroscopy (FIG. 1) to quantify the amount of piperidine-2,6-dione present in the polymer. The $^{13}C$ NMR sample was prepared in deuterated water and the carbon spectrum was acquired using an Agilent Inova 500 Mhz spectrometer equipped with a Z-gradient and broadband 10 mm probe.

As is apparent from the results set forth in Table 2, low molecular weight Polymer 5, comprising a surfactant, was easily machine processed to form a powder. In addition, the resulting powder, comprising 2.2 wt. % surfactant, was completely soluble as a 1 wt. % solution in local tap water with stirring of cage stirrer at 400 rpm within one hour.

In addition, the presence of the piperidine-2,6-dione monomer unit can be verified by $^{13}C$ NMR spectroscopy with a signature peak at 177 ppm in the $^{13}C$ NMR spectrum (FIG. 1). The relative amount of the piperidine-2,6-dione monomer unit can be quantified by integration of the peak at 177 ppm, followed by a relative comparison to the integration of other $^{13}C$ NMR signals indicative of other monomer units. Integration analysis demonstrates that Polymer 5 comprises 7.8/90/2.1 mol % DMAEA.MCQ-acrylamide-piperidine-2,6-dione. Note that the associative monomer unit is present in such low concentrations that signature peaks of the associative monomer unit are not visible by $^{13}C$ NMR spectroscopy.

Example 6

This example, provided as a control, demonstrates the effect on the inability to be machine processed into a powder, exhibited by a low molecular weight polymer without networking via an associative monomer unit or a surfactant.

Polymer 6 (control) comprising 50/50 mol % acrylamide/sodium acrylate was synthesized in the following manner:

An 1,000 g aqueous solution at neutral pH containing 37 wt. % monomer mixture of 50/50 mol % acrylamide/sodium acrylate, azo initiator, chain transfer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1.0 \times 10^6$ g/mol. The resulting polymer wet gel was too soft and sticky to be processed with the aid of 1 wt. % (relative to weight of polymer gel) petroleum oil based lubricant in a cutting mill (Retsch Mill Cutter) at 1500 rpm. The resulting wet gel was manually divided small pieces on a tray and dried in an oven at 85° C. to remove the moisture and then ground to powder with an intrinsic viscosity of 5.80 dg/L and Huggins constant of 0.24 in 1 N $NaNO_3$ solution at 30° C. The weight average molecular weight was determined by size exclusion chromatography.

As is apparent from the results set forth in Table 3, low molecular weight Polymer 6, lacking temporary networking via an associative monomer unit, was incapable of being machine processed to form a powder. This was further evidenced by the procedure requiring manual division of the soft and sticky polymer.

TABLE 3

| Polymer | Intrinsic Viscosity (dg/L) | Huggins Constant | Weight Aveargde MW of Surrogate (kDa) | Wet Gel Processable |
|---|---|---|---|---|
| 6 | 5.80 | 0.24 | 1,100 | No |
| 7 | 5.83 | 0.84 | 1,100 | Yes |
| 8 | 3.49 | 2.49 | 1,100 | Yes |
| 9 | 5.84 | 0.98 | 1,100 | Yes |

Example 7

This example demonstrates the effect on the ability to be machine processed into a powder, exhibited by a low molecular weight polymer comprising temporary networking via an associative monomer unit and surfactant.

Polymer 7 comprising 49.9/50/0.1 mol % acrylamide/sodium acrylate/MAPTAC-C12 derivative synthesized in the following manner:

An 1,000 g aqueous solution at neutral pH containing 37 wt. % monomer mixture of 49.9/50/0.1 mol % acrylamide/sodium acrylate/MAPTAC-C12 derivative, 0.5 wt. % of hexadecyltrimethylammonium p-toluenesulfonate (Sigma-Aldrich, St. Louis, Mo.), azo initiator, chain transfer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1.0 \times 10^6$ g/mol. The resulting wet gel, which maintained a taffy like consistency and was not sticky, was processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to decrease the moisture content to about 10 wt. % and then ground to powder. The resulting powder had a median particle size of 357.1 microns (the mean particle size was 420.1), as determined using a Horiba Laser Scattering Particle Size Distribution Analyzer LA-950 with the setting of refractive index of powder at 1.5000. The powder had an intrinsic viscosity of 5.83 dg/L and Huggins constant of 0.84 in 1.0 N $NaNO_3$ solution at 30° C. The powder completely dissolved as a 1 wt. % solution in synthetic tap water with stirring of cage stirrer at 400 rpm within one hour. The powder, as a 1 wt. % solution in synthetic tap water, had a viscosity of 1976 cps, as measured on a Brookfield Model DV-E Viscometer with Spindle 63 at 30 rpm. The weight average molecular weight was determined by size exclusion chromatography using surrogate, Polymer 6.

As is apparent from the results set forth in Table 3, low molecular weight Polymer 7, comprising a surfactant, was easily machine processed to form a powder. In addition, Table 4 shows that the resulting powder, comprising 1.3 wt. % surfactant, was completely soluble as a 1 wt. % solution in local tap water with stirring of cage stirrer at 400 rpm within one hour.

Example 8

This example demonstrates the effect on the ability to be machine processed into a powder, exhibited by a low molecular weight polymer comprising temporary networking via an associative monomer unit and a surfactant.

Polymer 8 comprising 89.9/10/0.1 mol % acrylamide/ sodium acrylate/MAPTAC-C12 derivative synthesized in the following manner:

An 1,000 g aqueous solution at neutral pH containing 33 wt. % monomer mixture of 89.9/10/0.1 mol % acrylamide/ sodium acrylate/MAPTAC-C12 derivative, 0.5 wt. % of hexadecyltrimethylammonium p-toluenesulfonate (Sigma-Aldrich, St. Louis, Mo.), azo initiator, chain transfer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1.0 \times 10^6$ g/mol. The resulting wet gel, which maintained a taffy like consistency and was not sticky, was processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to decrease the moisture content to about 10 wt. % and then ground to powder. The resulting powder had a median particle size of 396.2 microns (the mean particle size was 463.6), as determined using a Horiba Laser Scattering Particle Size Distribution Analyzer LA-950 with the setting of refractive index of powder at 1.5000. The powder had an intrinsic viscosity of 3.49 dg/L and Huggins constant of 2.49 in 1 N $NaNO_3$ solution at 30° C. The powder completely dissolved as a 1 wt. % solution in synthetic tap water with stirring of cage stirrer at 400 rpm within one hour. The powder, as a 1 wt. % solution in tap water, had a viscosity of 2748 cps, as measured on a Brookfield Model DV-E Viscometer with Spindle 63 at 30 rpm. The weight average molecular weight was determined by size exclusion chromatography using a surrogate polymer formed with the same synthetic procedure containing 90/10 mol % acrylamide/sodium acrylate in the absence of the MAPTAC-C12 derivative.

As is apparent from the results set forth in Table 3, low molecular weight Polymer 8, comprising a surfactant, was easily machine processed to form a powder. In addition, Table 4 shows that the resulting powder, comprising 1.3 wt. % surfactant, was completely soluble as a 1 wt. % solution in local tap water with stirring of cage stirrer at 400 rpm within one hour.

TABLE 4

| Polymer | Weight Avearge MW of Surrogate (kDa) | Surfactant in powder (wt. %) | Wet Gel Processable | Solubility | Viscosity of 1 wt. % solution in water (cps) |
| --- | --- | --- | --- | --- | --- |
| 7 | 1,100 | 1.3 | Yes | Good | 1976 |
| 8 | 1,100 | 1.3 | Yes | Good | 2748 |
| 9 | 1,100 | 0 | Yes | Poor | 1588 |

Example 9

This example demonstrates the effect on the ability to be machine processed into a powder, exhibited by a low molecular weight polymer comprising temporary networking via an associative monomer only (i.e., not further comprising a surfactant in the monomer phase).

Polymer 9 comprising 49.9/50/0.1 mol % acrylamide/ sodium acrylate/MAPTAC-C12 derivative synthesized in the following manner:

An 1,000 g aqueous solution at neutral pH containing 37 wt. % monomer mixture of 49.9/50/0.1 mol % acrylamide/ sodium acrylate/MAPTAC-C12 derivative, azo initiator, chain transfer agent, and chelant was chilled to approximately −5° C. and de-gassed with nitrogen. Polymerization was initiated with a pair of redox agents and proceeded adiabatically until the conversion of monomer reached more than 99.99% to get the targeted molecular weight of $1.0 \times 10^6$ g/mol. The resulting wet gel, which maintained a taffy like consistency and was not sticky, was processed with the aid of 1 wt. % (relative to weight of polymer gel) petroleum oil based lubricant in a cutting mill (Retsch Mill Cutter) at 1500 rpm to form granules. The wet gel granules were dried in a mesh tray in an oven at 85° C. to remove (i.e., to achieve a moisture content of about 10 wt. %) the moisture and then ground to powder. The resulting powder had a median particle size of 385.4 microns (the mean particle size was 446.4), as determined using a Horiba Laser Scattering Particle Size Distribution Analyzer LA-950 with the setting of refractive index of powder at 1.5000. The powder had an intrinsic viscosity of 5.84 dg/L and Huggins constant of 0.98 in 1 N $NaNO_3$ solution at 30° C. The powder polymer did not completely dissolve as a 1 wt. % solution in synthetic tap water with stirring of cage stirrer at 400 rpm within one hour. The powder, as a 1 wt. % solution in synthetic tap water, had a viscosity of 1588 cps, as measured on a Brookfield Model DV-E Viscometer with Spindle 63 at 30 rpm. The weight average molecular weight was determined by size exclusion chromatography using surrogate, Polymer 6.

As is apparent from the results set forth in Table 4, low molecular weight Polymer 9, not comprising a surfactant, was capable of being machine processed to form a powder. The resulting powder was sparingly soluble in water (i.e., did not completely dissolve as a 1 wt. % solution in local tap water with stirring of cage stirrer at 400 rpm within one hour).

Example 10

This example demonstrates the effect on paper dry strength exhibited by a sheet of paper treated with a powder comprising associatively networked polymer(s) via an associative monomer unit and a surfactant.

Polymer 2 (prepared according to Example 2) and Polymer 3 (prepared according to Example 3) were dissolved in water and dosed at various concentrations into cellulose fiber slurry. The treated fibers were then added to a handsheet mold and drained through a screen to form wet fiber pads. The pads were couched from the screen, pressed, and dried to yield finished paper sheets. The sheets were tested for tensile strength and compressive strength and the results set forth in FIGS. 2 and 3, respectively. In addition, the tensile strength and compressive strength results for Nalco 64114 (i.e., a glyoxylated polyacrylamide polymer), an established commercial strength agent, are provided for comparison.

Figure 2:
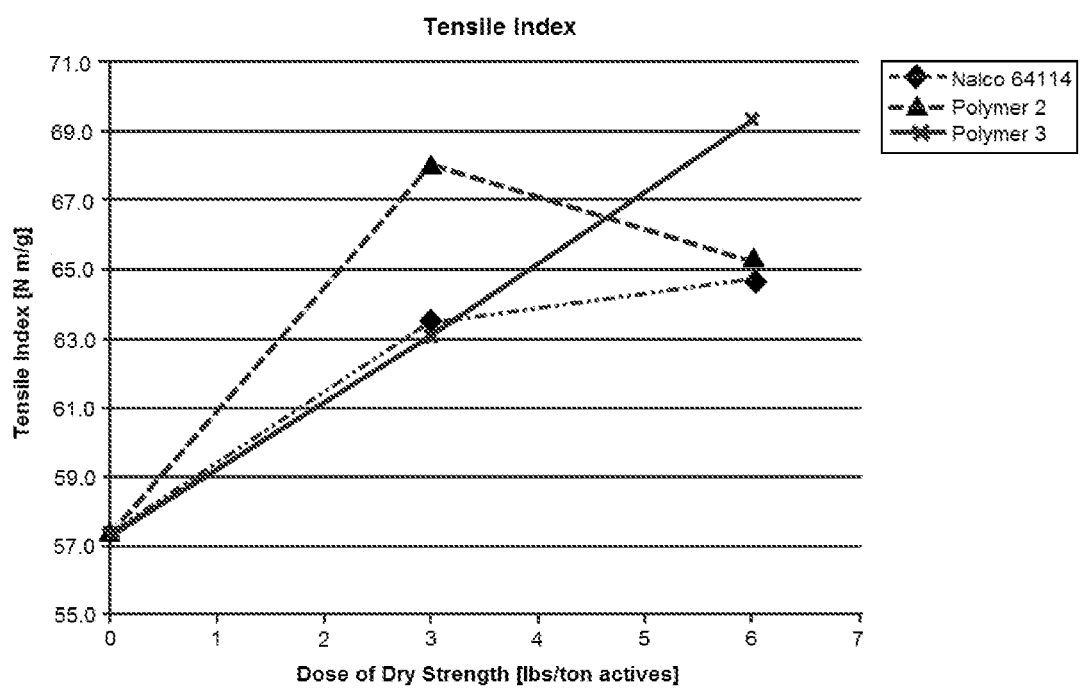
FIG. 2 graphically depicts the results of Example 10.
Figure 3:
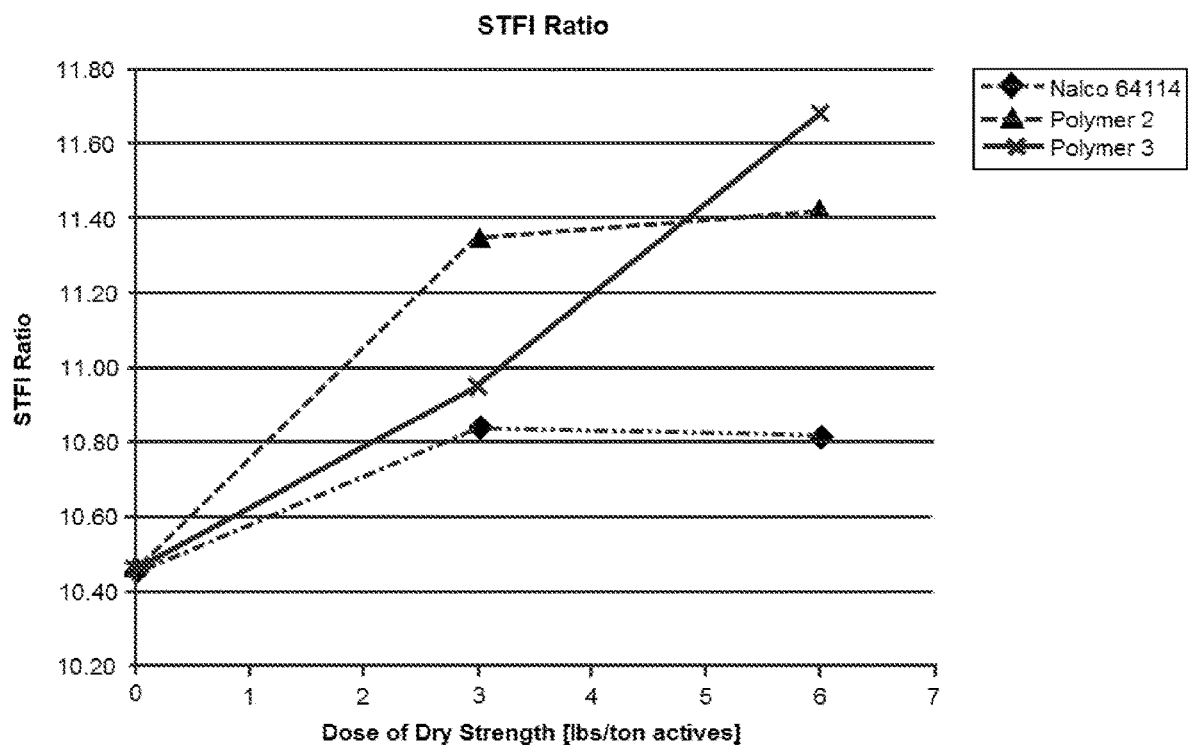
FIG. 3 graphically depicts the results of Example 10.

As demonstrated by FIGS. 2 and 3, Polymer 2 and Polymer 3 exhibit satisfactory strength properties, outperforming the standard, Nalco 64114 (i.e., a glyoxylated polyacrylamide polymer) (control), in both tensile strength and compressive strength.

Example 11

This example demonstrates the effect on paper dry strength exhibited by a sheet of paper treated with a powder comprising associatively networked polymer(s) via an associative monomer unit and a surfactant.

Polymer 1 (control, prepared according to Example 1) and Polymer 2 (prepared according to Example 2) were dissolved in water and dosed at various concentrations into a cellulose fiber slurry. The treated fibers were then added to a handsheet mold and drained through a screen to form a wet fiber pad. The pad was couched from the screen, pressed, and dried to yield the finished paper sheet. The sheet was tested for tensile strength and the results set forth in FIG. 4.

Figure 4:
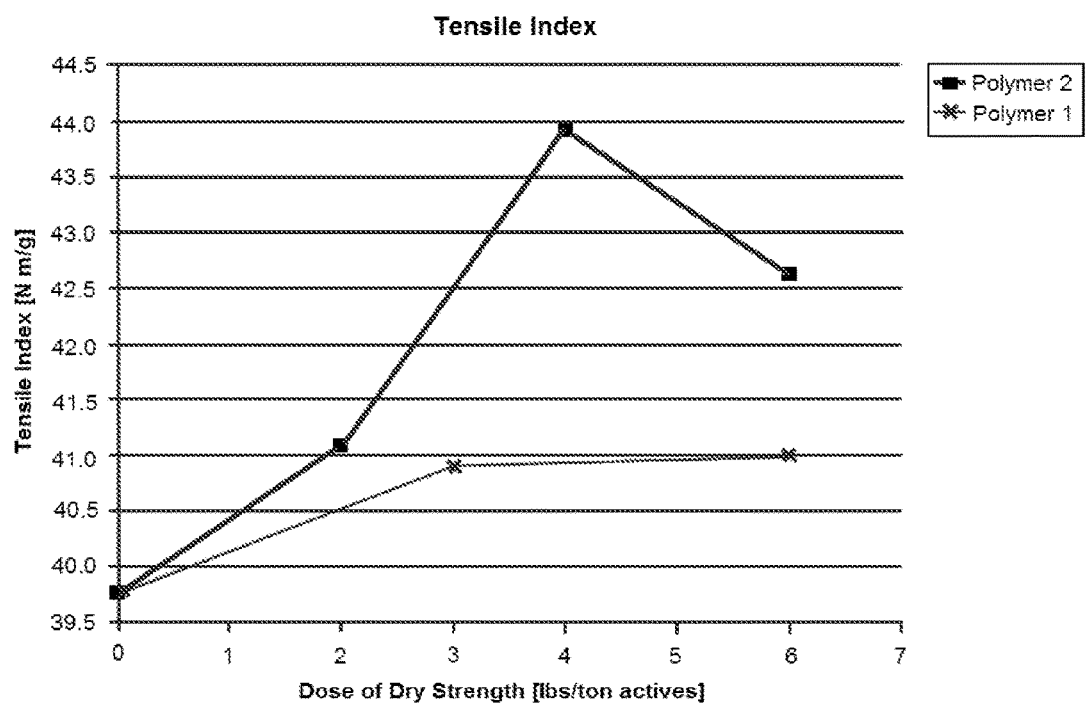
FIG. 4 graphically depicts the results of Example 11.

As demonstrated by FIG. 4, Polymer 2 exhibited improved tensile strength relative to low molecular weight Polymer 1 (control), which lacked networking via an associative monomer unit.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A powder, comprising:
one or more associative polymer(s) comprising one or more associative monomer unit(s) and one or more additional monomer unit(s) selected from at least one of a cationic monomer unit, an anionic monomer unit, a nonionic monomer unit, a zwitterionic monomer unit, or a combination thereof, and one or more surfactant(s),
wherein the one or more associative polymer(s) have a weight average molecular weight of from about 10 kDa to about 2,000 kDa, and
wherein at least one of the one or more associative monomer units is derived from a monomer of Formula II:

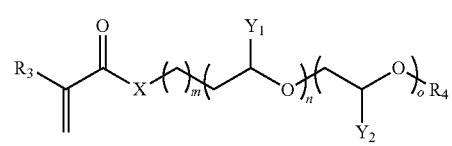

wherein $R_3$ is H or $C_1$-$C_{10}$ alkyl, X is O or NH, n is an integer from 1 to 100, o is an integer from 0 to 100, m is at least 5, each $Y_1$ and $Y_2$ are independently H or $C_1$-$C_4$ alkyl, and $R_4$ is H or a hydrophobic group.

2. The powder of claim 1, wherein the additional monomer unit is derived from a monomer selected from a monomer of Formula I:

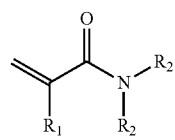

wherein $R_1$ is H or $C_1$-$C_4$ alkyl and each $R_2$ is independently H or an organic group; 2-(dimethylamino)ethyl acrylate ("DMAEA"), 2-(dimethylamino)ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N- trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid; salts thereof, and combinations thereof.

3. The powder of claim 1, wherein the additional monomer unit is derived from a monomer of Formula I:

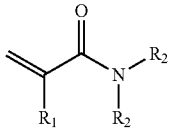

I wherein $R_1$ is H or $C_1$-$C_4$ alkyl and each $R_2$ is independently H or an organic group.

4. The powder of claim 1, wherein the additional monomer unit is derived from a monomer selected from 2-(dimethylamino)ethyl acrylate ("DMAEA"), 2-(dimethylamino) ethyl methacrylate ("DMAEM"), 3-(dimethylamino)propyl methacrylamide ("DMAPMA"), 3-(dimethylamino)propyl acrylamide ("DMAPA"), 3-methacrylamidopropyl-trimethyl-ammonium chloride ("MAPTAC"), 3-acrylamidopropyl-trimethyl-ammonium chloride ("APTAC"), N-vinyl pyrrolidone ("NVP"), N-vinyl acetamide, hydroxyethyl methacrylate, hydroxyethyl acrylate, diallyldimethylammonium chloride ("DADMAC"), diallylamine, vinylformamide, 2-(acryloyloxy)-N,N,N-trimethylethanaminium chloride ("DMAEA.MCQ"), 2-(methacryloyloxy)-N,N,N-trimethylethanaminium chloride ("DMAEM.MCQ"), N,N-dimethylaminoethyl acrylate benzyl chloride ("DMAEA.BCQ"), N,N-dimethylaminoethyl methacrylate benzyl chloride ("DMAEM.BCQ"), 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid; salts thereof; and combinations thereof.

5. The powder of claim 1, wherein the surfactant is a nonionic surfactant of formula XII

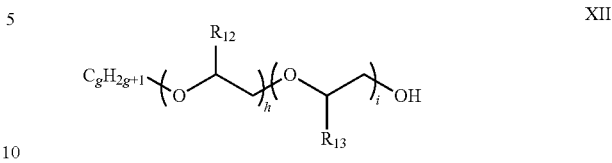

XII wherein g is an integer ranging from about 12 to about 50; i is 0, $R_{12}$ is H, and h is an integer ranging from about 10 to about 100.

6. The powder of claim 1, wherein the one or more associative polymer(s) comprises a sum total from about 0.005 mol % to about 10 mol % of the one or more associative monomer unit(s).

7. The powder of claim 1, wherein the one or more associative polymer(s) comprises a sum total from about 90 mol % to about 99.995 mol % of the one or more additional monomer unit(s).

8. The powder of claim 1, wherein the powder, at a median particle size of at least 300 microns, is completely soluble as up to a 1 wt. % solution in water with stirring by a cage stirrer at 400 rpm within one hour at room temperature.

9. The powder of claim 1, wherein the powder has an intrinsic viscosity of from about 0.05 dL/g to about 7 dL/g.

10. The powder of claim 1, wherein the powder has a Huggins constant of from about 0.3 to about 10.

11. The powder of claim 1, wherein the surfactant is $HO(C_2H_4O)_{101}(C_3H_6O)_{56}(C_2H_4O)_{101}H$, polyethoxy (25) lauryl alcohol, polyethoxy (25) cetyl alcohol, polyethoxy (25) stearyl alcohol, polyethoxy (25) behenyl alcohol, or any combination thereof.

12. The powder of claim 1, wherein the powder comprises a sum total of about 0.001 wt. % to about 20 wt. % of the one or more surfactants.

13. The powder of claim 1, wherein the powder has a moisture content from about 0 wt. % to about 30 wt. %.

* * * * *

UNITED STATES PATENT AND TRADEMARK OFFICE
CERTIFICATE OF CORRECTION

PATENT NO. : 10,920,065 B2
APPLICATION NO. : 15/620176
DATED : February 16, 2021
INVENTOR(S) : Heqing Huang et al.

Page 1 of 1

It is certified that error appears in the above-identified patent and that said Letters Patent is hereby corrected as shown below:

In the Claims

Column 69, Claim 2, Line 8 - Delete "thereof," and insert -- thereof; --.

Column 70, Claim 5, Line 11 - After " 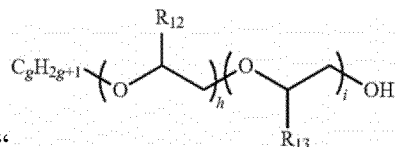 " insert -- , --.

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*